(12) United States Patent
Kim et al.

(10) Patent No.: US 7,797,112 B2
(45) Date of Patent: Sep. 14, 2010

(54) METHOD OF IDENTIFYING A FABK PROTEIN INHIBITOR USING A THREE-DIMENSIONAL STRUCTURE OF FABK PROTEIN

(75) Inventors: Eunice Eun-Kyeong Kim, Seoul (KR); Byung Hak Ha, Seoul (KR)

(73) Assignee: Korea Institute of Science and Technology, Seongbuk-gu, Seoul (KR)

( * ) Notice: Subject to any disclaimer, the term of this patent is extended or adjusted under 35 U.S.C. 154(b) by 36 days.

(21) Appl. No.: 11/965,989

(22) Filed: Dec. 28, 2007

(65) Prior Publication Data

US 2009/0170117 A1    Jul. 2, 2009

(51) Int. Cl.
G01N 31/00 (2006.01)
G06G 7/58 (2006.01)
C12Q 1/26 (2006.01)

(52) U.S. Cl. .............................. 702/27; 703/11; 435/25

(58) Field of Classification Search ........................ None
See application file for complete search history.

(56) References Cited

U.S. PATENT DOCUMENTS 5,579,250 A * 11/1996 Balaji et al. ..................... 506/8
6,613,553 B1    9/2003 Rock et al.
2004/0137518 A1 * 7/2004 Lambert et al. ............... 435/7.1

FOREIGN PATENT DOCUMENTS

WO    2006/008660 A2 *    1/2006

OTHER PUBLICATIONS

Saito et al., Acta Cryst. F62 576-578, 2006.*
Flower, "Drug Design, Cutting Edge Approaches," Royal Society of Chemistry, Cambridge, UK, 2002, pp. 21-27.*
GenBank Accession No. NP_228609, GI:15643563, Dec. 2005.*
Merriam-Webster Online Dictionary definition of "represent" at www.merriam-webster.com/dictionary/represent, last viewed on Jun. 26, 2009.*
Merriam-Webster online dictionary definition of "react", obtained from www.merriam-webster.com, last viewed on Nov. 18, 2010.*
Marrakchi et al., Biochem J. 370:1055-1062, 2003.*
Nelson K.E., et al, "Evidence for lateral gene transfer between Archaea and bacteria from genome sequence of *Thermotoga maritima*", Nature. vol. 399(6734): 323-329 May 27, 1999.
Freundlich, J.S., et al, "Synthesis, Biological Activity, and X-Ray Crystal Structural Analysis of Diaryl Ether Inhibitors of Malarial Enoyl Acyl Carrier Protein Reductase. Part 1. 4′-Substituted Triclosan Derivatives", Bioorg Med Chem Lett. vol. 15(23): 5247-5252. Dec 1, 2005.
Oliveria, J, S., et al., "Crystallographic and Pre-steady-state Kinetics Studies on Binding of NADH to Wild-type and Isoniazid-resistant Enoyl-ACP(CoA) Reductase Enzymes from Mycobacterium tuberculosis", Brasil, J Mol Biol. vol. 359(3): 646-666, Jun. 9, 2006.
Payne, D.J., et al., "Discovery of a Novel and Potent Class of FabI-Directed Antibacterial Agents", Antimicrobial Agents Chemotherapy, vol. 46, No. 10: p. 3118-3124, Oct. 2002.

* cited by examiner

*Primary Examiner*—David J Steadman

(57) ABSTRACT

The present invention relates to a FabK (enoyl-acyl carrier protein reductase) protein derived from a *Thermotoga maritima* strain. In the present invention, the active site and the three-dimensional crystal structure of the protein are determined, a novel inhibitor against the FabK protein is screened and/or designed using the three-dimensional crystal structure thereof, and thereby developing a novel active compound, namely active-controlling material with excellent antibiotic activities against strains having a resistance to previous antibiotics.

4 Claims, 8 Drawing Sheets

Affinity (Ni-NTA)

METHOD OF IDENTIFYING A FABK PROTEIN INHIBITOR USING A THREE-DIMENSIONAL STRUCTURE OF FABK PROTEIN

BACKGROUND OF THE INVENTION (a) Field of the Invention

The present invention relates to a FabK (enoyl-acyl carrier protein reductase) protein derived from a *Thermotoga maritima* strain. In the present invention, the active site and the three-dimensional crystal structure of the protein are determined, a novel inhibitor against the FabK protein is screened and/or designed using the three-dimensional crystal structure thereof, and thereby developing a novel active compound, namely active-controlling material with excellent antibiotic activities against strains having a resistance to previous antibiotics.

(b) Description of the Related Art

Triclosan, which is known as an antibacterial agent having comprehensive antibacterial activities, has been used to give antibiosis and antibacterial activities to various products for the past 30 years. For example, the triclosan is included in various products such as soaps, shampoos, washing agents, dentifrices, cosmetics, toys, rugs etc. Therefore, the category of usage of triclosan is the same as for ultraviolet or bleach.

Triclosan inhibits the activity of enzymes called enoyl-[acyl-carrier-protein] reductase (E.C. 1.3.1.9), which is also known as NADH-dependent trans-2-enyol-ACP reductase (ENR), or FabI. FabI exists in almost all bacteria and fungi, and it is an essential enzyme for living microorganisms since it is one of enzymes involved in biosynthesis of fatty acid and fatty acid is essential for forming the cell membrane. Therefore, triclosan is used in a wide range of biocides.

In the case of mycobacteria of an aerobic bacteria, the enzyme that carries the action of the enoyl-ACP reductase or FabI is called InhA. The two enzymes, InhA and FabI, shares rather low sequence identities, but the key residues at the active site of the two enzymes are the same. Thus, InhA shares the same enzymatic mechanism as FabI. Isoniazid, the existing antitubercular agent, inhibits InhA in the same manner as triclosan inhibiting FabI.

Fatty acids are central building blocks of life, since they are constituents of cell membranes, energy storage compounds, and messenger substances, and they act as posttranslational protein modifiers and modulate gene expression. Therefore, the de Novo synthesis of fatty acid is essential for all living organisms. It involves a conserved set of chemical reactions for the cyclic stepwise elongation of activated precursors by two carbon units. The growing fatty acid is attached to a carrier protein, acyl carrier protein (ACP), throughout its synthesis and is released once it reaches certain length.

Although all organisms use variations of this common synthetic scheme, it appears that there are three distinct architectures for fatty acids synthesis. In bacteria, all reactions are carried out by individual, mono-functional proteins in a dissociated manner. On the contrary, the eukaryotic type I FAS consists of large multifunctional polypeptides. Fungal FAS is a 2.6MD α6β6 dodecamer, while the FAS of vertebrates and mammals are a α2 homodimer of a single 270-kDa polypeptide. FabI manages the process that reduces the Enoyl-ACP corresponding to the final step among the steps, and then the reduced Enoyl-ACP is converted into Acyl-ACP.

As described in above, FabI performs an essential role for the biosynthesis of fatty acids by catalyzing the elongation of the lipid in the final step of the biosynthesis of lipids. FabI belongs to the short-chain alcohol dehydrogenase/reductase (SDR) superfamily, and it forms a tetramer like other family members. In FabI isolated from *E. coli*, the FabI uses the coenzyme called NADH [Egan, A. F. and Russel, R. R. B., Genet. Res., 21, 3603-3611 (1973)]. Recently, according to the FabI-triclosan complex structure, the triclosan is located at the upper part of the NAD+ of NADH, to occupy the active site of the FabI enzyme, even though triclosan is non-covalent, because it has quite strong binding activity with the FabI enzyme, and thereby the function of the enzyme is inhibited [Heath, R. J., et al., J. Biol. Chem., 274, 11110-11114 (1999)]. In the case of a staphylococcus aureus, it is clarified that FabI uses NADPH as a coenzyme but not NADH, and the triclosan inhibits the activity of the FabI enzyme through an interaction similar to the above. Therefore, FabI inhibitors, which are being developed in universities and various research institutes as well as by pharmaceutical companies, are compounds having a mechanism similar to triclosan.

But recently, it was reported that a part of major pathogens, such as *Streptococcus pneumoniae*, have resistance against triclosan [Heath, R. J. and Rock, C. O., Nature, 406, 145-146 (2000)]. In these resistant strains, although the FabI enzyme did not exist in the strains, because a FabK gene exists in the gene cluster of the strains, it was clarified that the FabK protein is expressed and produced by the FabK gene, and it performs a role identical to the FabI protein. It was reported that strains including *Enterococcus faecalis* and *Thermotoga maritima* use also FabK instead of FabI in the pathway of biosynthesis of fatty acids. The gene sequence coding the FabK protein is different from the gene sequence coding the previous FabI protein, and does not have any similarity with the gene sequence coding other proteins of the SDR superfamily. In FabK existing in strains, such as *Enterococcus faecalis* and *Thermotoga maritima*, the amino acid sequence of the FabK has the sequence identity of 68% and 48% when compared with the FabK amino acid sequence of *Streptococcus pneumoniae*, respectively [Marrakchi, H., et al., Biochem. J., 370, 1055-1062 (2003)]. Therefore, FabK is a flavoprotein, it needs NADH as a coenzyme for its activity, and it is a protein that is not deactivated by triclosan.

Because the current antitubercular agents mostly relate to FabI/InhA, strains having resistance to the antitubercular agents through not using FabI/InhA are often being discovered. These strains use FabK instead of FabI. For example, it has been clarified that *S. pneumoniae* of a major strain of respiratory disease or *E. facalis* having a resistance against vancomycin uses also FabK instead of FabI. Namely, in order to have antibiotic activities against the resistant strains, a novel compound inhibiting the activity of FabK, not FabI, is necessary. According to reports up to now, the mechanism of operating FabK differs from the mechanism of operating FabI. Therefore, research for the structure and the function of FabK is acutely required.

SUMMARY OF THE INVENTION

The present inventors isolated and purified a FabK protein derived from *Thermotoga maritima*, and determined the three-dimensional crystal structure of the protein. Also, the present inventors defined the amino acids contributing to the active mechanism of FabK through a mutant test of individual amino acids in the active site of FabK, and proved that the structure of FabK is different from FabI. Further, the present inventors completed the present invention by providing technology useful for the development of novel antibiotics.

An object of the present invention is to determine the active site of the FabK protein.

Another object of the present invention is to determine the three-dimensional crystal structure of the FabK protein.

Another object of the present invention is to provide a method of screening compounds having inhibitory activities against the FabK protein through interacting with the FabK protein by using the active site and/or the three-dimensional crystal structure of the FabK protein.

DETAILED DESCRIPTION OF THE PREFERRED EMBODIMENTS

Figure 1:
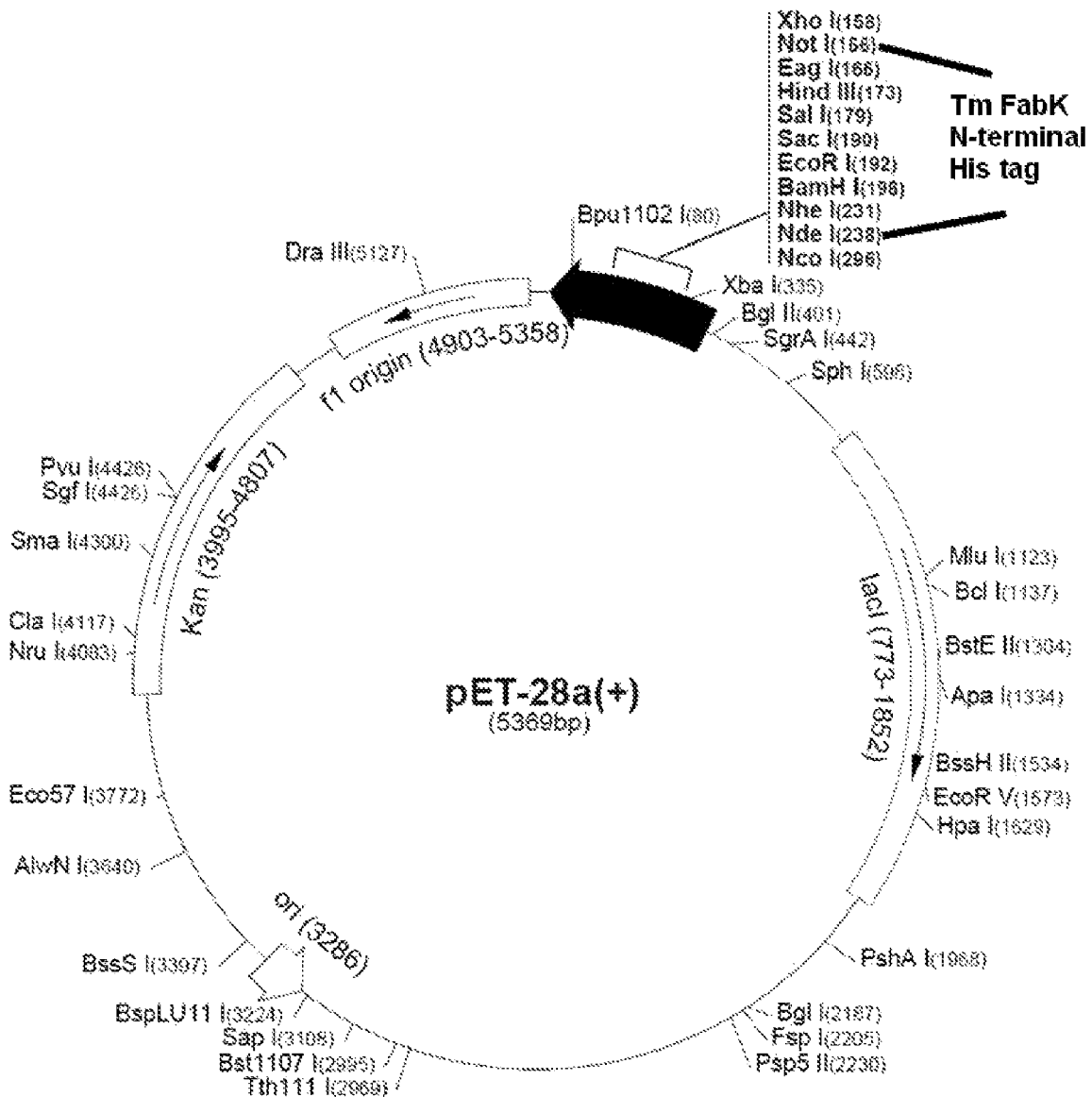
FIG. 1 shows the expression vector and the cloning information of the present invention.
Figure 2:
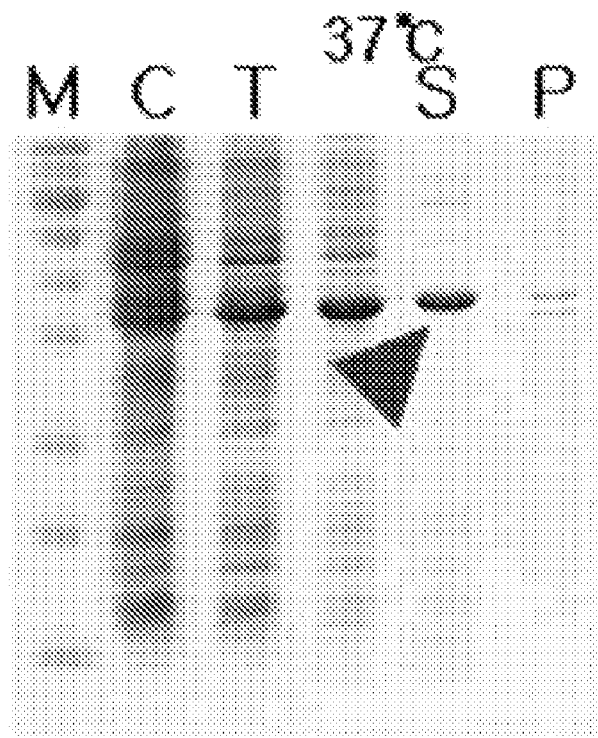
FIG. 2 shows test results of expression level of the FabK protein expressed by the expression vector.
Figure 3:
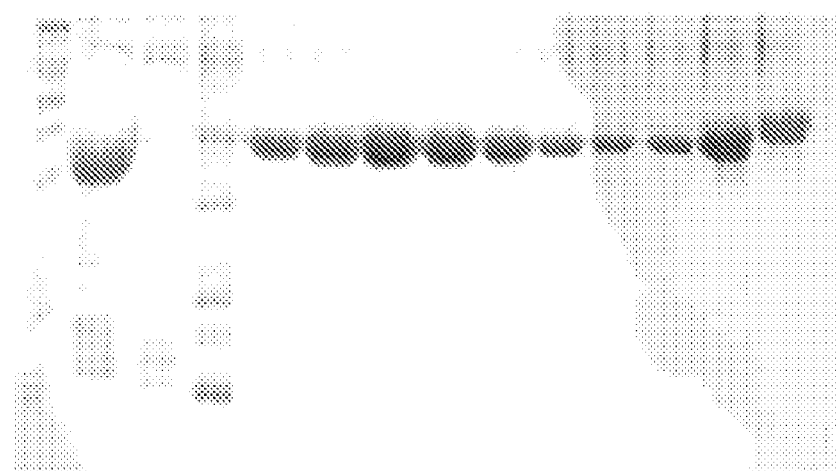
FIG. 3, FIG. 4, and FIG. 5, respectively, show the purification steps of the FabK protein.
Figure 4:
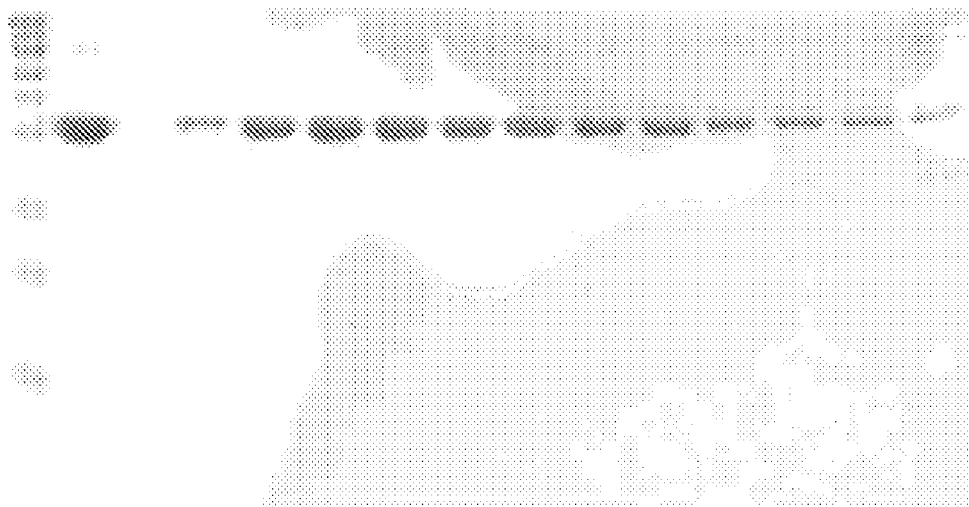
Figure 5:
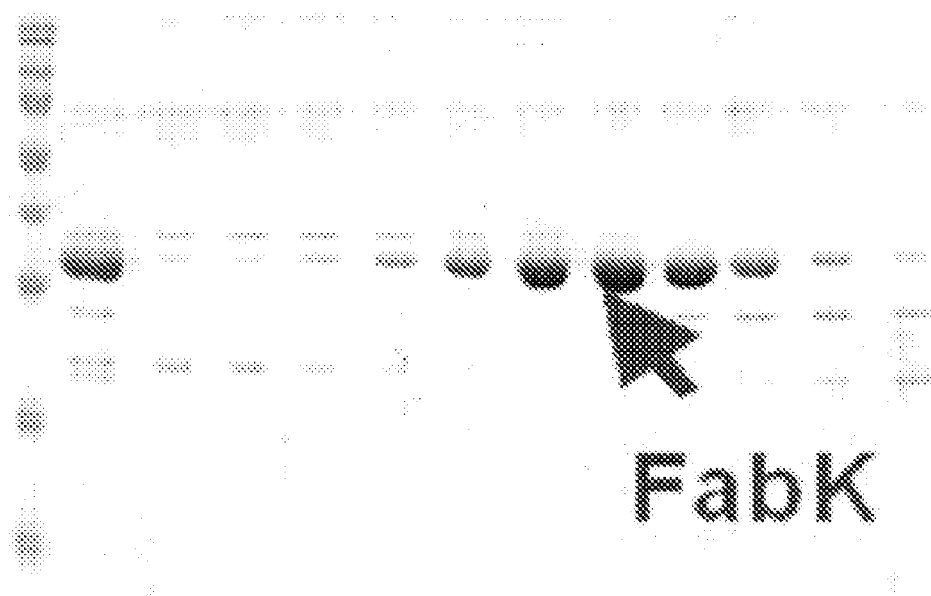
Figure 6:
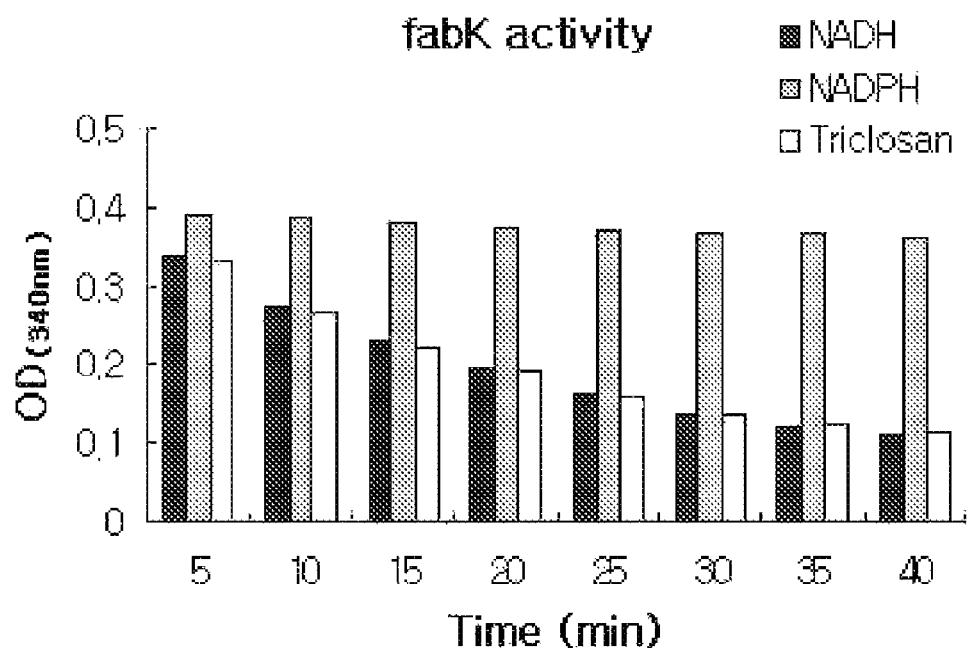
FIG. 6 shows activities of the FabK protein according to NADH- and NADPH-dependency.

A more complete appreciation of the invention, and many of the attendant advantages thereof, will be readily apparent as the same becomes better understood by reference to the following detailed description.

The present invention relates to a FabK (enoyl-acyl carrier protein reductase) protein derived from a *Thermotoga maritima* strain. In the present invention, the active site and the three-dimensional crystal structure of the protein are determined, a novel inhibitor against the FabK protein is screened and/or designed using the three-dimensional crystal structure thereof, and thereby developing a novel active compound, namely active-controlling material with excellent antibiotic activities against strains having a resistance to previous antibiotics.

The present invention will now be explained in more detail.

Firstly, the present invention provides a FabK protein isolated and purified from a *Thermotoga maritima*. In the present invention, the protein has the amino acid sequence of SEQ ID NO: 1, and the amino acid sequence that affects the FabK protein acting as an enzyme was clarified for the first time. As described in above, the FabK protein is an enzyme used instead of FabI protein in many bacteria and fungi, and it is very useful as a target protein in the development of novel antibiotics against strains having a resistance to FabI inhibitors. Because the FabK protein according to the present invention is soluble and has a crystal structure analyzed by an appropriate method for the FabK protein, the three-dimensional structure analysis of the protein is facilitated, and the protein is useful as a new target protein for the development of novel antibiotics.

Also, the present invention provides an expression vector of the FabK protein of including: a nucleotide sequence coding the *Thermotoga maritima* FabK having the amino acid sequence of SEQ ID NO: 1; and a promoter and a terminator, which are operably linked to the nucleotide sequence. Further, the expression vector may include commercially used selection markers, such as the kanamycin-resistant gene, the ampicilin-resistant gene, the tetracycline-resistant gene, and the chloromycetin-resistant gene. Also, the present invention provides a transformant transformed by the expression vector of the FabK protein. The host used for the transformant is not particularly limited, as long as it is a prokaryotic bacterium, which has pBR322 as a replication origin and produces T7 polymerase. For example, *Escherichia coli* (*E. coli*) may be used. Also, the present invention provides a method of preparing a FabK protein including the steps of: transforming the expression vector of the FabK protein into a host, to prepare a transformant containing the expression vector; and culturing the prepared transformant, to produce the FabK protein.

For preparing the expression vector, as shown in the SEQ ID NO: 1, without the deletion of any amino acid, a nucleotide sequence coding a *Thermotoga maritima* FabK protein having the amino acid sequence from methionine (N-terminus) of the $1^{st}$ amino acid to glutamate of the $314^{th}$ amino acid in the FabK protein may be used, and for facilitating the purification of the prepared protein, the N-terminus bound with a tag having 6 histidine may be used.

The expression vector, the transformant, and the method of preparing the FabK protein according to the present invention will be explained in more detail in the following embodiments. These embodiments, however, should not be interpreted as limiting the scope of the present invention in any manner:

Firstly, for amplifying a gene coding the FabK protein from the genomic DNA of a *Thermotoga maritima*, each primer used for the polymerase chain reaction (hereinafter referred to as 'PCR') corresponding to the 5'-terminus and 3'-terminus of the gene was designed and synthesized. The primers were designed for having the restriction enzyme recognition site identical with the restriction enzyme recognition site existing in the cloned vector, to facilitate the cloning.

The gene coding the FabK protein was amplified by the PCR reaction using the genomic DNA of a *Thermotoga maritima* and the primers as a template. The amplified gene was cut with available restriction enzymes, and then it was subcloned into an expression vector, for example an *E. coli* vector, to prepare a recombinant expression vector including the FabK gene. The available restriction enzyme sites are as follows: NdeI, NheI, BamHI, EcoRI, SalI, HindIII, NotI, and XhoI. In the preferred specific embodiments of the present invention, the NdeI and XhoI as the restriction enzyme sites may be used. As described in above, the expression vector may include commercially used selection markers, such as the kanamycin-resistant gene, the ampicilin-resistant gene, the tetracycline-resistant gene, and the chloromycetin-resistant gene, to facilitate confirmation of whether the expression vector is inserted into the host genome or not. The prepared recombinant expression vector may be transformed into an appropriate host for preparing a transformant, for example, an *E. coli*, and then it may be cultured in appropriate cultivation conditions for expressing the protein. The cultivation conditions may be changed according to the used host, and preferably may be cultured for 3~15 h at 15~40° C. The conditions may also be controlled by the cultivation time, through reducing the cultivation time at high temperature and extending the cultivation time at low temperature.

Whether the target protein was produced or not can be confirmed by using a commercial protein identification method, such as SDS-polyacrylamide gel electrophoresis or western blot. The transformant transformed with the expression vector including the recombinant FabK gene may be cultured in a medium (for example, Luria-Bertani medium) including antibiotics corresponding to selection markers, such as ampicillin, tetracycline, kanamycin, and chloramphenicol, and then IPTG (isopropyl-β-D-thiogalactopyranoside) may be added to the medium when the cultured medium is reached in the proper cell density (for example, the absorbance at 600 nm is from 0.5 to 0.7), to induce the expression of the recombinant FabK gene. The cultured medium is centrifuged to precipitate the transformant, and the precipitated transformant is suspended in an appropriate buffer solution. After centrifugation, the supernatant including the protein is separated, and then the separated protein may be isolated and purified by using a commercial protein isolation and purification apparatus, such as ion-exchange chromatography, affinity chromatography, and gel filtration chromatography, to obtain purified recombinant FabK protein. The recombinant FabK protein may also be prepared in the form of a His-tag fusion protein for facilitating the purification.

In another aspect, the present invention is characterized by providing more useful information for determining the three-dimensional crystal structure and the active site of the FabK protein and for screening inhibitory compounds targeting the FabK protein.

In another aspect, the present invention provides a crystal of the FabK-FMN complex having the three-dimensional structure expressed by at least one atomic coordinate information selected from the group consisting of the atomic coordinate information shown in the following Table 1 or Table 2. The FMN is an essential cofactor for the activity of the FabK protein, particularly because it forms the complex together with the FabK protein in vivo experiment, is considered that the FabK protein and the FMN molecule acts on the complex shape in vivo. Therefore, the crystal structure of the FabK-FMN complex provided by the present invention can be very effectively applied to screen and develop a novel inhibitor against the FabK protein.

Based on the three-dimensional crystal structure of the FabK protein and/or the specific positional characterization of the binding between the FabK and the flavin mononucleotide (FMN), and the role of the individual amino acid affecting the activity at the active site, the present invention also provides a method of developing an inhibiting agent against the activity of the FabK protein, characterized by screening an inhibitor or designing a novel inhibitory compound against the activity of the FabK protein.

In one specific embodiment of the present invention, the method of developing an inhibiting agent may include the steps of: reacting the FabK protein having the amino acid sequence of SEQ ID NO: 1 or the FabK-FMN complex with candidate compounds; and screening a compound from the candidate compounds, which interacts with the FabK protein or the complex, to determine the compound as an inhibitor against the activity of the FabK protein.

In another specific embodiment, the method of developing an inhibiting agent of the present invention is characterized by de-novo designing a new compound able to bind to the FabK protein or the FabK-FMN complex using the x-ray diffraction pattern data shown in the following Table 1 or at least one information of the three-dimensional crystal structure selected from the group consisting of the 2389 atomic coordinates shown in the following Table 2.

In another specific embodiment, the method of developing an inhibiting agent of the present invention is characterized by screening a new compound able to bind to the FabK protein or the FabK-FMN complex, using a virtual screening method based on the information of the three-dimensional crystal structure of a candidate compound with the x-ray diffraction pattern data shown in following Table 1 or at least one information of the three-dimensional crystal structure selected from the group consisting of the 2389 atomic coordinates shown in following Table 2.

In the screening the compound interacting (binding) with the FabK protein, the compound as an inhibitor against the activity of the FabK protein may be selected more easily and exactly by using the three-dimensional crystal structure and/or the information of the active site.

The FabK protein inhibitor selected by the screening method according to the present invention acts as antibiotics, and a strain existing the activity of the antibiotics is not particularly limited, and may be any microorganism that essentially needs the FabK protein and any protein having an active site like the protein. For example, the strain may be selected from the group consisting of *Streptococcus pneumoniae, Enterococcus faecalis, Thermotoga maritima, Streptococcus pyogenes, Neorickettsia sennetsu, Ehrlichia chaffeensis, Anaplasma phagocytophilum, Carboxydothermus hydrogenoformans, Streptococcus agalactiae*, and *Clostridium difficile*.

In more detail, the present invention will be described as follows:

Firstly, the present invention provides a method of crystallizing a FabK protein. In determining the three-dimensional crystal structure of a target protein for developing new antibiotics, it is important that the target protein is water-soluble and crystalline. Because the FabK protein according to the present invention is water-soluble, in order to determine the three-dimensional crystal structure of the FabK protein, a step of crystallizing the FabK protein to form the crystal structure is required. In the crystallizing step, generally, an x-ray crystallography method is used, and various crystallizing methods, a step of pre-treating for using the x-ray crystallography method, have to be performed In the preferred specific embodiments of the present invention, commercial method using the concentration equilibrium, for example, a vapor diffusion method (for example, a sitting- or hanging-drop vapor diffusion method [Jancarik J. et al., *Appl. Cryst.*, 24, 409-411 (1991), which is incorporated herein by reference] or a dialysis method (for example, continuous-type or batch-type, as the crystallizing method may be used; Bunick C. and Stubbs G., Acta Cryst. D56, 1430-1431 (2000)).

The crystallizing principle and process of the hanging-drop vapor diffusion method are as follows. When a small drop of mother liquor and a reservoir solution of much bigger scale are separated and coexist in an enclosed space, the movement of water or other volatile material occurs in the space. On the other hand, in the oversaturated state of a thermodynamically metastable state of a solution condition of a protein, a precipitation of the protein occurs according to a kind of precipitant, and the precipitated protein becomes a stabilized crystallizing state while the speed of the precipitation speed is slowly progressed. The available precipitant is well known, and it reduces the solubility of a concentrated protein solution. In order to reduce a relative absorption layer surrounding the protein molecules, the protein molecules are concentrated, and then a crystal is formed. Therefore, the reservoir solution is mixed with materials, such as a precipitant, a buffer solution, a salt, and a detergent, under various concentrations, wherein the protein solution and the reservoir solution including the materials are mixed, generally, in a ratio of about 1:1, and then form a drop. Next, the drop is placed on a glass slide coated with silicon, and it is put onto a plate prepared in an upset condition, and then sealed. Initially, because the concentration of the protein in the drop differs from the concentration of the reservoir solution, the protein is not a crystallizing state. However, when it is formed in the sealed condition, the balance of the concentration is gradually made, and then a crystal is formed by the principle as described in above in specific conditions. In the hanging-drop vapor diffusion method, not only the precipitant of the reservoir solution but also the kind of a salt, a buffer solution, and a detergent, and thereof appropriate concentrations, the pH and a test temperature of the solution may be selected according to the kind of the protein, and these may often be quite important elements for forming the protein crystals.

In order to crystallize the water-soluble FabK protein, the FabK protein solution and the reservoir solution may be reacted by using the concentration equilibrium method, for example such as a sitting- or hanging-drop vapor diffusion method, a dialysis method, and then a crystallization is performed.

The reservoir solution may comprise buffer solution, salt and precipitant. The buffer solution is used for stabilizing the FabK protein by controlling pH, wherein the pH range of the buffer solution may be from pH 4 to 9.5, preferably may be from pH 4.6 to 9, more preferably may be from pH 6.2 to 8.5, for example, the available buffer solution may include at least one buffer solution from the group consisting of PIPES buffer, Bicine, Tris, sodium acetate, sodium succinate and Bis-Tris.

The salt is used for generating the protein crystal which is advantageous for an easy structural analysis. The salt may be one or more selected from the group consisting of metal salts and ammonium salts. The ammonium salt may be one or more selected from the group consisting of ammonium sulfate (($NH_4)_2SO_4$), ammonium chloride, ammonium phosphate, and the like. The metal salt may be one or more selected from the group consisting of all alkali metal (e.g., lithium, sodium, etc.) salts, alkali earth metal (e.g., magnesium, etc.) salts, and transition metal (e.g. manganese, zinc, etc.) salts, preferably, selected from the group consisting of chlorides, cyanates, thiocyanates, oxides, nitrates, hydroxides, sulfates, and the like. For example, the salt may be one or more selected from the group consisting of lithium chloride, magnesium chloride, sodium thiocyanate, and the like.

The precipitant is used for generating precipitate for crystallization. The precipitant may be one or more selected from the group consisting of C1-C4 linear or branched alcohols, and polypropylene glycol (PEG) (weight-average molecular weight of at least 200, preferably 400 to 20,000, more preferably 550 to 10,000).

The concentration of the buffer solution, the salt, and the precipitant within the whole reservoir solution may be appropriately controlled according to the concentration of the protein solution. In more detail, the concentration of the buffer solution, such as PIPES buffer, Bicine, Tris and the like, in the reservoir solution may be from 0.005 to 1.5 M, preferably from 0.01 to 0.2 M. The concentration of the salt, such as lithium chloride, magnesium chloride, sodium thiocyanate, ammonium sulfate and the like, in the reservoir solution may be from 0.05 to 2 M, preferably from 0.05 to 0.5 M. The concentration of the precipitant, such as alcohols or PEG, in the reservoir solution may be from 1 to 40 (v/v) %, preferably from 5 to 30 (v/v) %. In the concentration of the precipitant and the salt included in the reservoir solution, if the concentration is higher than the above described ranges of concentration, the precipitation of the protein may occur, and if the concentration is lower than the ranges, the crystal of the protein cannot be formed. Further, the buffer solution mainly relates to the stability of the protein within the reservoir solution, and if the concentration deviates from above described ranges of concentration, the stability and the desired crystal of the protein cannot be obtained. The reservoir solution may further include a commercially available salts, buffer solutions, and detergents as well as the above components.

The FabK protein solution is a solution wherein FabK protein is dissolved in a proper solvent. The solvent for dissolving FabK protein may be any of FabK protein soluble solvents, for example, one or more selected from the group consisting of PIPES buffer, Bicine, Tris, Na acetate, Na succinate, Bis-Tris, HEPES(N-(2-Hydroxyethyl)piperazine-N'-(2-ethanesulfonic acid)), Imidazole, sodium phosphate, potassium phosphate, MES, ADA(adenosine deaminase), Na cacodylic acid, tri-Na citrate, and the like. In order to facilitate the formation of the protein crystal having a structure advantageous for an easy structural analysis, the concentration of the FabK protein solution may be adjusted from 3 to 30 mg/ml, preferably from 5 to 20 mg/ml, more preferably from 8 to 15 mg/ml.

In the present invention, it may be preferable that the concentration of the FabK protein solution is roughly inverse proportion to that of the precipitant in the reservoir solution. That is, as the concentration of the FabK protein solution gets higher, the crystallization of the protein gets easier, and thus, the concentration of the precipitant required to crystallize the protein is relatively low. On the other hand, when the concentration of the FabK protein solution is low, relatively high concentration of the precipitant is required to crystallize the protein. For example, when the concentration of the protein solution is about 10 mg/ml, the concentration of the precipitant may be preferably from about 15% (v/v) to about 20% (v/v).

In addition, the concentration equilibrium method preferably may be performed under the pH from 8 to 9. The pH range is experimentally determined, and the most suitable crystal structure may be obtained when reacted within the pH range. In the reaction of forming the crystal according to the method, preferably the reaction may be performed under the temperature about from 4 to 26° C., and more preferably may be performed under from 20 to 24° C. Further, the reaction preferably may be performed under the reaction period from 1 to 20 days, and more preferably may be performed under the period from 1 to 2 weeks. The range of the reaction temperature and the reaction period is experimentally determined, to obtain a crystal having the optimal data for performing facilitative x-ray analysis.

For analyzing the structure of the prepared crystalline FabK protein, x-ray analysis may be used. However, if the protein crystal is exposed to the high energy of the x-rays, because the lifetime of the crystal is shortened and the intensity of the data is weakened, the result obtained from the structure analysis is poor. Therefore, in order to prevent possible decay of the protein crystal, preferably, a flash-frozen nitrogen cooling method may be performed before the x-ray analysis. In the case of performing the method, preferably ethyleneglycol and paraton-N oil may be further included in the crystalline condition, to effectively protect the crystal of the FabK protein. In the case of using ethyleneglycol, the concentration of ethyleneglycol may be from 20 to 35 (v/v) %, and preferably from 25 to 30 (v/v) %. It is preferable that the paraton-N covers the crystal and then is used. In the flash-frozen nitrogen cooling method, the temperature of performing the method may be from 50 to 200 K, and preferably from 80 to 120 K. The range of the concentration and the temperature are experimentally determined, to well endure against nitrogen stream without affecting the crystalline of the FabK protein, and to well keep the FabK protein within the flash nitrogen.

In addition, the present invention provides the three-dimensional crystal structure of the FabK protein determined by using the method obtained through x-ray crystallography. In one specific embodiment of the present invention, for determining the three-dimensional structure of the crystal, the diffraction pattern data may be obtained by using an x-ray image plate, and the phase information may be obtained by using the multiwavelength anomalous dispersion (MAD) method. Using the obtained x-ray diffraction pattern data and the phase information, the electron density map is prepared, and then the three-dimensional crystal structure may be obtained by drawing the atomic coordinates from the map.

In the method of collecting the diffraction pattern data using the x-ray, the method may be divided into a method obtained from a general laboratory (home source) and a method using a synchrotron radiation accelerator, according to a source of supply of the x-rays. Particularly, if the method using a synchrotron radiation accelerator is used, because small crystals of about 50 μm size may be measured and the data obtained from not only one wavelength but from various wavelengths may be collected, the crystal structure may be quickly determined. Therefore, preferred specific embodiments of the present invention may obtain the diffraction pattern data by using the synchrotron radiation accelerator, wherein the diffraction pattern data of the FabK protein according to the present invention is shown in following Table 1:

TABLE 1

| Space group of the crystal | C2 monoclinic system |
|---|---|
| Lattice unit | a = 65.797, b = 77.213, c = 59.230 Å, α = γ = 90° β = 99.994° |
| Data resolution | 2.3 Å |

The phase information may be obtained by using the multiple isomorphous replacement method, multiwavelength anomalous dispersion method, or molecular replacement method. In the preferred specific embodiments of the present invention, the phase information of the FabK crystal may be obtained by using the multiwavelength anomalous dispersion method (Modern x-ray Analysis on Single Crystals, Peter Luger). In more detail, the multiwavelength anomalous dispersion method is a method of calculating the phase using the anomalous diffraction pattern through 3 different wavelengths in the crystal of a protein having heavy metals. Using the multiwavelength anomalous dispersion method, the phase has to be calculated, and the calculation of an initial model according to the calculated phase has to be performed. The programs available for the calculation are not particularly limited, and any program that calculates the phase can be used. In the preferred specific embodiments of the present invention, a program such as SOLVE or RESOLVE (ROS Alamos Research Institute, USA) can be used. For performing a refinement process and a standardization process, a program such as CNS (Yale University) or CCP4 (Cambridge University) can be used.

The step of the refinement may be performed by improving the electron density coming from the x-ray data using O (Alwyn Jones) and COOT (Paul Emsly) programs to the computer monitor and modifying the structure to be most fitting. After performing the refinement step, it was clarified that the FabK protein structure according to the present invention includes FMN (flavin mononucleotide) and 24 water molecules, and may be expressed as an atomic model having the three-dimensional crystal structure as shown in following Table 2. In the development of an inhibiting agent targeting the FabK protein, the FabK protein may be used exclusively, or may be used in the form of a FabK-FMN complex. In the form of the complex, particularly, because the three-dimensional crystal structure of the FabK protein is excellent, the form of the complex is very useful for developing an inhibiting agent.

TABLE 2

Atomic coordinates on the three-dimensional crystal structure of the FabK-FMN complex having the amino acid sequences 2-312 of SEQ ID NO: 1

| A | B | C | D | E | F | G | H | I | J |
|---|---|---|---|---|---|---|---|---|---|
| ATOM | 1 | CB | THR | 2 | 1.718 | 10.119 | 42.330 | 1.00 | 76.78 |
| ATOM | 2 | OG1 | THR | 2 | 1.216 | 9.920 | 43.656 | 1.00 | 77.33 |
| ATOM | 3 | CG2 | THR | 2 | 0.826 | 9.379 | 41.346 | 1.00 | 74.62 |
| ATOM | 4 | C | THR | 2 | 3.742 | 10.004 | 40.886 | 1.00 | 78.22 |
| ATOM | 5 | O | THR | 2 | 4.668 | 9.365 | 40.376 | 1.00 | 78.67 |
| ATOM | 6 | N | THR | 2 | 4.004 | 10.139 | 43.345 | 1.00 | 71.47 |
| ATOM | 7 | CA | THR | 2 | 3.165 | 9.596 | 42.240 | 1.00 | 77.44 |
| ATOM | 8 | N | VAL | 3 | 3.186 | 11.073 | 40.316 | 1.00 | 76.84 |
| ATOM | 9 | CA | VAL | 3 | 3.616 | 11.601 | 39.020 | 1.00 | 75.22 |
| ATOM | 10 | CB | VAL | 3 | 2.611 | 12.658 | 38.481 | 1.00 | 74.12 |
| ATOM | 11 | CG1 | VAL | 3 | 2.316 | 13.689 | 39.557 | 1.00 | 74.99 |
| ATOM | 12 | CG2 | VAL | 3 | 3.181 | 13.344 | 37.242 | 1.00 | 72.96 |
| ATOM | 13 | C | VAL | 3 | 4.991 | 12.252 | 39.103 | 1.00 | 70.50 |
| ATOM | 14 | O | VAL | 3 | 5.250 | 13.068 | 39.984 | 1.00 | 72.91 |
| ATOM | 15 | N | ARG | 4 | 5.866 | 11.891 | 38.172 | 1.00 | 64.57 |
| ATOM | 16 | CA | ARG | 4 | 7.214 | 12.440 | 38.135 | 1.00 | 63.13 |
| ATOM | 17 | CB | ARG | 4 | 8.223 | 11.355 | 38.513 | 1.00 | 69.21 |
| ATOM | 18 | CG | ARG | 4 | 7.833 | 9.962 | 38.051 | 1.00 | 85.80 |
| ATOM | 19 | CD | ARG | 4 | 8.871 | 8.911 | 38.437 | 1.00 | 96.90 |
| ATOM | 20 | NE | ARG | 4 | 10.085 | 8.990 | 37.624 | 1.00 | 109.70 |
| ATOM | 21 | CZ | ARG | 4 | 11.041 | 9.904 | 37.771 | 1.00 | 114.16 |
| ATOM | 22 | NH1 | ARG | 4 | 10.943 | 10.835 | 38.711 | 1.00 | 118.45 |
| ATOM | 23 | NH2 | ARG | 4 | 12.099 | 9.888 | 36.970 | 1.00 | 115.05 |
| ATOM | 24 | C | ARG | 4 | 7.542 | 13.023 | 36.762 | 1.00 | 58.99 |
| ATOM | 25 | O | ARG | 4 | 7.239 | 12.424 | 35.729 | 1.00 | 50.86 |
| ATOM | 26 | N | THR | 5 | 8.170 | 14.194 | 36.753 | 1.00 | 51.26 |

TABLE 2-continued

Atomic coordinates on the three-dimensional crystal structure of the FabK-
FMN complex having the amino acid sequences 2-312 of SEQ ID NO: 1

| A | B | C | D | E | F | G | H | I | J |
|---|---|---|---|---|---|---|---|---|---|
| ATOM | 27 | CA | THR | 5 | 8.509 | 14.849 | 35.495 | 1.00 | 46.05 |
| ATOM | 28 | CB | THR | 5 | 7.634 | 16.087 | 35.269 | 1.00 | 50.25 |
| ATOM | 29 | OG1 | THR | 5 | 6.335 | 15.870 | 35.840 | 1.00 | 55.05 |
| ATOM | 30 | CG2 | THR | 5 | 7.493 | 16.359 | 33.777 | 1.00 | 59.53 |
| ATOM | 31 | C | THR | 5 | 9.946 | 15.317 | 35.507 | 1.00 | 38.81 |
| ATOM | 32 | O | THR | 5 | 10.615 | 15.236 | 36.533 | 1.00 | 35.76 |
| ATOM | 33 | N | ARG | 6 | 10.419 | 15.820 | 34.368 | 1.00 | 30.37 |
| ATOM | 34 | CA | ARG | 6 | 11.784 | 16.320 | 34.303 | 1.00 | 31.08 |
| ATOM | 35 | CB | ARG | 6 | 12.050 | 17.039 | 32.984 | 1.00 | 25.17 |
| ATOM | 36 | CG | ARG | 6 | 12.219 | 16.116 | 31.791 | 1.00 | 29.98 |
| ATOM | 37 | CD | ARG | 6 | 12.079 | 16.885 | 30.476 | 1.00 | 36.68 |
| ATOM | 38 | NE | ARG | 6 | 13.186 | 17.805 | 30.256 | 1.00 | 37.22 |
| ATOM | 39 | CZ | ARG | 6 | 13.163 | 18.830 | 29.410 | 1.00 | 34.87 |
| ATOM | 40 | NH1 | ARG | 6 | 12.080 | 19.095 | 28.690 | 1.00 | 29.29 |
| ATOM | 41 | NH2 | ARG | 6 | 14.241 | 19.586 | 29.275 | 1.00 | 43.28 |
| ATOM | 42 | C | ARG | 6 | 11.964 | 17.292 | 35.453 | 1.00 | 31.91 |
| ATOM | 43 | O | ARG | 6 | 13.016 | 17.333 | 36.080 | 1.00 | 35.47 |
| ATOM | 44 | N | VAL | 7 | 10.917 | 18.057 | 35.740 | 1.00 | 33.55 |
| ATOM | 45 | CA | VAL | 7 | 10.959 | 19.024 | 36.822 | 1.00 | 31.71 |
| ATOM | 46 | CB | VAL | 7 | 9.678 | 19.864 | 36.872 | 1.00 | 40.39 |
| ATOM | 47 | CG1 | VAL | 7 | 9.713 | 20.786 | 38.084 | 1.00 | 37.01 |
| ATOM | 48 | CG2 | VAL | 7 | 9.540 | 20.673 | 35.591 | 1.00 | 38.01 |
| ATOM | 49 | C | VAL | 7 | 11.163 | 18.392 | 38.192 | 1.00 | 33.22 |
| ATOM | 50 | O | VAL | 7 | 12.052 | 18.794 | 38.931 | 1.00 | 32.11 |
| ATOM | 51 | N | THR | 8 | 10.336 | 17.421 | 38.551 | 1.00 | 37.51 |
| ATOM | 52 | CA | THR | 8 | 10.492 | 16.780 | 39.851 | 1.00 | 43.86 |
| ATOM | 53 | CB | THR | 8 | 9.481 | 15.632 | 40.037 | 1.00 | 45.29 |
| ATOM | 54 | OG1 | THR | 8 | 9.661 | 14.660 | 38.997 | 1.00 | 44.08 |
| ATOM | 55 | CG2 | THR | 8 | 8.057 | 16.169 | 39.985 | 1.00 | 41.69 |
| ATOM | 56 | C | THR | 8 | 11.915 | 16.231 | 39.994 | 1.00 | 46.88 |
| ATOM | 57 | O | THR | 8 | 12.493 | 16.243 | 41.084 | 1.00 | 45.83 |
| ATOM | 58 | N | ASP | 9 | 12.479 | 15.770 | 38.880 | 1.00 | 47.56 |
| ATOM | 59 | CA | ASP | 9 | 13.830 | 15.220 | 38.867 | 1.00 | 48.98 |
| ATOM | 60 | CB | ASP | 9 | 14.087 | 14.486 | 37.551 | 1.00 | 54.05 |
| ATOM | 61 | CG | ASP | 9 | 13.137 | 13.333 | 37.333 | 1.00 | 63.51 |
| ATOM | 62 | OD1 | ASP | 9 | 13.173 | 12.733 | 36.236 | 1.00 | 70.34 |
| ATOM | 63 | OD2 | ASP | 9 | 12.358 | 13.026 | 38.261 | 1.00 | 68.35 |
| ATOM | 64 | C | ASP | 9 | 14.877 | 16.311 | 39.031 | 1.00 | 52.18 |
| ATOM | 65 | O | ASP | 9 | 15.735 | 16.241 | 39.913 | 1.00 | 53.25 |
| ATOM | 66 | N | LEU | 10 | 14.812 | 17.319 | 38.169 | 1.00 | 48.21 |
| ATOM | 67 | CA | LEU | 10 | 15.767 | 18.411 | 38.223 | 1.00 | 47.23 |
| ATOM | 68 | CB | LEU | 10 | 15.392 | 19.509 | 37.229 | 1.00 | 51.37 |
| ATOM | 69 | CG | LEU | 10 | 16.382 | 20.674 | 37.117 | 1.00 | 54.12 |
| ATOM | 70 | CD1 | LEU | 10 | 17.694 | 20.171 | 36.531 | 1.00 | 54.52 |
| ATOM | 71 | CD2 | LEU | 10 | 15.800 | 21.770 | 36.238 | 1.00 | 56.89 |
| ATOM | 72 | C | LEU | 10 | 15.843 | 19.015 | 39.610 | 1.00 | 44.90 |
| ATOM | 73 | O | LEU | 10 | 16.866 | 19.579 | 39.977 | 1.00 | 43.23 |
| ATOM | 74 | N | LEU | 11 | 14.763 | 18.900 | 40.379 | 1.00 | 41.34 |
| ATOM | 75 | CA | LEU | 11 | 14.734 | 19.471 | 41.723 | 1.00 | 43.54 |
| ATOM | 76 | CB | LEU | 11 | 13.607 | 20.502 | 41.837 | 1.00 | 39.34 |
| ATOM | 77 | CG | LEU | 11 | 13.785 | 21.894 | 41.218 | 1.00 | 45.50 |
| ATOM | 78 | CD1 | LEU | 11 | 14.219 | 21.798 | 39.753 | 1.00 | 46.71 |
| ATOM | 79 | CD2 | LEU | 11 | 12.468 | 22.646 | 41.352 | 1.00 | 36.77 |
| ATOM | 80 | C | LEU | 11 | 14.597 | 18.491 | 42.882 | 1.00 | 45.99 |
| ATOM | 81 | O | LEU | 11 | 14.517 | 18.928 | 44.033 | 1.00 | 44.74 |
| ATOM | 82 | N | GLU | 12 | 14.570 | 17.186 | 42.601 | 1.00 | 43.01 |
| ATOM | 83 | CA | GLU | 12 | 14.429 | 16.191 | 43.669 | 1.00 | 43.26 |
| ATOM | 84 | CB | GLU | 12 | 15.715 | 16.080 | 44.495 | 1.00 | 47.35 |
| ATOM | 85 | CG | GLU | 12 | 16.982 | 16.570 | 43.810 | 1.00 | 58.02 |
| ATOM | 86 | CD | GLU | 12 | 17.609 | 15.533 | 42.902 | 1.00 | 68.00 |
| ATOM | 87 | OE1 | GLU | 12 | 17.980 | 14.449 | 43.403 | 1.00 | 70.07 |
| ATOM | 88 | OE2 | GLU | 12 | 17.739 | 15.803 | 41.690 | 1.00 | 74.34 |
| ATOM | 89 | C | GLU | 12 | 13.333 | 16.750 | 44.564 | 1.00 | 42.63 |
| ATOM | 90 | O | GLU | 12 | 13.550 | 16.985 | 45.751 | 1.00 | 34.81 |
| ATOM | 91 | N | ILE | 13 | 12.159 | 16.983 | 43.994 | 1.00 | 44.15 |
| ATOM | 92 | CA | ILE | 13 | 11.085 | 17.573 | 44.772 | 1.00 | 49.47 |
| ATOM | 93 | CB | ILE | 13 | 10.486 | 18.776 | 43.990 | 1.00 | 51.04 |
| ATOM | 94 | CG2 | ILE | 13 | 10.063 | 18.341 | 42.597 | 1.00 | 49.47 |
| ATOM | 95 | CG1 | ILE | 13 | 9.327 | 19.388 | 44.764 | 1.00 | 56.66 |
| ATOM | 96 | CD1 | ILE | 13 | 8.649 | 20.493 | 44.016 | 1.00 | 55.92 |
| ATOM | 97 | C | ILE | 13 | 9.975 | 16.630 | 45.264 | 1.00 | 47.97 |
| ATOM | 98 | O | ILE | 13 | 9.687 | 16.608 | 46.463 | 1.00 | 53.32 |
| ATOM | 99 | N | GLU | 14 | 9.378 | 15.859 | 44.355 | 1.00 | 42.87 |
| ATOM | 100 | CA | GLU | 14 | 8.288 | 14.915 | 44.652 | 1.00 | 47.07 |

TABLE 2-continued

Atomic coordinates on the three-dimensional crystal structure of the FabK-FMN complex having the amino acid sequences 2-312 of SEQ ID NO: 1

| A | B | C | D | E | F | G | H | I | J |
|---|---|---|---|---|---|---|---|---|---|
| ATOM | 101 | CB | GLU | 14 | 7.957 | 14.841 | 46.144 | 1.00 | 48.25 |
| ATOM | 102 | CG | GLU | 14 | 6.805 | 13.899 | 46.445 | 1.00 | 67.00 |
| ATOM | 103 | CD | GLU | 14 | 6.571 | 13.708 | 47.927 | 1.00 | 82.21 |
| ATOM | 104 | OE1 | GLU | 14 | 6.324 | 14.713 | 48.626 | 1.00 | 87.48 |
| ATOM | 105 | OE2 | GLU | 14 | 6.631 | 12.551 | 48.395 | 1.00 | 88.12 |
| ATOM | 106 | C | GLU | 14 | 7.004 | 15.251 | 43.893 | 1.00 | 46.40 |
| ATOM | 107 | O | GLU | 14 | 6.407 | 14.376 | 43.276 | 1.00 | 46.85 |
| ATOM | 108 | N | HIS | 15 | 6.576 | 16.511 | 43.950 | 1.00 | 47.05 |
| ATOM | 109 | CA | HIS | 15 | 5.370 | 16.955 | 43.246 | 1.00 | 45.50 |
| ATOM | 110 | CB | HIS | 15 | 4.313 | 17.424 | 44.242 | 1.00 | 44.43 |
| ATOM | 111 | CG | HIS | 15 | 3.877 | 16.371 | 45.209 | 1.00 | 46.54 |
| ATOM | 112 | CD2 | HIS | 15 | 3.730 | 16.406 | 46.556 | 1.00 | 48.90 |
| ATOM | 113 | ND1 | HIS | 15 | 3.485 | 15.111 | 44.812 | 1.00 | 43.04 |
| ATOM | 114 | CE1 | HIS | 15 | 3.115 | 14.416 | 45.873 | 1.00 | 48.74 |
| ATOM | 115 | NE2 | HIS | 15 | 3.254 | 15.179 | 46.943 | 1.00 | 46.46 |
| ATOM | 116 | C | HIS | 15 | 5.704 | 18.118 | 42.304 | 1.00 | 46.97 |
| ATOM | 117 | O | HIS | 15 | 6.421 | 19.042 | 42.689 | 1.00 | 52.83 |
| ATOM | 118 | N | PRO | 16 | 5.182 | 18.094 | 41.062 | 1.00 | 44.41 |
| ATOM | 119 | CD | PRO | 16 | 4.403 | 17.040 | 40.396 | 1.00 | 46.81 |
| ATOM | 120 | CA | PRO | 16 | 5.472 | 19.184 | 40.122 | 1.00 | 43.13 |
| ATOM | 121 | CB | PRO | 16 | 4.997 | 18.627 | 38.772 | 1.00 | 42.08 |
| ATOM | 122 | CG | PRO | 16 | 4.916 | 17.135 | 38.993 | 1.00 | 47.19 |
| ATOM | 123 | C | PRO | 16 | 4.723 | 20.465 | 40.492 | 1.00 | 38.04 |
| ATOM | 124 | O | PRO | 16 | 3.964 | 20.997 | 39.682 | 1.00 | 43.06 |
| ATOM | 125 | N | ILE | 17 | 4.935 | 20.955 | 41.708 | 1.00 | 29.48 |
| ATOM | 126 | CA | ILE | 17 | 4.263 | 22.169 | 42.164 | 1.00 | 34.10 |
| ATOM | 127 | CB | ILE | 17 | 3.119 | 21.845 | 43.157 | 1.00 | 38.75 |
| ATOM | 128 | CG2 | ILE | 17 | 2.401 | 23.124 | 43.561 | 1.00 | 38.43 |
| ATOM | 129 | CG1 | ILE | 17 | 2.130 | 20.876 | 42.519 | 1.00 | 45.60 |
| ATOM | 130 | CD1 | ILE | 17 | 1.008 | 20.476 | 43.442 | 1.00 | 48.42 |
| ATOM | 131 | C | ILE | 17 | 5.199 | 23.152 | 42.862 | 1.00 | 29.93 |
| ATOM | 132 | O | ILE | 17 | 5.878 | 22.805 | 43.816 | 1.00 | 28.55 |
| ATOM | 133 | N | LEU | 18 | 5.226 | 24.387 | 42.388 | 1.00 | 35.59 |
| ATOM | 134 | CA | LEU | 18 | 6.069 | 25.392 | 43.016 | 1.00 | 36.21 |
| ATOM | 135 | CB | LEU | 18 | 6.990 | 26.063 | 41.995 | 1.00 | 35.84 |
| ATOM | 136 | CG | LEU | 18 | 7.773 | 25.217 | 40.991 | 1.00 | 38.51 |
| ATOM | 137 | CD1 | LEU | 18 | 8.873 | 26.091 | 40.411 | 1.00 | 34.03 |
| ATOM | 138 | CD2 | LEU | 18 | 8.360 | 23.983 | 41.650 | 1.00 | 40.91 |
| ATOM | 139 | C | LEU | 18 | 5.195 | 26.457 | 43.656 | 1.00 | 31.19 |
| ATOM | 140 | O | LEU | 18 | 4.021 | 26.586 | 43.333 | 1.00 | 30.43 |
| ATOM | 141 | N | MET | 19 | 5.784 | 27.206 | 44.574 | 1.00 | 33.22 |
| ATOM | 142 | CA | MET | 19 | 5.095 | 28.290 | 45.243 | 1.00 | 36.43 |
| ATOM | 143 | CB | MET | 19 | 5.237 | 28.149 | 46.750 | 1.00 | 28.38 |
| ATOM | 144 | CG | MET | 19 | 4.721 | 29.347 | 47.542 | 1.00 | 36.22 |
| ATOM | 145 | SD | MET | 19 | 5.226 | 29.329 | 49.284 | 1.00 | 28.82 |
| ATOM | 146 | CE | MET | 19 | 6.507 | 30.404 | 49.266 | 1.00 | 23.45 |
| ATOM | 147 | C | MET | 19 | 5.827 | 29.533 | 44.770 | 1.00 | 38.43 |
| ATOM | 148 | O | MET | 19 | 6.952 | 29.782 | 45.189 | 1.00 | 47.33 |
| ATOM | 149 | N | GLY | 20 | 5.205 | 30.301 | 43.885 | 1.00 | 28.76 |
| ATOM | 150 | CA | GLY | 20 | 5.853 | 31.499 | 43.382 | 1.00 | 34.33 |
| ATOM | 151 | C | GLY | 20 | 6.369 | 32.472 | 44.435 | 1.00 | 33.56 |
| ATOM | 152 | O | GLY | 20 | 5.738 | 32.670 | 45.481 | 1.00 | 38.91 |
| ATOM | 153 | N | GLY | 21 | 7.515 | 33.094 | 44.162 | 1.00 | 33.74 |
| ATOM | 154 | CA | GLY | 21 | 8.056 | 34.056 | 45.109 | 1.00 | 37.33 |
| ATOM | 155 | C | GLY | 21 | 7.046 | 35.174 | 45.309 | 1.00 | 33.31 |
| ATOM | 156 | O | GLY | 21 | 6.468 | 35.646 | 44.342 | 1.00 | 32.36 |
| ATOM | 157 | N | MET | 22 | 6.803 | 35.589 | 46.545 | 1.00 | 30.62 |
| ATOM | 158 | CA | MET | 22 | 5.835 | 36.655 | 46.777 | 1.00 | 29.82 |
| ATOM | 159 | CB | MET | 22 | 4.483 | 36.072 | 47.200 | 1.00 | 27.82 |
| ATOM | 160 | CG | MET | 22 | 3.770 | 35.307 | 46.095 | 1.00 | 16.61 |
| ATOM | 161 | SD | MET | 22 | 2.127 | 34.678 | 46.550 | 1.00 | 9.19 |
| ATOM | 162 | CE | MET | 22 | 2.695 | 33.290 | 47.700 | 1.00 | 16.11 |
| ATOM | 163 | C | MET | 22 | 6.313 | 37.653 | 47.813 | 1.00 | 34.96 |
| ATOM | 164 | O | MET | 22 | 6.379 | 37.342 | 48.996 | 1.00 | 35.83 |
| ATOM | 165 | N | ALA | 23 | 6.636 | 38.853 | 47.344 | 1.00 | 41.42 |
| ATOM | 166 | CA | ALA | 23 | 7.116 | 39.950 | 48.173 | 1.00 | 47.31 |
| ATOM | 167 | CB | ALA | 23 | 6.391 | 41.218 | 47.800 | 1.00 | 53.58 |
| ATOM | 168 | C | ALA | 23 | 7.033 | 39.749 | 49.678 | 1.00 | 53.56 |
| ATOM | 169 | O | ALA | 23 | 8.008 | 39.341 | 50.308 | 1.00 | 68.31 |
| ATOM | 170 | N | TRP | 24 | 5.872 | 40.041 | 50.256 | 1.00 | 49.74 |
| ATOM | 171 | CA | TRP | 24 | 5.695 | 39.919 | 51.702 | 1.00 | 49.67 |
| ATOM | 172 | CB | TRP | 24 | 4.934 | 41.131 | 52.251 | 1.00 | 53.69 |
| ATOM | 173 | CG | TRP | 24 | 5.581 | 42.455 | 51.969 | 1.00 | 58.95 |
| ATOM | 174 | CD2 | TRP | 24 | 6.597 | 43.098 | 52.750 | 1.00 | 61.60 |

TABLE 2-continued

Atomic coordinates on the three-dimensional crystal structure of the FabK-FMN complex having the amino acid sequences 2-312 of SEQ ID NO: 1

| A | B | C | D | E | F | G | H | I | J |
|---|---|---|---|---|---|---|---|---|---|
| ATOM | 175 | CE2 | TRP | 24 | 6.907 | 44.316 | 52.109 | 1.00 | 62.60 |
| ATOM | 176 | CE3 | TRP | 24 | 7.275 | 42.761 | 53.927 | 1.00 | 63.61 |
| ATOM | 177 | CD1 | TRP | 24 | 5.327 | 43.284 | 50.917 | 1.00 | 60.17 |
| ATOM | 178 | NE1 | TRP | 24 | 6.117 | 44.405 | 50.994 | 1.00 | 62.36 |
| ATOM | 179 | CZ2 | TRP | 24 | 7.866 | 45.199 | 52.605 | 1.00 | 62.84 |
| ATOM | 180 | CZ3 | TRP | 24 | 8.231 | 43.640 | 54.422 | 1.00 | 67.42 |
| ATOM | 181 | CH2 | TRP | 24 | 8.516 | 44.846 | 53.759 | 1.00 | 66.69 |
| ATOM | 182 | C | TRP | 24 | 4.975 | 38.661 | 52.166 | 1.00 | 51.32 |
| ATOM | 183 | O | TRP | 24 | 4.992 | 38.336 | 53.355 | 1.00 | 51.79 |
| ATOM | 184 | N | ALA | 25 | 4.350 | 37.958 | 51.228 | 1.00 | 49.82 |
| ATOM | 185 | CA | ALA | 25 | 3.591 | 36.754 | 51.534 | 1.00 | 45.71 |
| ATOM | 186 | CB | ALA | 25 | 2.393 | 36.665 | 50.603 | 1.00 | 48.79 |
| ATOM | 187 | C | ALA | 25 | 4.404 | 35.467 | 51.457 | 1.00 | 44.45 |
| ATOM | 188 | O | ALA | 25 | 3.976 | 34.423 | 51.964 | 1.00 | 41.92 |
| ATOM | 189 | N | GLY | 26 | 5.566 | 35.536 | 50.822 | 1.00 | 42.87 |
| ATOM | 190 | CA | GLY | 26 | 6.405 | 34.355 | 50.703 | 1.00 | 48.73 |
| ATOM | 191 | C | GLY | 26 | 7.218 | 34.086 | 51.960 | 1.00 | 44.98 |
| ATOM | 192 | O | GLY | 26 | 8.445 | 34.020 | 51.909 | 1.00 | 46.38 |
| ATOM | 193 | N | THR | 27 | 6.528 | 33.920 | 53.086 | 1.00 | 46.78 |
| ATOM | 194 | CA | THR | 27 | 7.176 | 33.675 | 54.375 | 1.00 | 46.23 |
| ATOM | 195 | CB | THR | 27 | 6.177 | 33.818 | 55.534 | 1.00 | 48.50 |
| ATOM | 196 | OG1 | THR | 27 | 5.241 | 32.731 | 55.498 | 1.00 | 50.76 |
| ATOM | 197 | CG2 | THR | 27 | 5.424 | 35.136 | 55.421 | 1.00 | 48.06 |
| ATOM | 198 | C | THR | 27 | 7.820 | 32.299 | 54.491 | 1.00 | 45.90 |
| ATOM | 199 | O | THR | 27 | 7.374 | 31.327 | 53.873 | 1.00 | 45.28 |
| ATOM | 200 | N | PRO | 28 | 8.889 | 32.201 | 55.295 | 1.00 | 48.12 |
| ATOM | 201 | CD | PRO | 28 | 9.547 | 33.295 | 56.035 | 1.00 | 45.95 |
| ATOM | 202 | CA | PRO | 28 | 9.597 | 30.934 | 55.496 | 1.00 | 44.96 |
| ATOM | 203 | CB | PRO | 28 | 10.643 | 31.292 | 56.546 | 1.00 | 46.21 |
| ATOM | 204 | CG | PRO | 28 | 10.933 | 32.738 | 56.256 | 1.00 | 46.30 |
| ATOM | 205 | C | PRO | 28 | 8.636 | 29.862 | 55.993 | 1.00 | 44.58 |
| ATOM | 206 | O | PRO | 28 | 8.759 | 28.688 | 55.655 | 1.00 | 47.59 |
| ATOM | 207 | N | THR | 29 | 7.671 | 30.286 | 56.796 | 1.00 | 41.72 |
| ATOM | 208 | CA | THR | 29 | 6.688 | 29.378 | 57.354 | 1.00 | 42.65 |
| ATOM | 209 | CB | THR | 29 | 5.818 | 30.108 | 58.381 | 1.00 | 48.52 |
| ATOM | 210 | OG1 | THR | 29 | 6.623 | 31.056 | 59.090 | 1.00 | 52.69 |
| ATOM | 211 | CG2 | THR | 29 | 5.234 | 29.122 | 59.375 | 1.00 | 57.21 |
| ATOM | 212 | C | THR | 29 | 5.803 | 28.815 | 56.244 | 1.00 | 42.85 |
| ATOM | 213 | O | THR | 29 | 5.514 | 27.615 | 56.209 | 1.00 | 44.09 |
| ATOM | 214 | N | LEU | 30 | 5.373 | 29.680 | 55.331 | 1.00 | 36.16 |
| ATOM | 215 | CA | LEU | 30 | 4.531 | 29.230 | 54.233 | 1.00 | 31.75 |
| ATOM | 216 | CB | LEU | 30 | 3.922 | 30.421 | 53.506 | 1.00 | 36.10 |
| ATOM | 217 | CG | LEU | 30 | 3.153 | 30.098 | 52.221 | 1.00 | 38.23 |
| ATOM | 218 | CD1 | LEU | 30 | 2.097 | 29.040 | 52.491 | 1.00 | 44.84 |
| ATOM | 219 | CD2 | LEU | 30 | 2.513 | 31.365 | 51.695 | 1.00 | 44.15 |
| ATOM | 220 | C | LEU | 30 | 5.345 | 28.391 | 53.257 | 1.00 | 32.20 |
| ATOM | 221 | O | LEU | 30 | 4.890 | 27.350 | 52.788 | 1.00 | 31.64 |
| ATOM | 222 | N | ALA | 31 | 6.550 | 28.851 | 52.949 | 1.00 | 30.70 |
| ATOM | 223 | CA | ALA | 31 | 7.404 | 28.113 | 52.035 | 1.00 | 34.14 |
| ATOM | 224 | CB | ALA | 31 | 8.689 | 28.908 | 51.743 | 1.00 | 27.81 |
| ATOM | 225 | C | ALA | 31 | 7.740 | 26.787 | 52.706 | 1.00 | 34.45 |
| ATOM | 226 | O | ALA | 31 | 7.866 | 25.757 | 52.051 | 1.00 | 37.83 |
| ATOM | 227 | N | ALA | 32 | 7.873 | 26.819 | 54.024 | 1.00 | 31.01 |
| ATOM | 228 | CA | ALA | 32 | 8.203 | 25.618 | 54.772 | 1.00 | 38.14 |
| ATOM | 229 | CB | ALA | 32 | 8.351 | 25.949 | 56.248 | 1.00 | 37.14 |
| ATOM | 230 | C | ALA | 32 | 7.132 | 24.556 | 54.576 | 1.00 | 35.20 |
| ATOM | 231 | O | ALA | 32 | 7.434 | 23.417 | 54.231 | 1.00 | 40.16 |
| ATOM | 232 | N | ALA | 33 | 5.881 | 24.941 | 54.792 | 1.00 | 34.68 |
| ATOM | 233 | CA | ALA | 33 | 4.763 | 24.019 | 54.642 | 1.00 | 38.86 |
| ATOM | 234 | CB | ALA | 33 | 3.459 | 24.737 | 54.950 | 1.00 | 38.66 |
| ATOM | 235 | C | ALA | 33 | 4.694 | 23.390 | 53.250 | 1.00 | 35.62 |
| ATOM | 236 | O | ALA | 33 | 4.443 | 22.194 | 53.109 | 1.00 | 38.77 |
| ATOM | 237 | N | VAL | 34 | 4.919 | 24.199 | 52.222 | 1.00 | 35.59 |
| ATOM | 238 | CA | VAL | 34 | 4.861 | 23.706 | 50.857 | 1.00 | 33.18 |
| ATOM | 239 | CB | VAL | 34 | 4.985 | 24.881 | 49.842 | 1.00 | 30.34 |
| ATOM | 240 | CG1 | VAL | 34 | 5.009 | 24.346 | 48.414 | 1.00 | 26.85 |
| ATOM | 241 | CG2 | VAL | 34 | 3.823 | 25.839 | 50.019 | 1.00 | 30.61 |
| ATOM | 242 | C | VAL | 34 | 5.942 | 22.651 | 50.590 | 1.00 | 35.06 |
| ATOM | 243 | O | VAL | 34 | 5.665 | 21.602 | 50.006 | 1.00 | 32.23 |
| ATOM | 244 | N | SER | 35 | 7.170 | 22.922 | 51.018 | 1.00 | 37.64 |
| ATOM | 245 | CA | SER | 35 | 8.251 | 21.963 | 50.805 | 1.00 | 42.39 |
| ATOM | 246 | CB | SER | 35 | 9.605 | 22.584 | 51.161 | 1.00 | 37.71 |
| ATOM | 247 | OG | SER | 35 | 10.050 | 23.477 | 50.147 | 1.00 | 40.15 |
| ATOM | 248 | C | SER | 35 | 8.041 | 20.683 | 51.614 | 1.00 | 42.52 |

TABLE 2-continued

Atomic coordinates on the three-dimensional crystal structure of the FabK-
FMN complex having the amino acid sequences 2-312 of SEQ ID NO: 1

| A | B | C | D | E | F | G | H | I | J |
|---|---|---|---|---|---|---|---|---|---|
| ATOM | 249 | O | SER | 35 | 8.383 | 19.588 | 51.152 | 1.00 | 38.66 |
| ATOM | 250 | N | GLU | 36 | 7.483 | 20.818 | 52.817 | 1.00 | 40.23 |
| ATOM | 251 | CA | GLU | 36 | 7.235 | 19.647 | 53.646 | 1.00 | 39.04 |
| ATOM | 252 | CB | GLU | 36 | 6.693 | 20.033 | 55.021 | 1.00 | 39.65 |
| ATOM | 253 | CG | GLU | 36 | 7.768 | 20.385 | 56.045 | 1.00 | 50.54 |
| ATOM | 254 | CD | GLU | 36 | 8.773 | 19.254 | 56.305 | 1.00 | 56.57 |
| ATOM | 255 | OE1 | GLU | 36 | 9.497 | 19.333 | 57.323 | 1.00 | 56.90 |
| ATOM | 256 | OE2 | GLU | 36 | 8.855 | 18.296 | 55.500 | 1.00 | 59.08 |
| ATOM | 257 | C | GLU | 36 | 6.223 | 18.789 | 52.934 | 1.00 | 39.46 |
| ATOM | 258 | O | GLU | 36 | 6.336 | 17.566 | 52.925 | 1.00 | 42.82 |
| ATOM | 259 | N | ALA | 37 | 5.245 | 19.448 | 52.321 | 1.00 | 32.30 |
| ATOM | 260 | CA | ALA | 37 | 4.191 | 18.767 | 51.584 | 1.00 | 35.62 |
| ATOM | 261 | CB | ALA | 37 | 3.065 | 19.738 | 51.279 | 1.00 | 30.04 |
| ATOM | 262 | C | ALA | 37 | 4.681 | 18.129 | 50.287 | 1.00 | 36.08 |
| ATOM | 263 | O | ALA | 37 | 3.878 | 17.685 | 49.466 | 1.00 | 41.44 |
| ATOM | 264 | N | GLY | 38 | 5.991 | 18.090 | 50.087 | 1.00 | 40.96 |
| ATOM | 265 | CA | GLY | 38 | 6.516 | 17.483 | 48.875 | 1.00 | 40.94 |
| ATOM | 266 | C | GLY | 38 | 6.573 | 18.436 | 47.698 | 1.00 | 39.61 |
| ATOM | 267 | O | GLY | 38 | 7.044 | 18.075 | 46.622 | 1.00 | 36.13 |
| ATOM | 268 | N | GLY | 39 | 6.079 | 19.652 | 47.893 | 1.00 | 34.73 |
| ATOM | 269 | CA | GLY | 39 | 6.119 | 20.628 | 46.821 | 1.00 | 38.29 |
| ATOM | 270 | C | GLY | 39 | 7.420 | 21.393 | 46.958 | 1.00 | 40.52 |
| ATOM | 271 | O | GLY | 39 | 8.348 | 20.918 | 47.613 | 1.00 | 42.28 |
| ATOM | 272 | N | LEU | 40 | 7.497 | 22.573 | 46.354 | 1.00 | 40.15 |
| ATOM | 273 | CA | LEU | 40 | 8.708 | 23.380 | 46.443 | 1.00 | 39.04 |
| ATOM | 274 | CB | LEU | 40 | 9.429 | 23.433 | 45.098 | 1.00 | 28.82 |
| ATOM | 275 | CG | LEU | 40 | 10.692 | 24.290 | 45.169 | 1.00 | 30.24 |
| ATOM | 276 | CD1 | LEU | 40 | 11.835 | 23.483 | 45.745 | 1.00 | 24.21 |
| ATOM | 277 | CD2 | LEU | 40 | 11.055 | 24.800 | 43.804 | 1.00 | 32.86 |
| ATOM | 278 | C | LEU | 40 | 8.393 | 24.797 | 46.883 | 1.00 | 35.14 |
| ATOM | 279 | O | LEU | 40 | 8.154 | 25.670 | 46.049 | 1.00 | 34.65 |
| ATOM | 280 | N | GLY | 41 | 8.379 | 25.024 | 48.192 | 1.00 | 30.27 |
| ATOM | 281 | CA | GLY | 41 | 8.109 | 26.360 | 48.690 | 1.00 | 33.52 |
| ATOM | 282 | C | GLY | 41 | 9.259 | 27.272 | 48.292 | 1.00 | 30.70 |
| ATOM | 283 | O | GLY | 41 | 10.378 | 26.799 | 48.107 | 1.00 | 28.53 |
| ATOM | 284 | N | ILE | 42 | 8.997 | 28.569 | 48.146 | 1.00 | 30.94 |
| ATOM | 285 | CA | ILE | 42 | 10.045 | 29.518 | 47.757 | 1.00 | 29.02 |
| ATOM | 286 | CB | ILE | 42 | 10.017 | 29.808 | 46.240 | 1.00 | 27.09 |
| ATOM | 287 | CG2 | ILE | 42 | 10.960 | 30.968 | 45.908 | 1.00 | 27.21 |
| ATOM | 288 | CG1 | ILE | 42 | 10.418 | 28.561 | 45.462 | 1.00 | 23.74 |
| ATOM | 289 | CD1 | ILE | 42 | 10.354 | 28.754 | 43.969 | 1.00 | 36.00 |
| ATOM | 290 | C | ILE | 42 | 9.928 | 30.844 | 48.480 | 1.00 | 29.00 |
| ATOM | 291 | O | ILE | 42 | 8.875 | 31.469 | 48.466 | 1.00 | 30.31 |
| ATOM | 292 | N | ILE | 43 | 11.020 | 31.279 | 49.100 | 1.00 | 30.42 |
| ATOM | 293 | CA | ILE | 43 | 11.024 | 32.547 | 49.829 | 1.00 | 32.61 |
| ATOM | 294 | CB | ILE | 43 | 12.252 | 32.677 | 50.762 | 1.00 | 36.97 |
| ATOM | 295 | CG2 | ILE | 43 | 12.050 | 33.850 | 51.722 | 1.00 | 39.55 |
| ATOM | 296 | CG1 | ILE | 43 | 12.468 | 31.387 | 51.547 | 1.00 | 39.68 |
| ATOM | 297 | CD1 | ILE | 43 | 13.730 | 31.397 | 52.371 | 1.00 | 31.95 |
| ATOM | 298 | C | ILE | 43 | 11.075 | 33.727 | 48.864 | 1.00 | 32.86 |
| ATOM | 299 | O | ILE | 43 | 11.901 | 33.760 | 47.944 | 1.00 | 27.20 |
| ATOM | 300 | N | GLY | 44 | 10.192 | 34.696 | 49.081 | 1.00 | 32.20 |
| ATOM | 301 | CA | GLY | 44 | 10.182 | 35.874 | 48.240 | 1.00 | 29.77 |
| ATOM | 302 | C | GLY | 44 | 10.922 | 37.018 | 48.907 | 1.00 | 32.82 |
| ATOM | 303 | O | GLY | 44 | 10.501 | 37.520 | 49.947 | 1.00 | 35.60 |
| ATOM | 304 | N | SER | 45 | 12.040 | 37.429 | 48.326 | 1.00 | 34.76 |
| ATOM | 305 | CA | SER | 45 | 12.788 | 38.541 | 48.889 | 1.00 | 40.69 |
| ATOM | 306 | CB | SER | 45 | 14.286 | 38.353 | 48.632 | 1.00 | 38.90 |
| ATOM | 307 | OG | SER | 45 | 14.581 | 38.343 | 47.246 | 1.00 | 42.21 |
| ATOM | 308 | C | SER | 45 | 12.291 | 39.843 | 48.250 | 1.00 | 44.71 |
| ATOM | 309 | O | SER | 45 | 12.908 | 40.373 | 47.328 | 1.00 | 49.25 |
| ATOM | 310 | N | GLY | 46 | 11.156 | 40.344 | 48.731 | 1.00 | 49.42 |
| ATOM | 311 | CA | GLY | 46 | 10.610 | 41.578 | 48.191 | 1.00 | 48.23 |
| ATOM | 312 | C | GLY | 46 | 11.405 | 42.766 | 48.695 | 1.00 | 48.90 |
| ATOM | 313 | O | GLY | 46 | 12.452 | 43.100 | 48.144 | 1.00 | 47.59 |
| ATOM | 314 | N | ALA | 47 | 10.903 | 43.420 | 49.733 | 1.00 | 50.78 |
| ATOM | 315 | CA | ALA | 47 | 11.615 | 44.544 | 50.317 | 1.00 | 57.88 |
| ATOM | 316 | CB | ALA | 47 | 10.636 | 45.552 | 50.902 | 1.00 | 61.50 |
| ATOM | 317 | C | ALA | 47 | 12.447 | 43.896 | 51.417 | 1.00 | 59.13 |
| ATOM | 318 | O | ALA | 47 | 12.369 | 44.261 | 52.594 | 1.00 | 63.02 |
| ATOM | 319 | N | MET | 48 | 13.243 | 42.915 | 51.010 | 1.00 | 55.09 |
| ATOM | 320 | CA | MET | 48 | 14.069 | 42.163 | 51.936 | 1.00 | 50.91 |
| ATOM | 321 | CB | MET | 48 | 13.793 | 40.664 | 51.739 | 1.00 | 48.02 |
| ATOM | 322 | CG | MET | 48 | 14.157 | 39.791 | 52.912 | 1.00 | 43.23 |

TABLE 2-continued

Atomic coordinates on the three-dimensional crystal structure of the FabK-FMN complex having the amino acid sequences 2-312 of SEQ ID NO: 1

| A | B | C | D | E | F | G | H | I | J |
|---|---|---|---|---|---|---|---|---|---|
| ATOM | 323 | SD | MET | 48 | 13.803 | 38.008 | 52.712 | 1.00 | 35.61 |
| ATOM | 324 | CE | MET | 48 | 12.376 | 37.852 | 53.720 | 1.00 | 38.53 |
| ATOM | 325 | C | MET | 48 | 15.538 | 42.485 | 51.686 | 1.00 | 50.54 |
| ATOM | 326 | O | MET | 48 | 15.983 | 42.536 | 50.534 | 1.00 | 46.18 |
| ATOM | 327 | N | LYS | 49 | 16.279 | 42.728 | 52.767 | 1.00 | 45.87 |
| ATOM | 328 | CA | LYS | 49 | 17.704 | 43.032 | 52.674 | 1.00 | 44.78 |
| ATOM | 329 | CB | LYS | 49 | 18.075 | 44.172 | 53.626 | 1.00 | 50.83 |
| ATOM | 330 | CG | LYS | 49 | 17.627 | 43.970 | 55.053 | 1.00 | 63.45 |
| ATOM | 331 | CD | LYS | 49 | 17.551 | 45.297 | 55.792 | 1.00 | 72.94 |
| ATOM | 332 | CE | LYS | 49 | 16.543 | 46.239 | 55.133 | 1.00 | 79.15 |
| ATOM | 333 | NZ | LYS | 49 | 15.169 | 45.654 | 55.046 | 1.00 | 84.18 |
| ATOM | 334 | C | LYS | 49 | 18.504 | 41.776 | 52.990 | 1.00 | 39.08 |
| ATOM | 335 | O | LYS | 49 | 18.000 | 40.862 | 53.634 | 1.00 | 39.23 |
| ATOM | 336 | N | PRO | 50 | 19.767 | 41.722 | 52.542 | 1.00 | 36.52 |
| ATOM | 337 | CD | PRO | 50 | 20.518 | 42.866 | 51.999 | 1.00 | 39.27 |
| ATOM | 338 | CA | PRO | 50 | 20.667 | 40.584 | 52.746 | 1.00 | 36.95 |
| ATOM | 339 | CB | PRO | 50 | 22.038 | 41.188 | 52.475 | 1.00 | 36.02 |
| ATOM | 340 | CG | PRO | 50 | 21.749 | 42.199 | 51.439 | 1.00 | 33.04 |
| ATOM | 341 | C | PRO | 50 | 20.589 | 39.899 | 54.109 | 1.00 | 39.30 |
| ATOM | 342 | O | PRO | 50 | 20.458 | 38.681 | 54.186 | 1.00 | 42.26 |
| ATOM | 343 | N | ASP | 51 | 20.685 | 40.666 | 55.186 | 1.00 | 43.71 |
| ATOM | 344 | CA | ASP | 51 | 20.612 | 40.054 | 56.499 | 1.00 | 48.73 |
| ATOM | 345 | CB | ASP | 51 | 20.908 | 41.083 | 57.595 | 1.00 | 60.38 |
| ATOM | 346 | CG | ASP | 51 | 20.078 | 42.344 | 57.454 | 1.00 | 72.72 |
| ATOM | 347 | OD1 | ASP | 51 | 18.841 | 42.263 | 57.607 | 1.00 | 77.61 |
| ATOM | 348 | OD2 | ASP | 51 | 20.665 | 43.419 | 57.191 | 1.00 | 73.69 |
| ATOM | 349 | C | ASP | 51 | 19.224 | 39.454 | 56.662 | 1.00 | 46.17 |
| ATOM | 350 | O | ASP | 51 | 19.075 | 38.342 | 57.167 | 1.00 | 43.73 |
| ATOM | 351 | N | ASP | 52 | 18.213 | 40.185 | 56.203 | 1.00 | 40.71 |
| ATOM | 352 | CA | ASP | 52 | 16.832 | 39.722 | 56.281 | 1.00 | 40.51 |
| ATOM | 353 | CB | ASP | 52 | 15.889 | 40.713 | 55.580 | 1.00 | 40.63 |
| ATOM | 354 | CG | ASP | 52 | 15.649 | 41.984 | 56.393 | 1.00 | 49.15 |
| ATOM | 355 | OD1 | ASP | 52 | 14.819 | 42.822 | 55.966 | 1.00 | 52.28 |
| ATOM | 356 | OD2 | ASP | 52 | 16.285 | 42.150 | 57.455 | 1.00 | 50.89 |
| ATOM | 357 | C | ASP | 52 | 16.683 | 38.349 | 55.629 | 1.00 | 38.69 |
| ATOM | 358 | O | ASP | 52 | 16.074 | 37.438 | 56.198 | 1.00 | 35.85 |
| ATOM | 359 | N | LEU | 53 | 17.240 | 38.205 | 54.432 | 1.00 | 32.16 |
| ATOM | 360 | CA | LEU | 53 | 17.146 | 36.943 | 53.706 | 1.00 | 35.79 |
| ATOM | 361 | CB | LEU | 53 | 17.695 | 37.091 | 52.286 | 1.00 | 40.13 |
| ATOM | 362 | CG | LEU | 53 | 17.505 | 35.848 | 51.403 | 1.00 | 46.73 |
| ATOM | 363 | CD1 | LEU | 53 | 16.010 | 35.619 | 51.204 | 1.00 | 38.33 |
| ATOM | 364 | CD2 | LEU | 53 | 18.214 | 36.020 | 50.057 | 1.00 | 36.36 |
| ATOM | 365 | C | LEU | 53 | 17.914 | 35.858 | 54.424 | 1.00 | 35.48 |
| ATOM | 366 | O | LEU | 53 | 17.430 | 34.733 | 54.588 | 1.00 | 34.50 |
| ATOM | 367 | N | ARG | 54 | 19.124 | 36.200 | 54.850 | 1.00 | 35.52 |
| ATOM | 368 | CA | ARG | 54 | 19.962 | 35.252 | 55.563 | 1.00 | 33.99 |
| ATOM | 369 | CB | ARG | 54 | 21.231 | 35.942 | 56.054 | 1.00 | 35.07 |
| ATOM | 370 | CG | ARG | 54 | 22.243 | 35.012 | 56.683 | 1.00 | 41.70 |
| ATOM | 371 | CD | ARG | 54 | 23.604 | 35.679 | 56.768 | 1.00 | 50.68 |
| ATOM | 372 | NE | ARG | 54 | 24.373 | 35.537 | 55.533 | 1.00 | 46.86 |
| ATOM | 373 | CZ | ARG | 54 | 24.927 | 36.550 | 54.873 | 1.00 | 51.99 |
| ATOM | 374 | NH1 | ARG | 54 | 24.794 | 37.796 | 55.321 | 1.00 | 51.32 |
| ATOM | 375 | NH2 | ARG | 54 | 25.635 | 36.316 | 53.778 | 1.00 | 46.75 |
| ATOM | 376 | C | ARG | 54 | 19.190 | 34.674 | 56.744 | 1.00 | 35.28 |
| ATOM | 377 | O | ARG | 54 | 19.116 | 33.455 | 56.916 | 1.00 | 36.87 |
| ATOM | 378 | N | LYS | 55 | 18.609 | 35.545 | 57.559 | 1.00 | 33.44 |
| ATOM | 379 | CA | LYS | 55 | 17.856 | 35.062 | 58.701 | 1.00 | 36.50 |
| ATOM | 380 | CB | LYS | 55 | 17.137 | 36.204 | 59.424 | 1.00 | 40.15 |
| ATOM | 381 | CG | LYS | 55 | 16.461 | 35.736 | 60.715 | 1.00 | 40.78 |
| ATOM | 382 | CD | LYS | 55 | 15.437 | 36.714 | 61.233 | 1.00 | 45.23 |
| ATOM | 383 | CE | LYS | 55 | 16.044 | 38.071 | 61.489 | 1.00 | 41.58 |
| ATOM | 384 | NZ | LYS | 55 | 15.002 | 39.037 | 61.909 | 1.00 | 54.39 |
| ATOM | 385 | C | LYS | 55 | 16.807 | 34.077 | 58.221 | 1.00 | 37.88 |
| ATOM | 386 | O | LYS | 55 | 16.744 | 32.937 | 58.688 | 1.00 | 38.02 |
| ATOM | 387 | N | ALA | 56 | 15.990 | 34.553 | 57.282 | 1.00 | 29.58 |
| ATOM | 388 | CA | ALA | 56 | 14.886 | 33.809 | 56.709 | 1.00 | 23.86 |
| ATOM | 389 | CB | ALA | 56 | 14.199 | 34.652 | 55.671 | 1.00 | 30.02 |
| ATOM | 390 | C | ALA | 56 | 15.271 | 32.477 | 56.110 | 1.00 | 29.75 |
| ATOM | 391 | O | ALA | 56 | 14.557 | 31.488 | 56.289 | 1.00 | 33.44 |
| ATOM | 392 | N | ILE | 57 | 16.382 | 32.438 | 55.385 | 1.00 | 29.78 |
| ATOM | 393 | CA | ILE | 57 | 16.815 | 31.182 | 54.783 | 1.00 | 35.07 |
| ATOM | 394 | CB | ILE | 57 | 18.113 | 31.382 | 53.978 | 1.00 | 34.85 |
| ATOM | 395 | CG2 | ILE | 57 | 18.810 | 30.048 | 53.765 | 1.00 | 35.22 |
| ATOM | 396 | CG1 | ILE | 57 | 17.786 | 32.079 | 52.648 | 1.00 | 31.11 |

TABLE 2-continued

Atomic coordinates on the three-dimensional crystal structure of the FabK-
FMN complex having the amino acid sequences 2-312 of SEQ ID NO: 1

| A | B | C | D | E | F | G | H | I | J |
|---|---|---|---|---|---|---|---|---|---|
| ATOM | 397 | CD1 | ILE | 57 | 18.995 | 32.411 | 51.781 | 1.00 | 32.90 |
| ATOM | 398 | C | ILE | 57 | 17.038 | 30.153 | 55.889 | 1.00 | 40.99 |
| ATOM | 399 | O | ILE | 57 | 16.461 | 29.057 | 55.881 | 1.00 | 41.38 |
| ATOM | 400 | N | SER | 58 | 17.864 | 30.530 | 56.855 | 1.00 | 45.86 |
| ATOM | 401 | CA | SER | 58 | 18.179 | 29.678 | 57.989 | 1.00 | 47.36 |
| ATOM | 402 | CB | SER | 58 | 19.147 | 30.411 | 58.924 | 1.00 | 50.23 |
| ATOM | 403 | OG | SER | 58 | 19.566 | 29.576 | 59.987 | 1.00 | 63.05 |
| ATOM | 404 | C | SER | 58 | 16.931 | 29.242 | 58.768 | 1.00 | 46.03 |
| ATOM | 405 | O | SER | 58 | 16.812 | 28.076 | 59.136 | 1.00 | 42.29 |
| ATOM | 406 | N | GLU | 59 | 16.002 | 30.169 | 59.012 | 1.00 | 47.09 |
| ATOM | 407 | CA | GLU | 59 | 14.796 | 29.839 | 59.772 | 1.00 | 48.31 |
| ATOM | 408 | CB | GLU | 59 | 14.045 | 31.112 | 60.185 | 1.00 | 49.39 |
| ATOM | 409 | CG | GLU | 59 | 13.272 | 31.808 | 59.083 | 1.00 | 70.71 |
| ATOM | 410 | CD | GLU | 59 | 12.355 | 32.902 | 59.625 | 1.00 | 81.53 |
| ATOM | 411 | OE1 | GLU | 59 | 12.867 | 33.897 | 60.188 | 1.00 | 86.75 |
| ATOM | 412 | OE2 | GLU | 59 | 11.118 | 32.766 | 59.495 | 1.00 | 86.05 |
| ATOM | 413 | C | GLU | 59 | 13.854 | 28.885 | 59.034 | 1.00 | 48.27 |
| ATOM | 414 | O | GLU | 59 | 12.965 | 28.280 | 59.641 | 1.00 | 42.87 |
| ATOM | 415 | N | LEU | 60 | 14.047 | 28.749 | 57.726 | 1.00 | 44.01 |
| ATOM | 416 | CA | LEU | 60 | 13.216 | 27.841 | 56.957 | 1.00 | 45.27 |
| ATOM | 417 | CB | LEU | 60 | 13.112 | 28.288 | 55.489 | 1.00 | 39.70 |
| ATOM | 418 | CG | LEU | 60 | 12.471 | 27.252 | 54.554 | 1.00 | 40.96 |
| ATOM | 419 | CD1 | LEU | 60 | 11.794 | 27.932 | 53.386 | 1.00 | 41.85 |
| ATOM | 420 | CD2 | LEU | 60 | 13.529 | 26.285 | 54.069 | 1.00 | 38.78 |
| ATOM | 421 | C | LEU | 60 | 13.854 | 26.464 | 57.050 | 1.00 | 45.62 |
| ATOM | 422 | O | LEU | 60 | 13.163 | 25.449 | 57.182 | 1.00 | 47.89 |
| ATOM | 423 | N | ARG | 61 | 15.180 | 26.437 | 56.987 | 1.00 | 43.97 |
| ATOM | 424 | CA | ARG | 61 | 15.910 | 25.182 | 57.074 | 1.00 | 46.45 |
| ATOM | 425 | CB | ARG | 61 | 17.396 | 25.425 | 56.804 | 1.00 | 41.00 |
| ATOM | 426 | CG | ARG | 61 | 17.729 | 25.431 | 55.320 | 1.00 | 42.28 |
| ATOM | 427 | CD | ARG | 61 | 19.146 | 25.876 | 55.034 | 1.00 | 39.26 |
| ATOM | 428 | NE | ARG | 61 | 19.530 | 25.535 | 53.666 | 1.00 | 40.42 |
| ATOM | 429 | CZ | ARG | 61 | 20.566 | 26.064 | 53.020 | 1.00 | 43.19 |
| ATOM | 430 | NH1 | ARG | 61 | 21.328 | 26.971 | 53.624 | 1.00 | 42.50 |
| ATOM | 431 | NH2 | ARG | 61 | 20.839 | 25.688 | 51.773 | 1.00 | 37.56 |
| ATOM | 432 | C | ARG | 61 | 15.709 | 24.536 | 58.444 | 1.00 | 51.33 |
| ATOM | 433 | O | ARG | 61 | 16.000 | 23.354 | 58.639 | 1.00 | 51.73 |
| ATOM | 434 | N | GLN | 62 | 15.198 | 25.321 | 59.384 | 1.00 | 52.54 |
| ATOM | 435 | CA | GLN | 62 | 14.937 | 24.840 | 60.732 | 1.00 | 55.58 |
| ATOM | 436 | CB | GLN | 62 | 15.273 | 25.935 | 61.745 | 1.00 | 62.38 |
| ATOM | 437 | CG | GLN | 62 | 16.757 | 26.269 | 61.786 | 1.00 | 73.32 |
| ATOM | 438 | CD | GLN | 62 | 17.063 | 27.538 | 62.556 | 1.00 | 76.87 |
| ATOM | 439 | OE1 | GLN | 62 | 18.227 | 27.888 | 62.753 | 1.00 | 80.04 |
| ATOM | 440 | NE2 | GLN | 62 | 16.021 | 28.237 | 62.991 | 1.00 | 78.44 |
| ATOM | 441 | C | GLN | 62 | 13.474 | 24.431 | 60.851 | 1.00 | 53.96 |
| ATOM | 442 | O | GLN | 62 | 12.924 | 24.349 | 61.947 | 1.00 | 54.21 |
| ATOM | 443 | N | LYS | 63 | 12.850 | 24.181 | 59.707 | 1.00 | 50.70 |
| ATOM | 444 | CA | LYS | 63 | 11.460 | 23.764 | 59.670 | 1.00 | 48.88 |
| ATOM | 445 | CB | LYS | 63 | 10.571 | 24.906 | 59.218 | 1.00 | 41.82 |
| ATOM | 446 | CG | LYS | 63 | 10.425 | 26.040 | 60.211 | 1.00 | 37.58 |
| ATOM | 447 | CD | LYS | 63 | 9.552 | 27.130 | 59.597 | 1.00 | 41.80 |
| ATOM | 448 | CE | LYS | 63 | 9.233 | 28.238 | 60.582 | 1.00 | 39.82 |
| ATOM | 449 | NZ | LYS | 63 | 8.422 | 27.723 | 61.709 | 1.00 | 37.91 |
| ATOM | 450 | C | LYS | 63 | 11.298 | 22.603 | 58.707 | 1.00 | 53.63 |
| ATOM | 451 | O | LYS | 63 | 10.302 | 21.877 | 58.754 | 1.00 | 58.07 |
| ATOM | 452 | N | THR | 64 | 12.281 | 22.438 | 57.826 | 1.00 | 49.48 |
| ATOM | 453 | CA | THR | 64 | 12.264 | 21.354 | 56.843 | 1.00 | 43.23 |
| ATOM | 454 | CB | THR | 64 | 11.266 | 21.657 | 55.671 | 1.00 | 47.88 |
| ATOM | 455 | OG1 | THR | 64 | 11.503 | 20.753 | 54.577 | 1.00 | 42.89 |
| ATOM | 456 | CG2 | THR | 64 | 11.425 | 23.099 | 55.191 | 1.00 | 42.13 |
| ATOM | 457 | C | THR | 64 | 13.671 | 21.174 | 56.294 | 1.00 | 38.73 |
| ATOM | 458 | O | THR | 64 | 14.495 | 22.086 | 56.371 | 1.00 | 30.08 |
| ATOM | 459 | N | ASP | 65 | 13.941 | 19.991 | 55.752 | 1.00 | 41.12 |
| ATOM | 460 | CA | ASP | 65 | 15.251 | 19.679 | 55.185 | 1.00 | 44.54 |
| ATOM | 461 | CB | ASP | 65 | 15.832 | 18.438 | 55.859 | 1.00 | 54.45 |
| ATOM | 462 | CG | ASP | 65 | 16.047 | 18.634 | 57.344 | 1.00 | 64.33 |
| ATOM | 463 | OD1 | ASP | 65 | 16.918 | 19.449 | 57.714 | 1.00 | 67.75 |
| ATOM | 464 | OD2 | ASP | 65 | 15.338 | 17.980 | 58.139 | 1.00 | 66.56 |
| ATOM | 465 | C | ASP | 65 | 15.108 | 19.436 | 53.691 | 1.00 | 43.83 |
| ATOM | 466 | O | ASP | 65 | 16.102 | 19.218 | 52.981 | 1.00 | 39.06 |
| ATOM | 467 | N | LYS | 66 | 13.856 | 19.477 | 53.231 | 1.00 | 41.67 |
| ATOM | 468 | CA | LYS | 66 | 13.523 | 19.273 | 51.825 | 1.00 | 37.87 |
| ATOM | 469 | CB | LYS | 66 | 12.014 | 19.153 | 51.660 | 1.00 | 34.13 |
| ATOM | 470 | CG | LYS | 66 | 11.347 | 18.217 | 52.630 | 1.00 | 34.68 |

TABLE 2-continued

Atomic coordinates on the three-dimensional crystal structure of the FabK-FMN complex having the amino acid sequences 2-312 of SEQ ID NO: 1

| A | B | C | D | E | F | G | H | I | J |
|---|---|---|---|---|---|---|---|---|---|
| ATOM | 471 | CD | LYS | 66 | 11.364 | 16.793 | 52.139 | 1.00 | 36.48 |
| ATOM | 472 | CE | LYS | 66 | 10.516 | 15.920 | 53.046 | 1.00 | 37.85 |
| ATOM | 473 | NZ | LYS | 66 | 9.092 | 16.382 | 53.071 | 1.00 | 43.48 |
| ATOM | 474 | C | LYS | 66 | 14.014 | 20.477 | 51.025 | 1.00 | 38.84 |
| ATOM | 475 | O | LYS | 66 | 14.323 | 21.530 | 51.595 | 1.00 | 40.13 |
| ATOM | 476 | N | PRO | 67 | 14.075 | 20.344 | 49.690 | 1.00 | 37.06 |
| ATOM | 477 | CD | PRO | 67 | 13.751 | 19.152 | 48.889 | 1.00 | 36.00 |
| ATOM | 478 | CA | PRO | 67 | 14.532 | 21.441 | 48.830 | 1.00 | 34.64 |
| ATOM | 479 | CB | PRO | 67 | 14.503 | 20.826 | 47.432 | 1.00 | 31.06 |
| ATOM | 480 | CG | PRO | 67 | 14.626 | 19.345 | 47.689 | 1.00 | 37.98 |
| ATOM | 481 | C | PRO | 67 | 13.610 | 22.653 | 48.918 | 1.00 | 34.53 |
| ATOM | 482 | O | PRO | 67 | 12.428 | 22.528 | 49.250 | 1.00 | 34.79 |
| ATOM | 483 | N | PHE | 68 | 14.162 | 23.824 | 48.619 | 1.00 | 34.16 |
| ATOM | 484 | CA | PHE | 68 | 13.399 | 25.076 | 48.621 | 1.00 | 35.45 |
| ATOM | 485 | CB | PHE | 68 | 13.264 | 25.658 | 50.036 | 1.00 | 34.53 |
| ATOM | 486 | CG | PHE | 68 | 14.566 | 26.131 | 50.629 | 1.00 | 45.33 |
| ATOM | 487 | CD1 | PHE | 68 | 14.738 | 27.467 | 50.982 | 1.00 | 47.81 |
| ATOM | 488 | CD2 | PHE | 68 | 15.618 | 25.241 | 50.841 | 1.00 | 42.56 |
| ATOM | 489 | CE1 | PHE | 68 | 15.936 | 27.912 | 51.539 | 1.00 | 48.42 |
| ATOM | 490 | CE2 | PHE | 68 | 16.818 | 25.674 | 51.396 | 1.00 | 45.45 |
| ATOM | 491 | CZ | PHE | 68 | 16.978 | 27.012 | 51.747 | 1.00 | 49.34 |
| ATOM | 492 | C | PHE | 68 | 14.145 | 26.056 | 47.734 | 1.00 | 32.79 |
| ATOM | 493 | O | PHE | 68 | 15.263 | 25.782 | 47.303 | 1.00 | 25.24 |
| ATOM | 494 | N | GLY | 69 | 13.522 | 27.194 | 47.457 | 1.00 | 30.06 |
| ATOM | 495 | CA | GLY | 69 | 14.163 | 28.176 | 46.616 | 1.00 | 31.24 |
| ATOM | 496 | C | GLY | 69 | 13.951 | 29.587 | 47.111 | 1.00 | 30.75 |
| ATOM | 497 | O | GLY | 69 | 13.214 | 29.821 | 48.074 | 1.00 | 33.01 |
| ATOM | 498 | N | VAL | 70 | 14.608 | 30.533 | 46.451 | 1.00 | 21.86 |
| ATOM | 499 | CA | VAL | 70 | 14.480 | 31.935 | 46.814 | 1.00 | 21.27 |
| ATOM | 500 | CB | VAL | 70 | 15.784 | 32.456 | 47.472 | 1.00 | 29.62 |
| ATOM | 501 | CG1 | VAL | 70 | 15.685 | 33.947 | 47.726 | 1.00 | 7.69 |
| ATOM | 502 | CG2 | VAL | 70 | 16.042 | 31.704 | 48.796 | 1.00 | 24.36 |
| ATOM | 503 | C | VAL | 70 | 14.174 | 32.761 | 45.567 | 1.00 | 21.00 |
| ATOM | 504 | O | VAL | 70 | 14.697 | 32.497 | 44.489 | 1.00 | 16.01 |
| ATOM | 505 | N | ASN | 71 | 13.311 | 33.755 | 45.721 | 1.00 | 24.62 |
| ATOM | 506 | CA | ASN | 71 | 12.944 | 34.622 | 44.613 | 1.00 | 30.46 |
| ATOM | 507 | CB | ASN | 71 | 11.430 | 34.779 | 44.561 | 1.00 | 31.49 |
| ATOM | 508 | CG | ASN | 71 | 10.994 | 35.768 | 43.517 | 1.00 | 37.78 |
| ATOM | 509 | OD1 | ASN | 71 | 11.153 | 35.528 | 42.320 | 1.00 | 38.80 |
| ATOM | 510 | ND2 | ASN | 71 | 10.451 | 36.900 | 43.962 | 1.00 | 34.35 |
| ATOM | 511 | C | ASN | 71 | 13.595 | 36.003 | 44.767 | 1.00 | 31.91 |
| ATOM | 512 | O | ASN | 71 | 13.551 | 36.597 | 45.847 | 1.00 | 33.72 |
| ATOM | 513 | N | ILE | 72 | 14.186 | 36.509 | 43.684 | 1.00 | 34.90 |
| ATOM | 514 | CA | ILE | 72 | 14.852 | 37.813 | 43.684 | 1.00 | 36.39 |
| ATOM | 515 | CB | ILE | 72 | 16.358 | 37.637 | 43.501 | 1.00 | 39.26 |
| ATOM | 516 | CG2 | ILE | 72 | 17.054 | 38.970 | 43.674 | 1.00 | 50.45 |
| ATOM | 517 | CG1 | ILE | 72 | 16.885 | 36.647 | 44.546 | 1.00 | 43.97 |
| ATOM | 518 | CD1 | ILE | 72 | 18.335 | 36.280 | 44.384 | 1.00 | 37.10 |
| ATOM | 519 | C | ILE | 72 | 14.302 | 38.727 | 42.580 | 1.00 | 39.62 |
| ATOM | 520 | O | ILE | 72 | 14.235 | 38.340 | 41.419 | 1.00 | 41.19 |
| ATOM | 521 | N | ILE | 73 | 13.938 | 39.949 | 42.949 | 1.00 | 40.86 |
| ATOM | 522 | CA | ILE | 73 | 13.341 | 40.900 | 42.019 | 1.00 | 51.87 |
| ATOM | 523 | CB | ILE | 73 | 12.673 | 42.050 | 42.813 | 1.00 | 54.28 |
| ATOM | 524 | CG2 | ILE | 73 | 12.221 | 43.155 | 41.877 | 1.00 | 54.08 |
| ATOM | 525 | CG1 | ILE | 73 | 11.449 | 41.520 | 43.561 | 1.00 | 56.94 |
| ATOM | 526 | CD1 | ILE | 73 | 11.750 | 40.442 | 44.574 | 1.00 | 68.63 |
| ATOM | 527 | C | ILE | 73 | 14.170 | 41.499 | 40.868 | 1.00 | 55.92 |
| ATOM | 528 | O | ILE | 73 | 13.602 | 41.851 | 39.832 | 1.00 | 67.66 |
| ATOM | 529 | N | LEU | 74 | 15.486 | 41.617 | 41.031 | 1.00 | 47.73 |
| ATOM | 530 | CA | LEU | 74 | 16.363 | 42.190 | 39.988 | 1.00 | 47.32 |
| ATOM | 531 | CB | LEU | 74 | 15.936 | 41.767 | 38.573 | 1.00 | 37.81 |
| ATOM | 532 | CG | LEU | 74 | 16.190 | 40.323 | 38.129 | 1.00 | 43.40 |
| ATOM | 533 | CD1 | LEU | 74 | 15.749 | 40.168 | 36.677 | 1.00 | 38.38 |
| ATOM | 534 | CD2 | LEU | 74 | 17.678 | 39.970 | 38.280 | 1.00 | 40.66 |
| ATOM | 535 | C | LEU | 74 | 16.443 | 43.712 | 40.017 | 1.00 | 47.08 |
| ATOM | 536 | O | LEU | 74 | 17.531 | 44.276 | 40.039 | 1.00 | 50.79 |
| ATOM | 537 | N | VAL | 75 | 15.294 | 44.379 | 39.996 | 1.00 | 49.14 |
| ATOM | 538 | CA | VAL | 75 | 15.267 | 45.838 | 40.028 | 1.00 | 47.80 |
| ATOM | 539 | CB | VAL | 75 | 13.942 | 46.379 | 39.435 | 1.00 | 44.20 |
| ATOM | 540 | CG1 | VAL | 75 | 13.484 | 45.472 | 38.293 | 1.00 | 39.12 |
| ATOM | 541 | CG2 | VAL | 75 | 12.869 | 46.475 | 40.515 | 1.00 | 35.33 |
| ATOM | 542 | C | VAL | 75 | 15.414 | 46.312 | 41.476 | 1.00 | 48.56 |
| ATOM | 543 | O | VAL | 75 | 15.247 | 47.491 | 41.787 | 1.00 | 47.05 |
| ATOM | 544 | N | SER | 76 | 15.727 | 45.370 | 42.358 | 1.00 | 51.63 |

TABLE 2-continued

Atomic coordinates on the three-dimensional crystal structure of the FabK-FMN complex having the amino acid sequences 2-312 of SEQ ID NO: 1

| A | B | C | D | E | F | G | H | I | J |
|---|---|---|---|---|---|---|---|---|---|
| ATOM | 545 | CA | SER | 76 | 15.890 | 45.664 | 43.772 | 1.00 | 47.92 |
| ATOM | 546 | CB | SER | 76 | 15.709 | 44.390 | 44.593 | 1.00 | 46.17 |
| ATOM | 547 | OG | SER | 76 | 15.922 | 44.653 | 45.967 | 1.00 | 44.65 |
| ATOM | 548 | C | SER | 76 | 17.253 | 46.269 | 44.071 | 1.00 | 47.71 |
| ATOM | 549 | O | SER | 76 | 18.259 | 45.876 | 43.482 | 1.00 | 45.75 |
| ATOM | 550 | N | PRO | 77 | 17.302 | 47.233 | 45.006 | 1.00 | 46.02 |
| ATOM | 551 | CD | PRO | 77 | 16.179 | 47.785 | 45.784 | 1.00 | 45.08 |
| ATOM | 552 | CA | PRO | 77 | 18.552 | 47.892 | 45.380 | 1.00 | 46.60 |
| ATOM | 553 | CB | PRO | 77 | 18.119 | 48.837 | 46.499 | 1.00 | 47.39 |
| ATOM | 554 | CG | PRO | 77 | 16.705 | 49.141 | 46.167 | 1.00 | 43.20 |
| ATOM | 555 | C | PRO | 77 | 19.633 | 46.919 | 45.850 | 1.00 | 50.88 |
| ATOM | 556 | O | PRO | 77 | 20.825 | 47.216 | 45.739 | 1.00 | 51.72 |
| ATOM | 557 | N | TRP | 78 | 19.223 | 45.755 | 46.356 | 1.00 | 52.02 |
| ATOM | 558 | CA | TRP | 78 | 20.180 | 44.775 | 46.870 | 1.00 | 50.04 |
| ATOM | 559 | CB | TRP | 78 | 19.837 | 44.441 | 48.316 | 1.00 | 55.41 |
| ATOM | 560 | CG | TRP | 78 | 19.311 | 45.604 | 49.067 | 1.00 | 58.20 |
| ATOM | 561 | CD2 | TRP | 78 | 20.053 | 46.470 | 49.926 | 1.00 | 62.21 |
| ATOM | 562 | CE2 | TRP | 78 | 19.159 | 47.460 | 50.393 | 1.00 | 66.48 |
| ATOM | 563 | CE3 | TRP | 78 | 21.389 | 46.509 | 50.346 | 1.00 | 63.54 |
| ATOM | 564 | CD1 | TRP | 78 | 18.035 | 46.083 | 49.046 | 1.00 | 60.30 |
| ATOM | 565 | NE1 | TRP | 78 | 17.933 | 47.197 | 49.841 | 1.00 | 63.74 |
| ATOM | 566 | CZ2 | TRP | 78 | 19.556 | 48.480 | 51.261 | 1.00 | 70.89 |
| ATOM | 567 | CZ3 | TRP | 78 | 21.786 | 47.520 | 51.208 | 1.00 | 70.95 |
| ATOM | 568 | CH2 | TRP | 78 | 20.869 | 48.495 | 51.657 | 1.00 | 74.32 |
| ATOM | 569 | C | TRP | 78 | 20.299 | 43.474 | 46.086 | 1.00 | 46.15 |
| ATOM | 570 | O | TRP | 78 | 20.904 | 42.519 | 46.565 | 1.00 | 46.75 |
| ATOM | 571 | N | ALA | 79 | 19.731 | 43.433 | 44.888 | 1.00 | 43.79 |
| ATOM | 572 | CA | ALA | 79 | 19.785 | 42.229 | 44.065 | 1.00 | 44.79 |
| ATOM | 573 | CB | ALA | 79 | 19.392 | 42.563 | 42.629 | 1.00 | 37.67 |
| ATOM | 574 | C | ALA | 79 | 21.153 | 41.539 | 44.082 | 1.00 | 47.14 |
| ATOM | 575 | O | ALA | 79 | 21.244 | 40.331 | 44.305 | 1.00 | 44.90 |
| ATOM | 576 | N | ASP | 80 | 22.218 | 42.304 | 43.853 | 1.00 | 48.46 |
| ATOM | 577 | CA | ASP | 80 | 23.560 | 41.729 | 43.830 | 1.00 | 50.48 |
| ATOM | 578 | CB | ASP | 80 | 24.590 | 42.814 | 43.505 | 1.00 | 59.02 |
| ATOM | 579 | CG | ASP | 80 | 24.468 | 43.323 | 42.077 | 1.00 | 69.27 |
| ATOM | 580 | OD1 | ASP | 80 | 23.399 | 43.872 | 41.727 | 1.00 | 73.51 |
| ATOM | 581 | OD2 | ASP | 80 | 25.437 | 43.170 | 41.303 | 1.00 | 66.47 |
| ATOM | 582 | C | ASP | 80 | 23.914 | 41.045 | 45.141 | 1.00 | 46.21 |
| ATOM | 583 | O | ASP | 80 | 24.368 | 39.904 | 45.160 | 1.00 | 38.56 |
| ATOM | 584 | N | ASP | 81 | 23.694 | 41.756 | 46.237 | 1.00 | 46.60 |
| ATOM | 585 | CA | ASP | 81 | 23.980 | 41.234 | 47.560 | 1.00 | 46.97 |
| ATOM | 586 | CB | ASP | 81 | 23.696 | 42.307 | 48.610 | 1.00 | 58.20 |
| ATOM | 587 | CG | ASP | 81 | 24.471 | 43.586 | 48.353 | 1.00 | 73.76 |
| ATOM | 588 | OD1 | ASP | 81 | 25.720 | 43.528 | 48.299 | 1.00 | 73.68 |
| ATOM | 589 | OD2 | ASP | 81 | 23.831 | 44.650 | 48.202 | 1.00 | 82.81 |
| ATOM | 590 | C | ASP | 81 | 23.130 | 39.998 | 47.825 | 1.00 | 42.88 |
| ATOM | 591 | O | ASP | 81 | 23.628 | 38.991 | 48.333 | 1.00 | 42.55 |
| ATOM | 592 | N | LEU | 82 | 21.849 | 40.075 | 47.471 | 1.00 | 37.71 |
| ATOM | 593 | CA | LEU | 82 | 20.935 | 38.954 | 47.671 | 1.00 | 32.98 |
| ATOM | 594 | CB | LEU | 82 | 19.522 | 39.337 | 47.227 | 1.00 | 28.65 |
| ATOM | 595 | CG | LEU | 82 | 18.846 | 40.375 | 48.130 | 1.00 | 30.21 |
| ATOM | 596 | CD1 | LEU | 82 | 17.424 | 40.641 | 47.658 | 1.00 | 36.71 |
| ATOM | 597 | CD2 | LEU | 82 | 18.828 | 39.877 | 49.548 | 1.00 | 21.63 |
| ATOM | 598 | C | LEU | 82 | 21.399 | 37.708 | 46.924 | 1.00 | 30.76 |
| ATOM | 599 | O | LEU | 82 | 21.331 | 36.597 | 47.451 | 1.00 | 26.47 |
| ATOM | 600 | N | VAL | 83 | 21.877 | 37.888 | 45.700 | 1.00 | 27.63 |
| ATOM | 601 | CA | VAL | 83 | 22.343 | 36.745 | 44.941 | 1.00 | 30.56 |
| ATOM | 602 | CB | VAL | 83 | 22.871 | 37.134 | 43.577 | 1.00 | 26.54 |
| ATOM | 603 | CG1 | VAL | 83 | 23.237 | 35.887 | 42.815 | 1.00 | 31.29 |
| ATOM | 604 | CG2 | VAL | 83 | 21.836 | 37.924 | 42.822 | 1.00 | 31.94 |
| ATOM | 605 | C | VAL | 83 | 23.478 | 36.089 | 45.698 | 1.00 | 35.03 |
| ATOM | 606 | O | VAL | 83 | 23.574 | 34.861 | 45.744 | 1.00 | 37.51 |
| ATOM | 607 | N | LYS | 84 | 24.333 | 36.918 | 46.295 | 1.00 | 33.11 |
| ATOM | 608 | CA | LYS | 84 | 25.474 | 36.423 | 47.053 | 1.00 | 33.24 |
| ATOM | 609 | CB | LYS | 84 | 26.392 | 37.573 | 47.475 | 1.00 | 43.97 |
| ATOM | 610 | CG | LYS | 84 | 26.899 | 38.453 | 46.342 | 1.00 | 51.31 |
| ATOM | 611 | CD | LYS | 84 | 28.004 | 39.379 | 46.854 | 1.00 | 58.12 |
| ATOM | 612 | CE | LYS | 84 | 28.240 | 40.583 | 45.947 | 1.00 | 57.58 |
| ATOM | 613 | NZ | LYS | 84 | 27.117 | 41.567 | 45.993 | 1.00 | 56.42 |
| ATOM | 614 | C | LYS | 84 | 25.037 | 35.650 | 48.292 | 1.00 | 33.00 |
| ATOM | 615 | O | LYS | 84 | 25.606 | 34.605 | 48.601 | 1.00 | 29.29 |
| ATOM | 616 | N | VAL | 85 | 24.048 | 36.160 | 49.016 | 1.00 | 28.55 |
| ATOM | 617 | CA | VAL | 85 | 23.584 | 35.450 | 50.201 | 1.00 | 33.15 |
| ATOM | 618 | CB | VAL | 85 | 22.398 | 36.175 | 50.874 | 1.00 | 35.16 |

TABLE 2-continued

Atomic coordinates on the three-dimensional crystal structure of the FabK-FMN complex having the amino acid sequences 2-312 of SEQ ID NO: 1

| A | B | C | D | E | F | G | H | I | J |
|---|---|---|---|---|---|---|---|---|---|
| ATOM | 619 | CG1 | VAL | 85 | 21.770 | 35.274 | 51.941 | 1.00 | 29.21 |
| ATOM | 620 | CG2 | VAL | 85 | 22.878 | 37.501 | 51.496 | 1.00 | 32.04 |
| ATOM | 621 | C | VAL | 85 | 23.140 | 34.052 | 49.762 | 1.00 | 37.09 |
| ATOM | 622 | O | VAL | 85 | 23.488 | 33.047 | 50.387 | 1.00 | 34.53 |
| ATOM | 623 | N | CYS | 86 | 22.387 | 34.000 | 48.668 | 1.00 | 37.37 |
| ATOM | 624 | CA | CYS | 86 | 21.912 | 32.732 | 48.137 | 1.00 | 43.30 |
| ATOM | 625 | CB | CYS | 86 | 21.157 | 32.959 | 46.832 | 1.00 | 39.99 |
| ATOM | 626 | SG | CYS | 86 | 19.514 | 33.579 | 47.085 | 1.00 | 40.84 |
| ATOM | 627 | C | CYS | 86 | 23.058 | 31.765 | 47.887 | 1.00 | 43.76 |
| ATOM | 628 | O | CYS | 86 | 22.960 | 30.571 | 48.166 | 1.00 | 40.82 |
| ATOM | 629 | N | ILE | 87 | 24.143 | 32.293 | 47.343 | 1.00 | 43.37 |
| ATOM | 630 | CA | ILE | 87 | 25.304 | 31.485 | 47.039 | 1.00 | 46.78 |
| ATOM | 631 | CB | ILE | 87 | 26.370 | 32.324 | 46.327 | 1.00 | 54.17 |
| ATOM | 632 | CG2 | ILE | 87 | 27.612 | 31.489 | 46.081 | 1.00 | 51.97 |
| ATOM | 633 | CG1 | ILE | 87 | 25.799 | 32.872 | 45.020 | 1.00 | 51.71 |
| ATOM | 634 | CD1 | ILE | 87 | 26.675 | 33.891 | 44.358 | 1.00 | 50.90 |
| ATOM | 635 | C | ILE | 87 | 25.909 | 30.919 | 48.310 | 1.00 | 46.85 |
| ATOM | 636 | O | ILE | 87 | 25.881 | 29.708 | 48.546 | 1.00 | 44.43 |
| ATOM | 637 | N | GLU | 88 | 26.451 | 31.811 | 49.127 | 1.00 | 39.37 |
| ATOM | 638 | CA | GLU | 88 | 27.097 | 31.416 | 50.361 | 1.00 | 45.34 |
| ATOM | 639 | CB | GLU | 88 | 27.610 | 32.655 | 51.093 | 1.00 | 48.23 |
| ATOM | 640 | CG | GLU | 88 | 26.574 | 33.742 | 51.280 | 1.00 | 56.49 |
| ATOM | 641 | CD | GLU | 88 | 27.177 | 35.126 | 51.166 | 1.00 | 59.43 |
| ATOM | 642 | OE1 | GLU | 88 | 26.423 | 36.115 | 51.268 | 1.00 | 64.51 |
| ATOM | 643 | OE2 | GLU | 88 | 28.407 | 35.225 | 50.966 | 1.00 | 59.23 |
| ATOM | 644 | C | GLU | 88 | 26.214 | 30.586 | 51.279 | 1.00 | 44.52 |
| ATOM | 645 | O | GLU | 88 | 26.719 | 29.863 | 52.138 | 1.00 | 45.10 |
| ATOM | 646 | N | GLU | 89 | 24.901 | 30.687 | 51.114 | 1.00 | 39.47 |
| ATOM | 647 | CA | GLU | 89 | 24.005 | 29.894 | 51.947 | 1.00 | 38.49 |
| ATOM | 648 | CB | GLU | 89 | 22.782 | 30.716 | 52.355 | 1.00 | 47.59 |
| ATOM | 649 | CG | GLU | 89 | 22.635 | 30.854 | 53.876 | 1.00 | 63.65 |
| ATOM | 650 | CD | GLU | 89 | 23.870 | 31.449 | 54.552 | 1.00 | 66.46 |
| ATOM | 651 | OE1 | GLU | 89 | 24.984 | 30.928 | 54.340 | 1.00 | 64.97 |
| ATOM | 652 | OE2 | GLU | 89 | 23.725 | 32.436 | 55.306 | 1.00 | 68.48 |
| ATOM | 653 | C | GLU | 89 | 23.594 | 28.612 | 51.221 | 1.00 | 35.50 |
| ATOM | 654 | O | GLU | 89 | 22.750 | 27.857 | 51.691 | 1.00 | 27.22 |
| ATOM | 655 | N | LYS | 90 | 24.227 | 28.378 | 50.076 | 1.00 | 41.44 |
| ATOM | 656 | CA | LYS | 90 | 23.988 | 27.202 | 49.250 | 1.00 | 46.54 |
| ATOM | 657 | CB | LYS | 90 | 24.638 | 25.973 | 49.887 | 1.00 | 50.54 |
| ATOM | 658 | CG | LYS | 90 | 26.064 | 26.206 | 50.374 | 1.00 | 67.26 |
| ATOM | 659 | CD | LYS | 90 | 26.879 | 27.106 | 49.433 | 1.00 | 83.23 |
| ATOM | 660 | CE | LYS | 90 | 27.022 | 26.531 | 48.027 | 1.00 | 90.90 |
| ATOM | 661 | NZ | LYS | 90 | 27.815 | 27.437 | 47.143 | 1.00 | 97.47 |
| ATOM | 662 | C | LYS | 90 | 22.518 | 26.923 | 48.975 | 1.00 | 45.30 |
| ATOM | 663 | O | LYS | 90 | 22.047 | 25.790 | 49.118 | 1.00 | 43.64 |
| ATOM | 664 | N | VAL | 91 | 21.798 | 27.966 | 48.575 | 1.00 | 39.35 |
| ATOM | 665 | CA | VAL | 91 | 20.380 | 27.834 | 48.257 | 1.00 | 37.60 |
| ATOM | 666 | CB | VAL | 91 | 19.768 | 29.198 | 47.900 | 1.00 | 36.37 |
| ATOM | 667 | CG1 | VAL | 91 | 18.313 | 29.029 | 47.482 | 1.00 | 31.48 |
| ATOM | 668 | CG2 | VAL | 91 | 19.886 | 30.134 | 49.110 | 1.00 | 36.25 |
| ATOM | 669 | C | VAL | 91 | 20.205 | 26.859 | 47.094 | 1.00 | 34.99 |
| ATOM | 670 | O | VAL | 91 | 20.871 | 26.977 | 46.061 | 1.00 | 30.02 |
| ATOM | 671 | N | PRO | 92 | 19.306 | 25.871 | 47.261 | 1.00 | 33.52 |
| ATOM | 672 | CD | PRO | 92 | 18.447 | 25.730 | 48.450 | 1.00 | 32.55 |
| ATOM | 673 | CA | PRO | 92 | 19.000 | 24.835 | 46.270 | 1.00 | 28.53 |
| ATOM | 674 | CB | PRO | 92 | 17.909 | 24.012 | 46.954 | 1.00 | 32.25 |
| ATOM | 675 | CG | PRO | 92 | 18.122 | 24.280 | 48.427 | 1.00 | 29.68 |
| ATOM | 676 | C | PRO | 92 | 18.526 | 25.381 | 44.925 | 1.00 | 31.97 |
| ATOM | 677 | O | PRO | 92 | 19.040 | 24.990 | 43.871 | 1.00 | 29.51 |
| ATOM | 678 | N | VAL | 93 | 17.545 | 26.284 | 44.972 | 1.00 | 28.94 |
| ATOM | 679 | CA | VAL | 93 | 16.968 | 26.870 | 43.767 | 1.00 | 31.10 |
| ATOM | 680 | CB | VAL | 93 | 15.632 | 26.162 | 43.417 | 1.00 | 32.08 |
| ATOM | 681 | CG1 | VAL | 93 | 14.985 | 26.803 | 42.216 | 1.00 | 27.86 |
| ATOM | 682 | CG2 | VAL | 93 | 15.888 | 24.698 | 43.137 | 1.00 | 38.90 |
| ATOM | 683 | C | VAL | 93 | 16.701 | 28.382 | 43.850 | 1.00 | 32.47 |
| ATOM | 684 | O | VAL | 93 | 16.138 | 28.885 | 44.830 | 1.00 | 25.21 |
| ATOM | 685 | N | VAL | 94 | 17.108 | 29.106 | 42.811 | 1.00 | 29.22 |
| ATOM | 686 | CA | VAL | 94 | 16.864 | 30.547 | 42.769 | 1.00 | 29.72 |
| ATOM | 687 | CB | VAL | 94 | 18.180 | 31.365 | 42.685 | 1.00 | 28.11 |
| ATOM | 688 | CG1 | VAL | 94 | 17.879 | 32.812 | 42.324 | 1.00 | 26.48 |
| ATOM | 689 | CG2 | VAL | 94 | 18.886 | 31.326 | 44.028 | 1.00 | 26.42 |
| ATOM | 690 | C | VAL | 94 | 15.946 | 30.936 | 41.607 | 1.00 | 28.85 |
| ATOM | 691 | O | VAL | 94 | 16.094 | 30.461 | 40.477 | 1.00 | 24.44 |
| ATOM | 692 | N | THR | 95 | 14.999 | 31.807 | 41.921 | 1.00 | 31.07 |

TABLE 2-continued

Atomic coordinates on the three-dimensional crystal structure of the FabK-FMN complex having the amino acid sequences 2-312 of SEQ ID NO: 1

| A | B | C | D | E | F | G | H | I | J |
|---|---|---|---|---|---|---|---|---|---|
| ATOM | 693 | CA | THR | 95 | 14.016 | 32.306 | 40.973 | 1.00 | 38.82 |
| ATOM | 694 | CB | THR | 95 | 12.601 | 32.041 | 41.503 | 1.00 | 35.93 |
| ATOM | 695 | OG1 | THR | 95 | 12.293 | 30.652 | 41.352 | 1.00 | 42.40 |
| ATOM | 696 | CG2 | THR | 95 | 11.586 | 32.874 | 40.771 | 1.00 | 47.41 |
| ATOM | 697 | C | THR | 95 | 14.203 | 33.808 | 40.790 | 1.00 | 37.51 |
| ATOM | 698 | O | THR | 95 | 14.500 | 34.520 | 41.748 | 1.00 | 41.71 |
| ATOM | 699 | N | PHE | 96 | 14.018 | 34.289 | 39.567 | 1.00 | 34.13 |
| ATOM | 700 | CA | PHE | 96 | 14.179 | 35.711 | 39.287 | 1.00 | 35.94 |
| ATOM | 701 | CB | PHE | 96 | 15.277 | 35.921 | 38.250 | 1.00 | 30.04 |
| ATOM | 702 | CG | PHE | 96 | 16.652 | 35.753 | 38.795 | 1.00 | 35.00 |
| ATOM | 703 | CD1 | PHE | 96 | 17.417 | 34.644 | 38.456 | 1.00 | 29.24 |
| ATOM | 704 | CD2 | PHE | 96 | 17.187 | 36.709 | 39.657 | 1.00 | 30.30 |
| ATOM | 705 | CE1 | PHE | 96 | 18.692 | 34.487 | 38.964 | 1.00 | 34.08 |
| ATOM | 706 | CE2 | PHE | 96 | 18.462 | 36.559 | 40.172 | 1.00 | 37.04 |
| ATOM | 707 | CZ | PHE | 96 | 19.218 | 35.446 | 39.826 | 1.00 | 36.49 |
| ATOM | 708 | C | PHE | 96 | 12.927 | 36.430 | 38.816 | 1.00 | 34.37 |
| ATOM | 709 | O | PHE | 96 | 12.249 | 35.975 | 37.899 | 1.00 | 36.58 |
| ATOM | 710 | N | GLY | 97 | 12.644 | 37.568 | 39.437 | 1.00 | 41.10 |
| ATOM | 711 | CA | GLY | 97 | 11.483 | 38.350 | 39.067 | 1.00 | 50.46 |
| ATOM | 712 | C | GLY | 97 | 11.634 | 39.010 | 37.710 | 1.00 | 58.07 |
| ATOM | 713 | O | GLY | 97 | 11.521 | 38.339 | 36.691 | 1.00 | 57.87 |
| ATOM | 714 | N | ALA | 98 | 11.894 | 40.318 | 37.709 | 1.00 | 67.65 |
| ATOM | 715 | CA | ALA | 98 | 12.050 | 41.129 | 36.493 | 1.00 | 68.58 |
| ATOM | 716 | CB | ALA | 98 | 13.199 | 42.110 | 36.670 | 1.00 | 68.42 |
| ATOM | 717 | C | ALA | 98 | 12.223 | 40.358 | 35.185 | 1.00 | 70.58 |
| ATOM | 718 | O | ALA | 98 | 11.320 | 39.633 | 34.770 | 1.00 | 71.45 |
| ATOM | 719 | N | GLY | 99 | 13.366 | 40.523 | 34.519 | 1.00 | 70.11 |
| ATOM | 720 | CA | GLY | 99 | 13.556 | 39.806 | 33.270 | 1.00 | 72.78 |
| ATOM | 721 | C | GLY | 99 | 14.884 | 39.926 | 32.543 | 1.00 | 74.70 |
| ATOM | 722 | O | GLY | 99 | 14.949 | 40.496 | 31.456 | 1.00 | 78.06 |
| ATOM | 723 | N | ASN | 100 | 15.939 | 39.374 | 33.133 | 1.00 | 75.47 |
| ATOM | 724 | CA | ASN | 100 | 17.271 | 39.385 | 32.534 | 1.00 | 73.08 |
| ATOM | 725 | CB | ASN | 100 | 17.643 | 40.775 | 32.021 | 1.00 | 80.61 |
| ATOM | 726 | CG | ASN | 100 | 18.799 | 40.736 | 31.034 | 1.00 | 88.19 |
| ATOM | 727 | OD1 | ASN | 100 | 19.440 | 41.755 | 30.766 | 1.00 | 89.46 |
| ATOM | 728 | ND2 | ASN | 100 | 19.062 | 39.554 | 30.478 | 1.00 | 85.81 |
| ATOM | 729 | C | ASN | 100 | 18.268 | 38.968 | 33.597 | 1.00 | 67.56 |
| ATOM | 730 | O | ASN | 100 | 19.055 | 39.780 | 34.080 | 1.00 | 69.43 |
| ATOM | 731 | N | PRO | 101 | 18.244 | 37.689 | 33.981 | 1.00 | 57.19 |
| ATOM | 732 | CD | PRO | 101 | 17.196 | 36.699 | 33.711 | 1.00 | 52.52 |
| ATOM | 733 | CA | PRO | 101 | 19.158 | 37.187 | 35.003 | 1.00 | 54.36 |
| ATOM | 734 | CB | PRO | 101 | 18.403 | 35.986 | 35.585 | 1.00 | 51.42 |
| ATOM | 735 | CG | PRO | 101 | 16.990 | 36.132 | 35.071 | 1.00 | 51.13 |
| ATOM | 736 | C | PRO | 101 | 20.515 | 36.775 | 34.446 | 1.00 | 51.56 |
| ATOM | 737 | O | PRO | 101 | 21.371 | 36.314 | 35.189 | 1.00 | 51.73 |
| ATOM | 738 | N | THR | 102 | 20.708 | 36.933 | 33.142 | 1.00 | 52.18 |
| ATOM | 739 | CA | THR | 102 | 21.965 | 36.542 | 32.510 | 1.00 | 55.44 |
| ATOM | 740 | CB | THR | 102 | 22.073 | 37.131 | 31.093 | 1.00 | 58.58 |
| ATOM | 741 | OG1 | THR | 102 | 20.926 | 36.733 | 30.333 | 1.00 | 60.32 |
| ATOM | 742 | CG2 | THR | 102 | 23.336 | 36.629 | 30.392 | 1.00 | 53.06 |
| ATOM | 743 | C | THR | 102 | 23.183 | 36.966 | 33.322 | 1.00 | 57.59 |
| ATOM | 744 | O | THR | 102 | 24.143 | 36.206 | 33.463 | 1.00 | 60.39 |
| ATOM | 745 | N | LYS | 103 | 23.130 | 38.176 | 33.866 | 1.00 | 58.36 |
| ATOM | 746 | CA | LYS | 103 | 24.219 | 38.718 | 34.665 | 1.00 | 57.14 |
| ATOM | 747 | CB | LYS | 103 | 23.916 | 40.182 | 35.000 | 1.00 | 64.79 |
| ATOM | 748 | CG | LYS | 103 | 24.954 | 40.870 | 35.874 | 1.00 | 77.18 |
| ATOM | 749 | CD | LYS | 103 | 24.503 | 42.277 | 36.257 | 1.00 | 86.22 |
| ATOM | 750 | CE | LYS | 103 | 25.550 | 43.000 | 37.099 | 1.00 | 91.61 |
| ATOM | 751 | NZ | LYS | 103 | 25.808 | 42.328 | 38.403 | 1.00 | 93.73 |
| ATOM | 752 | C | LYS | 103 | 24.447 | 37.929 | 35.958 | 1.00 | 52.94 |
| ATOM | 753 | O | LYS | 103 | 25.411 | 38.188 | 36.684 | 1.00 | 49.81 |
| ATOM | 754 | N | TYR | 104 | 23.577 | 36.960 | 36.235 | 1.00 | 39.30 |
| ATOM | 755 | CA | TYR | 104 | 23.684 | 36.171 | 37.465 | 1.00 | 37.49 |
| ATOM | 756 | CB | TYR | 104 | 22.521 | 36.508 | 38.403 | 1.00 | 38.11 |
| ATOM | 757 | CG | TYR | 104 | 22.508 | 37.910 | 38.956 | 1.00 | 43.68 |
| ATOM | 758 | CD1 | TYR | 104 | 21.336 | 38.667 | 38.947 | 1.00 | 40.03 |
| ATOM | 759 | CE1 | TYR | 104 | 21.295 | 39.931 | 39.510 | 1.00 | 41.35 |
| ATOM | 760 | CD2 | TYR | 104 | 23.644 | 38.461 | 39.542 | 1.00 | 37.15 |
| ATOM | 761 | CE2 | TYR | 104 | 23.612 | 39.728 | 40.112 | 1.00 | 40.82 |
| ATOM | 762 | CZ | TYR | 104 | 22.437 | 40.457 | 40.095 | 1.00 | 44.39 |
| ATOM | 763 | OH | TYR | 104 | 22.398 | 41.704 | 40.678 | 1.00 | 50.09 |
| ATOM | 764 | C | TYR | 104 | 23.688 | 34.658 | 37.288 | 1.00 | 35.16 |
| ATOM | 765 | O | TYR | 104 | 23.873 | 33.923 | 38.262 | 1.00 | 31.29 |
| ATOM | 766 | N | ILE | 105 | 23.466 | 34.187 | 36.067 | 1.00 | 40.21 |

TABLE 2-continued

Atomic coordinates on the three-dimensional crystal structure of the FabK-
FMN complex having the amino acid sequences 2-312 of SEQ ID NO: 1

| A | B | C | D | E | F | G | H | I | J |
|---|---|---|---|---|---|---|---|---|---|
| ATOM | 767 | CA | ILE | 105 | 23.406 | 32.753 | 35.831 | 1.00 | 41.23 |
| ATOM | 768 | CB | ILE | 105 | 22.967 | 32.436 | 34.384 | 1.00 | 42.85 |
| ATOM | 769 | CG2 | ILE | 105 | 22.418 | 31.025 | 34.314 | 1.00 | 42.62 |
| ATOM | 770 | CG1 | ILE | 105 | 21.855 | 33.393 | 33.939 | 1.00 | 38.95 |
| ATOM | 771 | CD1 | ILE | 105 | 20.599 | 33.355 | 34.785 | 1.00 | 26.09 |
| ATOM | 772 | C | ILE | 105 | 24.720 | 32.049 | 36.129 | 1.00 | 42.49 |
| ATOM | 773 | O | ILE | 105 | 24.757 | 31.132 | 36.949 | 1.00 | 41.07 |
| ATOM | 774 | N | ARG | 106 | 25.796 | 32.478 | 35.479 | 1.00 | 50.34 |
| ATOM | 775 | CA | ARG | 106 | 27.105 | 31.860 | 35.688 | 1.00 | 58.80 |
| ATOM | 776 | CB | ARG | 106 | 28.211 | 32.742 | 35.105 | 1.00 | 64.19 |
| ATOM | 777 | CG | ARG | 106 | 28.692 | 32.275 | 33.750 | 1.00 | 69.63 |
| ATOM | 778 | CD | ARG | 106 | 29.267 | 30.871 | 33.846 | 1.00 | 79.16 |
| ATOM | 779 | NE | ARG | 106 | 28.818 | 30.022 | 32.746 | 1.00 | 90.54 |
| ATOM | 780 | CZ | ARG | 106 | 27.550 | 29.678 | 32.537 | 1.00 | 95.20 |
| ATOM | 781 | NH1 | ARG | 106 | 26.597 | 30.107 | 33.355 | 1.00 | 100.15 |
| ATOM | 782 | NH2 | ARG | 106 | 27.230 | 28.909 | 31.505 | 1.00 | 95.38 |
| ATOM | 783 | C | ARG | 106 | 27.444 | 31.519 | 37.140 | 1.00 | 61.82 |
| ATOM | 784 | O | ARG | 106 | 27.532 | 30.342 | 37.496 | 1.00 | 59.56 |
| ATOM | 785 | N | GLU | 107 | 27.631 | 32.539 | 37.973 | 1.00 | 63.41 |
| ATOM | 786 | CA | GLU | 107 | 27.983 | 32.326 | 39.376 | 1.00 | 64.77 |
| ATOM | 787 | CB | GLU | 107 | 28.143 | 33.673 | 40.091 | 1.00 | 77.89 |
| ATOM | 788 | CG | GLU | 107 | 27.040 | 34.683 | 39.824 | 1.00 | 97.63 |
| ATOM | 789 | CD | GLU | 107 | 27.291 | 36.014 | 40.521 | 1.00 | 106.03 |
| ATOM | 790 | OE1 | GLU | 107 | 26.467 | 36.939 | 40.353 | 1.00 | 112.57 |
| ATOM | 791 | OE2 | GLU | 107 | 28.311 | 36.134 | 41.236 | 1.00 | 108.53 |
| ATOM | 792 | C | GLU | 107 | 27.049 | 31.407 | 40.175 | 1.00 | 58.74 |
| ATOM | 793 | O | GLU | 107 | 27.521 | 30.538 | 40.910 | 1.00 | 59.07 |
| ATOM | 794 | N | LEU | 108 | 25.737 | 31.585 | 40.049 | 1.00 | 51.28 |
| ATOM | 795 | CA | LEU | 108 | 24.800 | 30.723 | 40.770 | 1.00 | 43.53 |
| ATOM | 796 | CB | LEU | 108 | 23.366 | 31.187 | 40.526 | 1.00 | 41.21 |
| ATOM | 797 | CG | LEU | 108 | 22.947 | 32.392 | 41.370 | 1.00 | 45.34 |
| ATOM | 798 | CD1 | LEU | 108 | 21.856 | 33.179 | 40.664 | 1.00 | 44.97 |
| ATOM | 799 | CD2 | LEU | 108 | 22.487 | 31.911 | 42.737 | 1.00 | 40.51 |
| ATOM | 800 | C | LEU | 108 | 24.980 | 29.293 | 40.266 | 1.00 | 45.99 |
| ATOM | 801 | O | LEU | 108 | 24.859 | 28.317 | 41.017 | 1.00 | 30.73 |
| ATOM | 802 | N | LYS | 109 | 25.277 | 29.193 | 38.976 | 1.00 | 49.06 |
| ATOM | 803 | CA | LYS | 109 | 25.501 | 27.916 | 38.333 | 1.00 | 54.20 |
| ATOM | 804 | CB | LYS | 109 | 25.482 | 28.100 | 36.816 | 1.00 | 59.74 |
| ATOM | 805 | CG | LYS | 109 | 25.137 | 26.845 | 36.029 | 1.00 | 71.07 |
| ATOM | 806 | CD | LYS | 109 | 23.772 | 26.284 | 36.411 | 1.00 | 75.90 |
| ATOM | 807 | CE | LYS | 109 | 22.721 | 27.373 | 36.451 | 1.00 | 84.27 |
| ATOM | 808 | NZ | LYS | 109 | 22.814 | 28.255 | 35.260 | 1.00 | 90.77 |
| ATOM | 809 | C | LYS | 109 | 26.859 | 27.374 | 38.791 | 1.00 | 56.97 |
| ATOM | 810 | O | LYS | 109 | 27.034 | 26.162 | 38.914 | 1.00 | 53.03 |
| ATOM | 811 | N | GLU | 110 | 27.809 | 28.280 | 39.045 | 1.00 | 60.34 |
| ATOM | 812 | CA | GLU | 110 | 29.157 | 27.913 | 39.494 | 1.00 | 64.08 |
| ATOM | 813 | CB | GLU | 110 | 30.013 | 29.165 | 39.728 | 1.00 | 74.62 |
| ATOM | 814 | CG | GLU | 110 | 30.270 | 30.009 | 38.478 | 1.00 | 85.66 |
| ATOM | 815 | CD | GLU | 110 | 31.096 | 29.287 | 37.423 | 1.00 | 89.36 |
| ATOM | 816 | OE1 | GLU | 110 | 32.257 | 28.928 | 37.714 | 1.00 | 90.28 |
| ATOM | 817 | OE2 | GLU | 110 | 30.585 | 29.080 | 36.300 | 1.00 | 91.15 |
| ATOM | 818 | C | GLU | 110 | 29.073 | 27.101 | 40.782 | 1.00 | 61.70 |
| ATOM | 819 | O | GLU | 110 | 29.984 | 26.342 | 41.116 | 1.00 | 55.88 |
| ATOM | 820 | N | ASN | 111 | 27.973 | 27.286 | 41.505 | 1.00 | 59.69 |
| ATOM | 821 | CA | ASN | 111 | 27.706 | 26.553 | 42.737 | 1.00 | 61.18 |
| ATOM | 822 | CB | ASN | 111 | 27.259 | 27.512 | 43.840 | 1.00 | 68.92 |
| ATOM | 823 | CG | ASN | 111 | 28.365 | 28.456 | 44.267 | 1.00 | 81.46 |
| ATOM | 824 | OD1 | ASN | 111 | 29.298 | 28.062 | 44.968 | 1.00 | 85.51 |
| ATOM | 825 | ND2 | ASN | 111 | 28.275 | 29.706 | 43.831 | 1.00 | 82.65 |
| ATOM | 826 | C | ASN | 111 | 26.588 | 25.576 | 42.387 | 1.00 | 61.11 |
| ATOM | 827 | O | ASN | 111 | 26.159 | 25.515 | 41.235 | 1.00 | 60.30 |
| ATOM | 828 | N | GLY | 112 | 26.101 | 24.820 | 43.361 | 1.00 | 63.31 |
| ATOM | 829 | CA | GLY | 112 | 25.053 | 23.860 | 43.058 | 1.00 | 60.46 |
| ATOM | 830 | C | GLY | 112 | 23.646 | 24.419 | 42.947 | 1.00 | 59.20 |
| ATOM | 831 | O | GLY | 112 | 22.675 | 23.675 | 43.099 | 1.00 | 59.49 |
| ATOM | 832 | N | THR | 113 | 23.517 | 25.712 | 42.667 | 1.00 | 50.68 |
| ATOM | 833 | CA | THR | 113 | 22.191 | 26.313 | 42.573 | 1.00 | 47.52 |
| ATOM | 834 | CB | THR | 113 | 22.220 | 27.838 | 42.915 | 1.00 | 45.45 |
| ATOM | 835 | OG1 | THR | 113 | 22.770 | 28.029 | 44.226 | 1.00 | 48.36 |
| ATOM | 836 | CG2 | THR | 113 | 20.813 | 28.421 | 42.890 | 1.00 | 41.82 |
| ATOM | 837 | C | THR | 113 | 21.533 | 26.133 | 41.211 | 1.00 | 46.90 |
| ATOM | 838 | O | THR | 113 | 22.178 | 26.277 | 40.165 | 1.00 | 46.17 |
| ATOM | 839 | N | LYS | 114 | 20.243 | 25.801 | 41.248 | 1.00 | 46.60 |
| ATOM | 840 | CA | LYS | 114 | 19.422 | 25.619 | 40.051 | 1.00 | 45.98 |

TABLE 2-continued

Atomic coordinates on the three-dimensional crystal structure of the FabK-FMN complex having the amino acid sequences 2-312 of SEQ ID NO: 1

| A | B | C | D | E | F | G | H | I | J |
|---|---|---|---|---|---|---|---|---|---|
| ATOM | 841 | CB | LYS | 114 | 18.389 | 24.516 | 40.288 | 1.00 | 43.46 |
| ATOM | 842 | CG | LYS | 114 | 18.999 | 23.135 | 40.399 | 1.00 | 47.53 |
| ATOM | 843 | CD | LYS | 114 | 19.402 | 22.622 | 39.025 | 1.00 | 49.61 |
| ATOM | 844 | CE | LYS | 114 | 20.656 | 21.784 | 39.097 | 1.00 | 55.30 |
| ATOM | 845 | NZ | LYS | 114 | 21.804 | 22.593 | 39.618 | 1.00 | 60.69 |
| ATOM | 846 | C | LYS | 114 | 18.723 | 26.950 | 39.772 | 1.00 | 41.87 |
| ATOM | 847 | O | LYS | 114 | 18.121 | 27.550 | 40.670 | 1.00 | 43.51 |
| ATOM | 848 | N | VAL | 115 | 18.797 | 27.412 | 38.530 | 1.00 | 32.58 |
| ATOM | 849 | CA | VAL | 115 | 18.199 | 28.690 | 38.186 | 1.00 | 35.09 |
| ATOM | 850 | CB | VAL | 115 | 19.238 | 29.602 | 37.524 | 1.00 | 31.89 |
| ATOM | 851 | CG1 | VAL | 115 | 18.650 | 30.987 | 37.313 | 1.00 | 43.92 |
| ATOM | 852 | CG2 | VAL | 115 | 20.466 | 29.684 | 38.381 | 1.00 | 29.41 |
| ATOM | 853 | C | VAL | 115 | 16.958 | 28.636 | 37.292 | 1.00 | 39.33 |
| ATOM | 854 | O | VAL | 115 | 16.992 | 28.120 | 36.163 | 1.00 | 38.68 |
| ATOM | 855 | N | ILE | 116 | 15.864 | 29.195 | 37.807 | 1.00 | 36.09 |
| ATOM | 856 | CA | ILE | 116 | 14.606 | 29.231 | 37.080 | 1.00 | 31.52 |
| ATOM | 857 | CB | ILE | 116 | 13.467 | 28.516 | 37.843 | 1.00 | 31.29 |
| ATOM | 858 | CG2 | ILE | 116 | 12.352 | 28.162 | 36.878 | 1.00 | 29.74 |
| ATOM | 859 | CG1 | ILE | 116 | 14.005 | 27.274 | 38.563 | 1.00 | 33.56 |
| ATOM | 860 | CD1 | ILE | 116 | 14.522 | 26.226 | 37.647 | 1.00 | 36.10 |
| ATOM | 861 | C | ILE | 116 | 14.175 | 30.673 | 36.883 | 1.00 | 30.48 |
| ATOM | 862 | O | ILE | 116 | 13.545 | 31.279 | 37.754 | 1.00 | 28.42 |
| ATOM | 863 | N | PRO | 117 | 14.547 | 31.258 | 35.748 | 1.00 | 26.96 |
| ATOM | 864 | CD | PRO | 117 | 15.607 | 30.811 | 34.829 | 1.00 | 22.12 |
| ATOM | 865 | CA | PRO | 117 | 14.154 | 32.644 | 35.483 | 1.00 | 29.33 |
| ATOM | 866 | CB | PRO | 117 | 15.113 | 33.067 | 34.372 | 1.00 | 30.98 |
| ATOM | 867 | CG | PRO | 117 | 15.445 | 31.751 | 33.678 | 1.00 | 26.22 |
| ATOM | 868 | C | PRO | 117 | 12.681 | 32.728 | 35.059 | 1.00 | 27.55 |
| ATOM | 869 | O | PRO | 117 | 12.159 | 31.817 | 34.412 | 1.00 | 26.85 |
| ATOM | 870 | N | VAL | 118 | 12.008 | 33.801 | 35.454 | 1.00 | 29.17 |
| ATOM | 871 | CA | VAL | 118 | 10.615 | 33.999 | 35.073 | 1.00 | 29.55 |
| ATOM | 872 | CB | VAL | 118 | 9.864 | 34.877 | 36.076 | 1.00 | 27.06 |
| ATOM | 873 | CG1 | VAL | 118 | 8.439 | 35.113 | 35.593 | 1.00 | 27.75 |
| ATOM | 874 | CG2 | VAL | 118 | 9.859 | 34.210 | 37.419 | 1.00 | 30.46 |
| ATOM | 875 | C | VAL | 118 | 10.603 | 34.688 | 33.713 | 1.00 | 33.19 |
| ATOM | 876 | O | VAL | 118 | 11.299 | 35.685 | 33.501 | 1.00 | 32.68 |
| ATOM | 877 | N | VAL | 119 | 9.792 | 34.156 | 32.802 | 1.00 | 33.87 |
| ATOM | 878 | CA | VAL | 119 | 9.706 | 34.665 | 31.440 | 1.00 | 29.55 |
| ATOM | 879 | CB | VAL | 119 | 10.350 | 33.630 | 30.485 | 1.00 | 38.86 |
| ATOM | 880 | CG1 | VAL | 119 | 9.269 | 32.809 | 29.780 | 1.00 | 28.43 |
| ATOM | 881 | CG2 | VAL | 119 | 11.266 | 34.320 | 29.508 | 1.00 | 44.56 |
| ATOM | 882 | C | VAL | 119 | 8.260 | 34.950 | 30.997 | 1.00 | 29.52 |
| ATOM | 883 | O | VAL | 119 | 7.314 | 34.372 | 31.536 | 1.00 | 23.61 |
| ATOM | 884 | N | ALA | 120 | 8.101 | 35.840 | 30.015 | 1.00 | 31.30 |
| ATOM | 885 | CA | ALA | 120 | 6.781 | 36.201 | 29.478 | 1.00 | 29.31 |
| ATOM | 886 | CB | ALA | 120 | 6.281 | 37.485 | 30.119 | 1.00 | 22.05 |
| ATOM | 887 | C | ALA | 120 | 6.847 | 36.372 | 27.960 | 1.00 | 31.00 |
| ATOM | 888 | O | ALA | 120 | 6.122 | 37.168 | 27.372 | 1.00 | 35.44 |
| ATOM | 889 | N | SER | 121 | 7.730 | 35.607 | 27.337 | 1.00 | 26.36 |
| ATOM | 890 | CA | SER | 121 | 7.921 | 35.642 | 25.904 | 1.00 | 29.70 |
| ATOM | 891 | CB | SER | 121 | 8.536 | 36.978 | 25.484 | 1.00 | 35.24 |
| ATOM | 892 | OG | SER | 121 | 9.870 | 37.094 | 25.948 | 1.00 | 41.34 |
| ATOM | 893 | C | SER | 121 | 8.869 | 34.509 | 25.558 | 1.00 | 28.65 |
| ATOM | 894 | O | SER | 121 | 9.722 | 34.133 | 26.360 | 1.00 | 34.46 |
| ATOM | 895 | N | ASP | 122 | 8.716 | 33.958 | 24.367 | 1.00 | 40.01 |
| ATOM | 896 | CA | ASP | 122 | 9.570 | 32.871 | 23.927 | 1.00 | 41.35 |
| ATOM | 897 | CB | ASP | 122 | 8.986 | 32.241 | 22.670 | 1.00 | 46.89 |
| ATOM | 898 | CG | ASP | 122 | 8.875 | 33.233 | 21.531 | 1.00 | 58.99 |
| ATOM | 899 | OD1 | ASP | 122 | 8.327 | 34.336 | 21.753 | 1.00 | 58.73 |
| ATOM | 900 | OD2 | ASP | 122 | 9.336 | 32.910 | 20.416 | 1.00 | 65.38 |
| ATOM | 901 | C | ASP | 122 | 10.942 | 33.458 | 23.624 | 1.00 | 45.68 |
| ATOM | 902 | O | ASP | 122 | 11.975 | 32.824 | 23.855 | 1.00 | 45.47 |
| ATOM | 903 | N | SER | 123 | 10.942 | 34.680 | 23.102 | 1.00 | 45.67 |
| ATOM | 904 | CA | SER | 123 | 12.183 | 35.353 | 22.756 | 1.00 | 47.96 |
| ATOM | 905 | CB | SER | 123 | 11.901 | 36.785 | 22.308 | 1.00 | 49.41 |
| ATOM | 906 | OG | SER | 123 | 11.424 | 37.558 | 23.390 | 1.00 | 58.37 |
| ATOM | 907 | C | SER | 123 | 13.111 | 35.368 | 23.960 | 1.00 | 45.79 |
| ATOM | 908 | O | SER | 123 | 14.301 | 35.086 | 23.843 | 1.00 | 49.62 |
| ATOM | 909 | N | LEU | 124 | 12.556 | 35.684 | 25.123 | 1.00 | 40.71 |
| ATOM | 910 | CA | LEU | 124 | 13.346 | 35.741 | 26.342 | 1.00 | 40.75 |
| ATOM | 911 | CB | LEU | 124 | 12.618 | 36.561 | 27.410 | 1.00 | 46.75 |
| ATOM | 912 | CG | LEU | 124 | 13.306 | 36.682 | 28.773 | 1.00 | 49.41 |
| ATOM | 913 | CD1 | LEU | 124 | 14.684 | 37.307 | 28.621 | 1.00 | 52.19 |
| ATOM | 914 | CD2 | LEU | 124 | 12.433 | 37.512 | 29.702 | 1.00 | 52.75 |

TABLE 2-continued

Atomic coordinates on the three-dimensional crystal structure of the FabK-
FMN complex having the amino acid sequences 2-312 of SEQ ID NO: 1

| A | B | C | D | E | F | G | H | I | J |
|---|---|---|---|---|---|---|---|---|---|
| ATOM | 915 | C | LEU | 124 | 13.643 | 34.351 | 26.868 | 1.00 | 36.35 |
| ATOM | 916 | O | LEU | 124 | 14.758 | 34.070 | 27.285 | 1.00 | 39.08 |
| ATOM | 917 | N | ALA | 125 | 12.648 | 33.476 | 26.843 | 1.00 | 36.17 |
| ATOM | 918 | CA | ALA | 125 | 12.850 | 32.121 | 27.333 | 1.00 | 36.64 |
| ATOM | 919 | CB | ALA | 125 | 11.623 | 31.259 | 27.025 | 1.00 | 28.64 |
| ATOM | 920 | C | ALA | 125 | 14.102 | 31.508 | 26.706 | 1.00 | 40.09 |
| ATOM | 921 | O | ALA | 125 | 14.992 | 31.026 | 27.412 | 1.00 | 34.02 |
| ATOM | 922 | N | ARG | 126 | 14.175 | 31.537 | 25.380 | 1.00 | 44.65 |
| ATOM | 923 | CA | ARG | 126 | 15.319 | 30.969 | 24.676 | 1.00 | 51.57 |
| ATOM | 924 | CB | ARG | 126 | 15.093 | 31.037 | 23.160 | 1.00 | 64.04 |
| ATOM | 925 | CG | ARG | 126 | 16.105 | 30.247 | 22.324 | 1.00 | 78.54 |
| ATOM | 926 | CD | ARG | 126 | 17.501 | 30.865 | 22.363 | 1.00 | 88.79 |
| ATOM | 927 | NE | ARG | 126 | 18.459 | 30.168 | 21.506 | 1.00 | 99.81 |
| ATOM | 928 | CZ | ARG | 126 | 18.860 | 28.914 | 21.688 | 1.00 | 103.37 |
| ATOM | 929 | NH1 | ARG | 126 | 18.387 | 28.203 | 22.702 | 1.00 | 107.43 |
| ATOM | 930 | NH2 | ARG | 126 | 19.737 | 28.372 | 20.853 | 1.00 | 106.29 |
| ATOM | 931 | C | ARG | 126 | 16.612 | 31.691 | 25.040 | 1.00 | 47.89 |
| ATOM | 932 | O | ARG | 126 | 17.653 | 31.061 | 25.223 | 1.00 | 43.51 |
| ATOM | 933 | N | MET | 127 | 16.538 | 33.013 | 25.149 | 1.00 | 46.51 |
| ATOM | 934 | CA | MET | 127 | 17.708 | 33.821 | 25.479 | 1.00 | 45.44 |
| ATOM | 935 | CB | MET | 127 | 17.320 | 35.299 | 25.544 | 1.00 | 53.18 |
| ATOM | 936 | CG | MET | 127 | 18.479 | 36.276 | 25.432 | 1.00 | 60.89 |
| ATOM | 937 | SD | MET | 127 | 17.895 | 37.952 | 25.041 | 1.00 | 72.16 |
| ATOM | 938 | CE | MET | 127 | 17.679 | 38.642 | 26.694 | 1.00 | 65.86 |
| ATOM | 939 | C | MET | 127 | 18.313 | 33.374 | 26.798 | 1.00 | 39.14 |
| ATOM | 940 | O | MET | 127 | 19.522 | 33.190 | 26.899 | 1.00 | 38.77 |
| ATOM | 941 | N | VAL | 128 | 17.473 | 33.189 | 27.812 | 1.00 | 33.49 |
| ATOM | 942 | CA | VAL | 128 | 17.975 | 32.742 | 29.106 | 1.00 | 25.96 |
| ATOM | 943 | CB | VAL | 128 | 16.928 | 32.944 | 30.236 | 1.00 | 23.38 |
| ATOM | 944 | CG1 | VAL | 128 | 16.435 | 34.362 | 30.218 | 1.00 | 27.65 |
| ATOM | 945 | CG2 | VAL | 128 | 15.776 | 31.972 | 30.091 | 1.00 | 26.23 |
| ATOM | 946 | C | VAL | 128 | 18.383 | 31.266 | 29.032 | 1.00 | 26.50 |
| ATOM | 947 | O | VAL | 128 | 19.245 | 30.814 | 29.781 | 1.00 | 22.84 |
| ATOM | 948 | N | GLU | 129 | 17.771 | 30.521 | 28.117 | 1.00 | 32.07 |
| ATOM | 949 | CA | GLU | 129 | 18.111 | 29.113 | 27.956 | 1.00 | 38.65 |
| ATOM | 950 | CB | GLU | 129 | 17.246 | 28.467 | 26.877 | 1.00 | 41.79 |
| ATOM | 951 | CG | GLU | 129 | 17.446 | 26.965 | 26.781 | 1.00 | 55.76 |
| ATOM | 952 | CD | GLU | 129 | 16.671 | 26.333 | 25.639 | 1.00 | 58.39 |
| ATOM | 953 | OE1 | GLU | 129 | 16.613 | 25.086 | 25.585 | 1.00 | 60.20 |
| ATOM | 954 | OE2 | GLU | 129 | 16.125 | 27.077 | 24.795 | 1.00 | 66.50 |
| ATOM | 955 | C | GLU | 129 | 19.585 | 29.012 | 27.560 | 1.00 | 36.86 |
| ATOM | 956 | O | GLU | 129 | 20.362 | 28.301 | 28.200 | 1.00 | 35.17 |
| ATOM | 957 | N | ARG | 130 | 19.970 | 29.723 | 26.504 | 1.00 | 38.27 |
| ATOM | 958 | CA | ARG | 130 | 21.359 | 29.707 | 26.076 | 1.00 | 45.54 |
| ATOM | 959 | CB | ARG | 130 | 21.542 | 30.497 | 24.780 | 1.00 | 53.90 |
| ATOM | 960 | CG | ARG | 130 | 20.817 | 31.822 | 24.743 | 1.00 | 67.93 |
| ATOM | 961 | CD | ARG | 130 | 21.735 | 32.959 | 24.306 | 1.00 | 77.67 |
| ATOM | 962 | NE | ARG | 130 | 22.565 | 32.620 | 23.149 | 1.00 | 84.40 |
| ATOM | 963 | CZ | ARG | 130 | 22.104 | 32.150 | 21.994 | 1.00 | 84.78 |
| ATOM | 964 | NH1 | ARG | 130 | 20.805 | 31.948 | 21.821 | 1.00 | 85.10 |
| ATOM | 965 | NH2 | ARG | 130 | 22.949 | 31.889 | 21.004 | 1.00 | 88.24 |
| ATOM | 966 | C | ARG | 130 | 22.245 | 30.285 | 27.177 | 1.00 | 46.59 |
| ATOM | 967 | O | ARG | 130 | 23.396 | 29.877 | 27.325 | 1.00 | 51.65 |
| ATOM | 968 | N | ALA | 131 | 21.705 | 31.223 | 27.953 | 1.00 | 46.22 |
| ATOM | 969 | CA | ALA | 131 | 22.452 | 31.836 | 29.049 | 1.00 | 45.87 |
| ATOM | 970 | CB | ALA | 131 | 21.654 | 32.968 | 29.668 | 1.00 | 41.52 |
| ATOM | 971 | C | ALA | 131 | 22.793 | 30.791 | 30.114 | 1.00 | 47.35 |
| ATOM | 972 | O | ALA | 131 | 23.679 | 31.003 | 30.942 | 1.00 | 50.52 |
| ATOM | 973 | N | GLY | 132 | 22.075 | 29.670 | 30.101 | 1.00 | 41.63 |
| ATOM | 974 | CA | GLY | 132 | 22.365 | 28.610 | 31.044 | 1.00 | 36.36 |
| ATOM | 975 | C | GLY | 132 | 21.285 | 28.243 | 32.034 | 1.00 | 38.00 |
| ATOM | 976 | O | GLY | 132 | 21.546 | 27.464 | 32.943 | 1.00 | 36.92 |
| ATOM | 977 | N | ALA | 133 | 20.080 | 28.779 | 31.875 | 1.00 | 38.46 |
| ATOM | 978 | CA | ALA | 133 | 18.991 | 28.471 | 32.805 | 1.00 | 38.10 |
| ATOM | 979 | CB | ALA | 133 | 17.753 | 29.266 | 32.438 | 1.00 | 32.14 |
| ATOM | 980 | C | ALA | 133 | 18.658 | 26.975 | 32.866 | 1.00 | 38.59 |
| ATOM | 981 | O | ALA | 133 | 18.703 | 26.266 | 31.857 | 1.00 | 36.68 |
| ATOM | 982 | N | ASP | 134 | 18.314 | 26.509 | 34.061 | 1.00 | 40.12 |
| ATOM | 983 | CA | ASP | 134 | 17.992 | 25.100 | 34.296 | 1.00 | 46.31 |
| ATOM | 984 | CB | ASP | 134 | 18.217 | 24.775 | 35.774 | 1.00 | 53.11 |
| ATOM | 985 | CG | ASP | 134 | 19.521 | 25.352 | 36.306 | 1.00 | 60.39 |
| ATOM | 986 | OD1 | ASP | 134 | 19.666 | 26.593 | 36.336 | 1.00 | 60.23 |
| ATOM | 987 | OD2 | ASP | 134 | 20.403 | 24.562 | 36.694 | 1.00 | 64.68 |
| ATOM | 988 | C | ASP | 134 | 16.553 | 24.749 | 33.900 | 1.00 | 44.57 |

TABLE 2-continued

Atomic coordinates on the three-dimensional crystal structure of the FabK-FMN complex having the amino acid sequences 2-312 of SEQ ID NO: 1

| A | B | C | D | E | F | G | H | I | J |
|---|---|---|---|---|---|---|---|---|---|
| ATOM | 989 | O | ASP | 134 | 16.230 | 23.593 | 33.615 | 1.00 | 42.15 |
| ATOM | 990 | N | ALA | 135 | 15.704 | 25.768 | 33.895 | 1.00 | 43.18 |
| ATOM | 991 | CA | ALA | 135 | 14.298 | 25.648 | 33.546 | 1.00 | 36.27 |
| ATOM | 992 | CB | ALA | 135 | 13.573 | 24.793 | 34.578 | 1.00 | 39.15 |
| ATOM | 993 | C | ALA | 135 | 13.726 | 27.065 | 33.532 | 1.00 | 34.69 |
| ATOM | 994 | O | ALA | 135 | 14.354 | 28.000 | 34.031 | 1.00 | 34.64 |
| ATOM | 995 | N | VAL | 136 | 12.535 | 27.217 | 32.964 | 1.00 | 33.21 |
| ATOM | 996 | CA | VAL | 136 | 11.891 | 28.520 | 32.878 | 1.00 | 31.59 |
| ATOM | 997 | CB | VAL | 136 | 11.903 | 29.047 | 31.423 | 1.00 | 28.80 |
| ATOM | 998 | CG1 | VAL | 136 | 11.079 | 30.306 | 31.318 | 1.00 | 44.31 |
| ATOM | 999 | CG2 | VAL | 136 | 13.321 | 29.347 | 30.994 | 1.00 | 35.00 |
| ATOM | 1000 | C | VAL | 136 | 10.451 | 28.518 | 33.370 | 1.00 | 29.83 |
| ATOM | 1001 | O | VAL | 136 | 9.721 | 27.534 | 33.232 | 1.00 | 32.43 |
| ATOM | 1002 | N | ILE | 137 | 10.056 | 29.636 | 33.960 | 1.00 | 29.88 |
| ATOM | 1003 | CA | ILE | 137 | 8.695 | 29.814 | 34.441 | 1.00 | 26.34 |
| ATOM | 1004 | CB | ILE | 137 | 8.679 | 30.468 | 35.832 | 1.00 | 27.84 |
| ATOM | 1005 | CG2 | ILE | 137 | 7.245 | 30.890 | 36.208 | 1.00 | 24.81 |
| ATOM | 1006 | CG1 | ILE | 137 | 9.271 | 29.491 | 36.856 | 1.00 | 26.05 |
| ATOM | 1007 | CD1 | ILE | 137 | 9.537 | 30.106 | 38.207 | 1.00 | 26.84 |
| ATOM | 1008 | C | ILE | 137 | 8.003 | 30.744 | 33.455 | 1.00 | 26.96 |
| ATOM | 1009 | O | ILE | 137 | 8.415 | 31.894 | 33.284 | 1.00 | 20.82 |
| ATOM | 1010 | N | ALA | 138 | 6.972 | 30.238 | 32.791 | 1.00 | 22.70 |
| ATOM | 1011 | CA | ALA | 138 | 6.221 | 31.036 | 31.833 | 1.00 | 28.06 |
| ATOM | 1012 | CB | ALA | 138 | 5.809 | 30.176 | 30.629 | 1.00 | 25.62 |
| ATOM | 1013 | C | ALA | 138 | 4.990 | 31.574 | 32.549 | 1.00 | 27.75 |
| ATOM | 1014 | O | ALA | 138 | 4.065 | 30.821 | 32.841 | 1.00 | 31.48 |
| ATOM | 1015 | N | GLU | 139 | 4.986 | 32.872 | 32.843 | 1.00 | 28.34 |
| ATOM | 1016 | CA | GLU | 139 | 3.859 | 33.483 | 33.540 | 1.00 | 28.74 |
| ATOM | 1017 | CB | GLU | 139 | 4.355 | 34.395 | 34.673 | 1.00 | 36.11 |
| ATOM | 1018 | CG | GLU | 139 | 3.281 | 35.359 | 35.191 | 1.00 | 44.78 |
| ATOM | 1019 | CD | GLU | 139 | 3.669 | 36.063 | 36.470 | 1.00 | 47.04 |
| ATOM | 1020 | OE1 | GLU | 139 | 3.101 | 37.144 | 36.756 | 1.00 | 52.01 |
| ATOM | 1021 | OE2 | GLU | 139 | 4.530 | 35.527 | 37.198 | 1.00 | 50.30 |
| ATOM | 1022 | C | GLU | 139 | 2.901 | 34.268 | 32.647 | 1.00 | 22.31 |
| ATOM | 1023 | O | GLU | 139 | 3.257 | 35.313 | 32.100 | 1.00 | 20.52 |
| ATOM | 1024 | N | GLY | 140 | 1.679 | 33.758 | 32.530 | 1.00 | 21.30 |
| ATOM | 1025 | CA | GLY | 140 | 0.660 | 34.415 | 31.734 | 1.00 | 18.73 |
| ATOM | 1026 | C | GLY | 140 | 0.263 | 35.722 | 32.389 | 1.00 | 24.46 |
| ATOM | 1027 | O | GLY | 140 | 0.650 | 36.000 | 33.531 | 1.00 | 28.29 |
| ATOM | 1028 | N | MET | 141 | −0.520 | 36.525 | 31.683 | 1.00 | 19.53 |
| ATOM | 1029 | CA | MET | 141 | −0.925 | 37.818 | 32.204 | 1.00 | 20.77 |
| ATOM | 1030 | CB | MET | 141 | −1.246 | 38.772 | 31.052 | 1.00 | 27.58 |
| ATOM | 1031 | CG | MET | 141 | −2.679 | 38.682 | 30.567 | 1.00 | 34.57 |
| ATOM | 1032 | SD | MET | 141 | −2.957 | 39.845 | 29.238 | 1.00 | 46.85 |
| ATOM | 1033 | CE | MET | 141 | −2.462 | 38.855 | 27.878 | 1.00 | 33.51 |
| ATOM | 1034 | C | MET | 141 | −2.116 | 37.766 | 33.155 | 1.00 | 20.84 |
| ATOM | 1035 | O | MET | 141 | −2.502 | 38.794 | 33.701 | 1.00 | 19.06 |
| ATOM | 1036 | N | GLU | 142 | −2.714 | 36.594 | 33.345 | 1.00 | 17.71 |
| ATOM | 1037 | CA | GLU | 142 | −3.848 | 36.504 | 34.251 | 1.00 | 25.42 |
| ATOM | 1038 | CB | GLU | 142 | −4.801 | 35.369 | 33.845 | 1.00 | 28.10 |
| ATOM | 1039 | CG | GLU | 142 | −4.135 | 33.991 | 33.715 | 1.00 | 33.03 |
| ATOM | 1040 | CD | GLU | 142 | −3.651 | 33.703 | 32.296 | 1.00 | 36.07 |
| ATOM | 1041 | OE1 | GLU | 142 | −2.745 | 34.423 | 31.802 | 1.00 | 28.33 |
| ATOM | 1042 | OE2 | GLU | 142 | −4.190 | 32.758 | 31.682 | 1.00 | 22.20 |
| ATOM | 1043 | C | GLU | 142 | −3.411 | 36.299 | 35.702 | 1.00 | 27.39 |
| ATOM | 1044 | O | GLU | 142 | −4.243 | 36.242 | 36.603 | 1.00 | 30.67 |
| ATOM | 1045 | N | SER | 143 | −2.110 | 36.223 | 35.936 | 1.00 | 22.74 |
| ATOM | 1046 | CA | SER | 143 | −1.620 | 35.997 | 37.286 | 1.00 | 22.77 |
| ATOM | 1047 | CB | SER | 143 | −0.258 | 35.337 | 37.229 | 1.00 | 23.93 |
| ATOM | 1048 | OG | SER | 143 | 0.682 | 36.283 | 36.790 | 1.00 | 16.27 |
| ATOM | 1049 | C | SER | 143 | −1.516 | 37.262 | 38.135 | 1.00 | 27.82 |
| ATOM | 1050 | O | SER | 143 | −1.633 | 38.383 | 37.640 | 1.00 | 24.92 |
| ATOM | 1051 | N | GLY | 144 | −1.279 | 37.066 | 39.426 | 1.00 | 28.55 |
| ATOM | 1052 | CA | GLY | 144 | −1.140 | 38.196 | 40.319 | 1.00 | 31.62 |
| ATOM | 1053 | C | GLY | 144 | 0.250 | 38.784 | 40.213 | 1.00 | 29.09 |
| ATOM | 1054 | O | GLY | 144 | 1.139 | 38.216 | 39.571 | 1.00 | 30.69 |
| ATOM | 1055 | N | GLY | 145 | 0.446 | 39.932 | 40.839 | 1.00 | 27.20 |
| ATOM | 1056 | CA | GLY | 145 | 1.755 | 40.549 | 40.787 | 1.00 | 30.19 |
| ATOM | 1057 | C | GLY | 145 | 2.012 | 41.163 | 39.431 | 1.00 | 30.56 |
| ATOM | 1058 | O | GLY | 145 | 1.068 | 41.455 | 38.683 | 1.00 | 26.90 |
| ATOM | 1059 | N | HIS | 146 | 3.291 | 41.347 | 39.116 | 1.00 | 37.14 |
| ATOM | 1060 | CA | HIS | 146 | 3.715 | 41.924 | 37.844 | 1.00 | 41.75 |
| ATOM | 1061 | CB | HIS | 146 | 5.238 | 42.048 | 37.831 | 1.00 | 55.01 |
| ATOM | 1062 | CG | HIS | 146 | 5.746 | 43.145 | 36.954 | 1.00 | 71.70 |

TABLE 2-continued

Atomic coordinates on the three-dimensional crystal structure of the FabK-
FMN complex having the amino acid sequences 2-312 of SEQ ID NO: 1

| A | B | C | D | E | F | G | H | I | J |
|---|---|---|---|---|---|---|---|---|---|
| ATOM | 1063 | CD2 | HIS | 146 | 6.424 | 43.109 | 35.783 | 1.00 | 75.88 |
| ATOM | 1064 | ND1 | HIS | 146 | 5.559 | 44.477 | 37.250 | 1.00 | 74.66 |
| ATOM | 1065 | CE1 | HIS | 146 | 6.101 | 45.215 | 36.298 | 1.00 | 77.83 |
| ATOM | 1066 | NE2 | HIS | 146 | 6.632 | 44.410 | 35.395 | 1.00 | 78.06 |
| ATOM | 1067 | C | HIS | 146 | 3.257 | 41.018 | 36.696 | 1.00 | 37.70 |
| ATOM | 1068 | O | HIS | 146 | 3.172 | 39.796 | 36.863 | 1.00 | 40.65 |
| ATOM | 1069 | N | ILE | 147 | 2.947 | 41.598 | 35.540 | 1.00 | 27.71 |
| ATOM | 1070 | CA | ILE | 147 | 2.519 | 40.774 | 34.409 | 1.00 | 34.13 |
| ATOM | 1071 | CB | ILE | 147 | 0.984 | 40.746 | 34.256 | 1.00 | 24.69 |
| ATOM | 1072 | CG2 | ILE | 147 | 0.358 | 40.040 | 35.446 | 1.00 | 32.75 |
| ATOM | 1073 | CG1 | ILE | 147 | 0.451 | 42.170 | 34.090 | 1.00 | 31.75 |
| ATOM | 1074 | CD1 | ILE | 147 | −0.954 | 42.224 | 33.540 | 1.00 | 25.14 |
| ATOM | 1075 | C | ILE | 147 | 3.095 | 41.151 | 33.049 | 1.00 | 31.05 |
| ATOM | 1076 | O | ILE | 147 | 3.632 | 42.236 | 32.855 | 1.00 | 40.37 |
| ATOM | 1077 | N | GLY | 148 | 2.965 | 40.226 | 32.109 | 1.00 | 30.63 |
| ATOM | 1078 | CA | GLY | 148 | 3.443 | 40.448 | 30.764 | 1.00 | 30.48 |
| ATOM | 1079 | C | GLY | 148 | 2.262 | 40.702 | 29.849 | 1.00 | 35.30 |
| ATOM | 1080 | O | GLY | 148 | 1.181 | 41.074 | 30.317 | 1.00 | 30.35 |
| ATOM | 1081 | N | GLU | 149 | 2.459 | 40.476 | 28.551 | 1.00 | 35.44 |
| ATOM | 1082 | CA | GLU | 149 | 1.417 | 40.715 | 27.556 | 1.00 | 32.59 |
| ATOM | 1083 | CB | GLU | 149 | 1.986 | 41.506 | 26.372 | 1.00 | 42.18 |
| ATOM | 1084 | CG | GLU | 149 | 1.921 | 43.024 | 26.492 | 1.00 | 58.22 |
| ATOM | 1085 | CD | GLU | 149 | 2.929 | 43.596 | 27.471 | 1.00 | 69.81 |
| ATOM | 1086 | OE1 | GLU | 149 | 3.081 | 44.838 | 27.513 | 1.00 | 76.04 |
| ATOM | 1087 | OE2 | GLU | 149 | 3.567 | 42.810 | 28.201 | 1.00 | 78.77 |
| ATOM | 1088 | C | GLU | 149 | 0.722 | 39.475 | 27.010 | 1.00 | 26.68 |
| ATOM | 1089 | O | GLU | 149 | −0.318 | 39.578 | 26.390 | 1.00 | 34.86 |
| ATOM | 1090 | N | VAL | 150 | 1.283 | 38.301 | 27.216 | 1.00 | 14.80 |
| ATOM | 1091 | CA | VAL | 150 | 0.636 | 37.107 | 26.689 | 1.00 | 23.15 |
| ATOM | 1092 | CB | VAL | 150 | 1.675 | 36.193 | 25.996 | 1.00 | 29.55 |
| ATOM | 1093 | CG1 | VAL | 150 | 0.979 | 35.014 | 25.330 | 1.00 | 27.34 |
| ATOM | 1094 | CG2 | VAL | 150 | 2.461 | 36.996 | 24.968 | 1.00 | 29.78 |
| ATOM | 1095 | C | VAL | 150 | −0.102 | 36.292 | 27.743 | 1.00 | 16.04 |
| ATOM | 1096 | O | VAL | 150 | 0.317 | 36.232 | 28.887 | 1.00 | 21.45 |
| ATOM | 1097 | N | THR | 151 | −1.207 | 35.669 | 27.363 | 1.00 | 19.42 |
| ATOM | 1098 | CA | THR | 151 | −1.954 | 34.835 | 28.305 | 1.00 | 19.80 |
| ATOM | 1099 | CB | THR | 151 | −3.402 | 34.505 | 27.800 | 1.00 | 26.46 |
| ATOM | 1100 | OG1 | THR | 151 | −3.335 | 33.755 | 26.580 | 1.00 | 17.62 |
| ATOM | 1101 | CG2 | THR | 151 | −4.201 | 35.784 | 27.555 | 1.00 | 23.93 |
| ATOM | 1102 | C | THR | 151 | −1.232 | 33.502 | 28.479 | 1.00 | 22.79 |
| ATOM | 1103 | O | THR | 151 | −0.395 | 33.105 | 27.650 | 1.00 | 17.34 |
| ATOM | 1104 | N | THR | 152 | −1.585 | 32.810 | 29.554 | 1.00 | 17.93 |
| ATOM | 1105 | CA | THR | 152 | −1.031 | 31.499 | 29.860 | 1.00 | 28.40 |
| ATOM | 1106 | CB | THR | 152 | −1.600 | 30.935 | 31.178 | 1.00 | 22.09 |
| ATOM | 1107 | OG1 | THR | 152 | −1.074 | 31.671 | 32.280 | 1.00 | 29.39 |
| ATOM | 1108 | CG2 | THR | 152 | −1.237 | 29.467 | 31.330 | 1.00 | 33.19 |
| ATOM | 1109 | C | THR | 152 | −1.331 | 30.466 | 28.775 | 1.00 | 23.70 |
| ATOM | 1110 | O | THR | 152 | −0.448 | 29.714 | 28.382 | 1.00 | 23.46 |
| ATOM | 1111 | N | PHE | 153 | −2.579 | 30.420 | 28.315 | 1.00 | 26.21 |
| ATOM | 1112 | CA | PHE | 153 | −2.976 | 29.448 | 27.301 | 1.00 | 31.60 |
| ATOM | 1113 | CB | PHE | 153 | −4.427 | 29.669 | 26.895 | 1.00 | 31.10 |
| ATOM | 1114 | CG | PHE | 153 | −5.141 | 28.412 | 26.504 | 1.00 | 26.86 |
| ATOM | 1115 | CD1 | PHE | 153 | −5.614 | 27.540 | 27.472 | 1.00 | 35.18 |
| ATOM | 1116 | CD2 | PHE | 153 | −5.363 | 28.112 | 25.171 | 1.00 | 32.30 |
| ATOM | 1117 | CE1 | PHE | 153 | −6.309 | 26.379 | 27.112 | 1.00 | 39.76 |
| ATOM | 1118 | CE2 | PHE | 153 | −6.050 | 26.962 | 24.797 | 1.00 | 31.04 |
| ATOM | 1119 | CZ | PHE | 153 | −6.525 | 26.095 | 25.765 | 1.00 | 36.09 |
| ATOM | 1120 | C | PHE | 153 | −2.093 | 29.507 | 26.056 | 1.00 | 33.55 |
| ATOM | 1121 | O | PHE | 153 | −1.803 | 28.484 | 25.435 | 1.00 | 35.61 |
| ATOM | 1122 | N | VAL | 154 | −1.661 | 30.710 | 25.703 | 1.00 | 28.84 |
| ATOM | 1123 | CA | VAL | 154 | −0.816 | 30.901 | 24.538 | 1.00 | 27.79 |
| ATOM | 1124 | CB | VAL | 154 | −1.066 | 32.286 | 23.913 | 1.00 | 27.77 |
| ATOM | 1125 | CG1 | VAL | 154 | −0.117 | 32.512 | 22.746 | 1.00 | 25.87 |
| ATOM | 1126 | CG2 | VAL | 154 | −2.517 | 32.390 | 23.459 | 1.00 | 26.87 |
| ATOM | 1127 | C | VAL | 154 | 0.679 | 30.776 | 24.825 | 1.00 | 23.99 |
| ATOM | 1128 | O | VAL | 154 | 1.405 | 30.121 | 24.087 | 1.00 | 30.17 |
| ATOM | 1129 | N | LEU | 155 | 1.136 | 31.400 | 25.900 | 1.00 | 16.28 |
| ATOM | 1130 | CA | LEU | 155 | 2.546 | 31.396 | 26.225 | 1.00 | 12.99 |
| ATOM | 1131 | CB | LEU | 155 | 2.789 | 32.355 | 27.372 | 1.00 | 2.58 |
| ATOM | 1132 | CG | LEU | 155 | 4.165 | 32.608 | 27.966 | 1.00 | 16.83 |
| ATOM | 1133 | CD1 | LEU | 155 | 5.042 | 33.381 | 26.964 | 1.00 | 23.43 |
| ATOM | 1134 | CD2 | LEU | 155 | 3.974 | 33.429 | 29.258 | 1.00 | 14.38 |
| ATOM | 1135 | C | LEU | 155 | 3.151 | 30.044 | 26.548 | 1.00 | 22.59 |
| ATOM | 1136 | O | LEU | 155 | 4.205 | 29.702 | 26.012 | 1.00 | 28.36 |

TABLE 2-continued

Atomic coordinates on the three-dimensional crystal structure of the FabK-
FMN complex having the amino acid sequences 2-312 of SEQ ID NO: 1

| A | B | C | D | E | F | G | H | I | J |
|---|---|---|---|---|---|---|---|---|---|
| ATOM | 1137 | N | VAL | 156 | 2.512 | 29.277 | 27.426 | 1.00 | 16.72 |
| ATOM | 1138 | CA | VAL | 156 | 3.061 | 27.972 | 27.776 | 1.00 | 21.28 |
| ATOM | 1139 | CB | VAL | 156 | 2.153 | 27.187 | 28.759 | 1.00 | 26.71 |
| ATOM | 1140 | CG1 | VAL | 156 | 2.680 | 25.762 | 28.932 | 1.00 | 24.84 |
| ATOM | 1141 | CG2 | VAL | 156 | 2.109 | 27.889 | 30.104 | 1.00 | 22.74 |
| ATOM | 1142 | C | VAL | 156 | 3.254 | 27.133 | 26.524 | 1.00 | 25.44 |
| ATOM | 1143 | O | VAL | 156 | 4.239 | 26.411 | 26.403 | 1.00 | 22.56 |
| ATOM | 1144 | N | ASN | 157 | 2.313 | 27.246 | 25.593 | 1.00 | 25.09 |
| ATOM | 1145 | CA | ASN | 157 | 2.366 | 26.500 | 24.347 | 1.00 | 26.61 |
| ATOM | 1146 | CB | ASN | 157 | 1.084 | 26.753 | 23.544 | 1.00 | 23.36 |
| ATOM | 1147 | CG | ASN | 157 | 0.907 | 25.783 | 22.413 | 1.00 | 29.91 |
| ATOM | 1148 | OD1 | ASN | 157 | −0.080 | 25.839 | 21.695 | 1.00 | 43.55 |
| ATOM | 1149 | ND2 | ASN | 157 | 1.865 | 24.883 | 22.243 | 1.00 | 41.23 |
| ATOM | 1150 | C | ASN | 157 | 3.586 | 26.891 | 23.523 | 1.00 | 28.75 |
| ATOM | 1151 | O | ASN | 157 | 4.408 | 26.037 | 23.179 | 1.00 | 33.11 |
| ATOM | 1152 | N | LYS | 158 | 3.703 | 28.188 | 23.231 | 1.00 | 29.62 |
| ATOM | 1153 | CA | LYS | 158 | 4.795 | 28.733 | 22.430 | 1.00 | 28.68 |
| ATOM | 1154 | CB | LYS | 158 | 4.573 | 30.228 | 22.218 | 1.00 | 30.64 |
| ATOM | 1155 | CG | LYS | 158 | 5.054 | 30.755 | 20.877 | 1.00 | 36.67 |
| ATOM | 1156 | CD | LYS | 158 | 6.535 | 30.539 | 20.669 | 1.00 | 35.62 |
| ATOM | 1157 | CE | LYS | 158 | 6.957 | 30.991 | 19.289 | 1.00 | 36.18 |
| ATOM | 1158 | NZ | LYS | 158 | 6.273 | 30.201 | 18.246 | 1.00 | 34.01 |
| ATOM | 1159 | C | LYS | 158 | 6.185 | 28.515 | 23.036 | 1.00 | 30.55 |
| ATOM | 1160 | O | LYS | 158 | 7.111 | 28.078 | 22.353 | 1.00 | 24.89 |
| ATOM | 1161 | N | VAL | 159 | 6.338 | 28.837 | 24.312 | 1.00 | 29.79 |
| ATOM | 1162 | CA | VAL | 159 | 7.621 | 28.663 | 24.975 | 1.00 | 29.50 |
| ATOM | 1163 | CB | VAL | 159 | 7.561 | 29.225 | 26.411 | 1.00 | 33.08 |
| ATOM | 1164 | CG1 | VAL | 159 | 8.843 | 28.903 | 27.156 | 1.00 | 36.90 |
| ATOM | 1165 | CG2 | VAL | 159 | 7.343 | 30.728 | 26.363 | 1.00 | 34.22 |
| ATOM | 1166 | C | VAL | 159 | 8.062 | 27.186 | 24.992 | 1.00 | 25.47 |
| ATOM | 1167 | O | VAL | 159 | 9.248 | 26.892 | 24.872 | 1.00 | 27.89 |
| ATOM | 1168 | N | SER | 160 | 7.111 | 26.266 | 25.130 | 1.00 | 29.77 |
| ATOM | 1169 | CA | SER | 160 | 7.403 | 24.825 | 25.140 | 1.00 | 33.46 |
| ATOM | 1170 | CB | SER | 160 | 6.128 | 24.018 | 25.382 | 1.00 | 31.69 |
| ATOM | 1171 | OG | SER | 160 | 5.916 | 23.807 | 26.759 | 1.00 | 40.23 |
| ATOM | 1172 | C | SER | 160 | 8.025 | 24.340 | 23.832 | 1.00 | 35.15 |
| ATOM | 1173 | O | SER | 160 | 9.007 | 23.592 | 23.829 | 1.00 | 38.05 |
| ATOM | 1174 | N | ARG | 161 | 7.428 | 24.752 | 22.725 | 1.00 | 29.97 |
| ATOM | 1175 | CA | ARG | 161 | 7.913 | 24.373 | 21.413 | 1.00 | 32.86 |
| ATOM | 1176 | CB | ARG | 161 | 6.863 | 24.699 | 20.356 | 1.00 | 34.86 |
| ATOM | 1177 | CG | ARG | 161 | 5.495 | 24.099 | 20.577 | 1.00 | 39.20 |
| ATOM | 1178 | CD | ARG | 161 | 4.511 | 24.813 | 19.675 | 1.00 | 40.93 |
| ATOM | 1179 | NE | ARG | 161 | 3.202 | 24.180 | 19.618 | 1.00 | 44.86 |
| ATOM | 1180 | CZ | ARG | 161 | 2.992 | 22.952 | 19.160 | 1.00 | 56.98 |
| ATOM | 1181 | NH1 | ARG | 161 | 4.014 | 22.226 | 18.731 | 1.00 | 60.38 |
| ATOM | 1182 | NH2 | ARG | 161 | 1.759 | 22.459 | 19.099 | 1.00 | 58.39 |
| ATOM | 1183 | C | ARG | 161 | 9.176 | 25.160 | 21.082 | 1.00 | 37.39 |
| ATOM | 1184 | O | ARG | 161 | 9.789 | 24.950 | 20.034 | 1.00 | 38.75 |
| ATOM | 1185 | N | SER | 162 | 9.571 | 26.076 | 21.957 | 1.00 | 34.51 |
| ATOM | 1186 | CA | SER | 162 | 10.750 | 26.872 | 21.661 | 1.00 | 41.76 |
| ATOM | 1187 | CB | SER | 162 | 10.435 | 28.358 | 21.823 | 1.00 | 36.12 |
| ATOM | 1188 | OG | SER | 162 | 9.481 | 28.765 | 20.857 | 1.00 | 45.98 |
| ATOM | 1189 | C | SER | 162 | 11.986 | 26.519 | 22.466 | 1.00 | 46.25 |
| ATOM | 1190 | O | SER | 162 | 13.100 | 26.766 | 22.008 | 1.00 | 51.16 |
| ATOM | 1191 | N | VAL | 163 | 11.801 | 25.953 | 23.657 | 1.00 | 45.66 |
| ATOM | 1192 | CA | VAL | 163 | 12.945 | 25.577 | 24.482 | 1.00 | 45.85 |
| ATOM | 1193 | CB | VAL | 163 | 13.009 | 26.384 | 25.812 | 1.00 | 42.03 |
| ATOM | 1194 | CG1 | VAL | 163 | 13.171 | 27.872 | 25.512 | 1.00 | 38.64 |
| ATOM | 1195 | CG2 | VAL | 163 | 11.777 | 26.110 | 26.655 | 1.00 | 41.03 |
| ATOM | 1196 | C | VAL | 163 | 12.972 | 24.093 | 24.819 | 1.00 | 48.39 |
| ATOM | 1197 | O | VAL | 163 | 11.933 | 23.440 | 24.970 | 1.00 | 45.27 |
| ATOM | 1198 | N | ASN | 164 | 14.184 | 23.570 | 24.940 | 1.00 | 49.36 |
| ATOM | 1199 | CA | ASN | 164 | 14.370 | 22.170 | 25.249 | 1.00 | 49.46 |
| ATOM | 1200 | CB | ASN | 164 | 15.667 | 21.661 | 24.625 | 1.00 | 63.69 |
| ATOM | 1201 | CG | ASN | 164 | 15.799 | 20.157 | 24.717 | 1.00 | 78.47 |
| ATOM | 1202 | OD1 | ASN | 164 | 15.943 | 19.598 | 25.805 | 1.00 | 83.86 |
| ATOM | 1203 | ND2 | ASN | 164 | 15.740 | 19.490 | 23.570 | 1.00 | 82.07 |
| ATOM | 1204 | C | ASN | 164 | 14.382 | 21.932 | 26.748 | 1.00 | 41.63 |
| ATOM | 1205 | O | ASN | 164 | 14.197 | 20.810 | 27.196 | 1.00 | 41.96 |
| ATOM | 1206 | N | ILE | 165 | 14.599 | 22.982 | 27.528 | 1.00 | 39.34 |
| ATOM | 1207 | CA | ILE | 165 | 14.609 | 22.827 | 28.978 | 1.00 | 38.27 |
| ATOM | 1208 | CB | ILE | 165 | 15.357 | 23.986 | 29.680 | 1.00 | 39.28 |
| ATOM | 1209 | CG2 | ILE | 165 | 16.808 | 24.002 | 29.240 | 1.00 | 45.87 |
| ATOM | 1210 | CG1 | ILE | 165 | 14.689 | 25.322 | 29.362 | 1.00 | 35.69 |

TABLE 2-continued

Atomic coordinates on the three-dimensional crystal structure of the FabK-
FMN complex having the amino acid sequences 2-312 of SEQ ID NO: 1

| A | B | C | D | E | F | G | H | I | J |
|---|---|---|---|---|---|---|---|---|---|
| ATOM | 1211 | CD1 | ILE | 165 | 15.273 | 26.480 | 30.141 | 1.00 | 39.02 |
| ATOM | 1212 | C | ILE | 165 | 13.166 | 22.795 | 29.468 | 1.00 | 35.01 |
| ATOM | 1213 | O | ILE | 165 | 12.264 | 23.204 | 28.754 | 1.00 | 36.91 |
| ATOM | 1214 | N | PRO | 166 | 12.934 | 22.302 | 30.690 | 1.00 | 33.20 |
| ATOM | 1215 | CD | PRO | 166 | 13.914 | 21.684 | 31.596 | 1.00 | 34.80 |
| ATOM | 1216 | CA | PRO | 166 | 11.585 | 22.224 | 31.257 | 1.00 | 38.99 |
| ATOM | 1217 | CB | PRO | 166 | 11.812 | 21.541 | 32.604 | 1.00 | 38.54 |
| ATOM | 1218 | CG | PRO | 166 | 13.056 | 20.726 | 32.369 | 1.00 | 42.11 |
| ATOM | 1219 | C | PRO | 166 | 10.909 | 23.587 | 31.431 | 1.00 | 41.20 |
| ATOM | 1220 | O | PRO | 166 | 11.550 | 24.569 | 31.826 | 1.00 | 34.76 |
| ATOM | 1221 | N | VAL | 167 | 9.610 | 23.630 | 31.139 | 1.00 | 38.65 |
| ATOM | 1222 | CA | VAL | 167 | 8.823 | 24.853 | 31.280 | 1.00 | 32.24 |
| ATOM | 1223 | CB | VAL | 167 | 8.130 | 25.226 | 29.956 | 1.00 | 35.05 |
| ATOM | 1224 | CG1 | VAL | 167 | 7.250 | 26.460 | 30.149 | 1.00 | 33.41 |
| ATOM | 1225 | CG2 | VAL | 167 | 9.175 | 25.480 | 28.886 | 1.00 | 35.09 |
| ATOM | 1226 | C | VAL | 167 | 7.759 | 24.654 | 32.361 | 1.00 | 30.83 |
| ATOM | 1227 | O | VAL | 167 | 7.069 | 23.633 | 32.396 | 1.00 | 35.38 |
| ATOM | 1228 | N | ILE | 168 | 7.636 | 25.640 | 33.240 | 1.00 | 25.17 |
| ATOM | 1229 | CA | ILE | 168 | 6.677 | 25.597 | 34.336 | 1.00 | 25.40 |
| ATOM | 1230 | CB | ILE | 168 | 7.393 | 25.841 | 35.682 | 1.00 | 26.54 |
| ATOM | 1231 | CG2 | ILE | 168 | 6.420 | 25.626 | 36.850 | 1.00 | 28.67 |
| ATOM | 1232 | CG1 | ILE | 168 | 8.586 | 24.891 | 35.799 | 1.00 | 27.47 |
| ATOM | 1233 | CD1 | ILE | 168 | 9.546 | 25.249 | 36.877 | 1.00 | 25.67 |
| ATOM | 1234 | C | ILE | 168 | 5.600 | 26.665 | 34.140 | 1.00 | 20.83 |
| ATOM | 1235 | O | ILE | 168 | 5.883 | 27.858 | 34.156 | 1.00 | 21.06 |
| ATOM | 1236 | N | ALA | 169 | 4.364 | 26.222 | 33.949 | 1.00 | 25.73 |
| ATOM | 1237 | CA | ALA | 169 | 3.237 | 27.121 | 33.745 | 1.00 | 20.75 |
| ATOM | 1238 | CB | ALA | 169 | 2.016 | 26.319 | 33.335 | 1.00 | 21.01 |
| ATOM | 1239 | C | ALA | 169 | 2.963 | 27.851 | 35.046 | 1.00 | 24.60 |
| ATOM | 1240 | O | ALA | 169 | 2.853 | 27.208 | 36.085 | 1.00 | 25.11 |
| ATOM | 1241 | N | ALA | 170 | 2.851 | 29.178 | 34.991 | 1.00 | 29.46 |
| ATOM | 1242 | CA | ALA | 170 | 2.589 | 29.979 | 36.189 | 1.00 | 33.69 |
| ATOM | 1243 | CB | ALA | 170 | 3.762 | 30.911 | 36.456 | 1.00 | 31.45 |
| ATOM | 1244 | C | ALA | 170 | 1.287 | 30.787 | 36.098 | 1.00 | 35.86 |
| ATOM | 1245 | O | ALA | 170 | 0.589 | 30.976 | 37.093 | 1.00 | 42.58 |
| ATOM | 1246 | N | GLY | 171 | 0.966 | 31.265 | 34.906 | 1.00 | 23.83 |
| ATOM | 1247 | CA | GLY | 171 | −0.252 | 32.033 | 34.717 | 1.00 | 39.49 |
| ATOM | 1248 | C | GLY | 171 | −1.399 | 31.937 | 35.722 | 1.00 | 37.28 |
| ATOM | 1249 | O | GLY | 171 | −1.336 | 32.566 | 36.762 | 1.00 | 36.99 |
| ATOM | 1250 | N | GLY | 172 | −2.453 | 31.179 | 35.424 | 1.00 | 30.74 |
| ATOM | 1251 | CA | GLY | 172 | −3.567 | 31.114 | 36.362 | 1.00 | 29.95 |
| ATOM | 1252 | C | GLY | 172 | −4.043 | 29.732 | 36.794 | 1.00 | 39.28 |
| ATOM | 1253 | O | GLY | 172 | −5.157 | 29.296 | 36.439 | 1.00 | 36.14 |
| ATOM | 1254 | N | ILE | 173 | −3.208 | 29.048 | 37.576 | 1.00 | 35.33 |
| ATOM | 1255 | CA | ILE | 173 | −3.524 | 27.716 | 38.063 | 1.00 | 32.95 |
| ATOM | 1256 | CB | ILE | 173 | −2.290 | 26.783 | 37.983 | 1.00 | 30.13 |
| ATOM | 1257 | CG2 | ILE | 173 | −2.624 | 25.442 | 38.623 | 1.00 | 43.26 |
| ATOM | 1258 | CG1 | ILE | 173 | −1.868 | 26.554 | 36.522 | 1.00 | 35.71 |
| ATOM | 1259 | CD1 | ILE | 173 | −1.224 | 27.745 | 35.844 | 1.00 | 32.75 |
| ATOM | 1260 | C | ILE | 173 | −4.001 | 27.755 | 39.514 | 1.00 | 37.56 |
| ATOM | 1261 | O | ILE | 173 | −3.387 | 28.408 | 40.363 | 1.00 | 37.40 |
| ATOM | 1262 | N | ALA | 174 | −5.097 | 27.055 | 39.796 | 1.00 | 29.34 |
| ATOM | 1263 | CA | ALA | 174 | −5.622 | 27.004 | 41.149 | 1.00 | 31.86 |
| ATOM | 1264 | CB | ALA | 174 | −6.657 | 28.100 | 41.360 | 1.00 | 34.25 |
| ATOM | 1265 | C | ALA | 174 | −6.230 | 25.638 | 41.452 | 1.00 | 32.87 |
| ATOM | 1266 | O | ALA | 174 | −6.844 | 25.451 | 42.509 | 1.00 | 34.85 |
| ATOM | 1267 | N | ASP | 175 | −6.051 | 24.685 | 40.537 | 1.00 | 29.58 |
| ATOM | 1268 | CA | ASP | 175 | −6.593 | 23.344 | 40.737 | 1.00 | 35.99 |
| ATOM | 1269 | CB | ASP | 175 | −8.125 | 23.379 | 40.635 | 1.00 | 36.02 |
| ATOM | 1270 | CG | ASP | 175 | −8.616 | 23.884 | 39.292 | 1.00 | 39.08 |
| ATOM | 1271 | OD1 | ASP | 175 | −9.735 | 24.446 | 39.239 | 1.00 | 39.68 |
| ATOM | 1272 | OD2 | ASP | 175 | −7.896 | 23.708 | 38.287 | 1.00 | 41.43 |
| ATOM | 1273 | C | ASP | 175 | −6.024 | 22.290 | 39.792 | 1.00 | 36.91 |
| ATOM | 1274 | O | ASP | 175 | −5.217 | 22.601 | 38.916 | 1.00 | 38.34 |
| ATOM | 1275 | N | GLY | 176 | −6.447 | 21.041 | 39.986 | 1.00 | 34.77 |
| ATOM | 1276 | CA | GLY | 176 | −5.965 | 19.944 | 39.168 | 1.00 | 28.72 |
| ATOM | 1277 | C | GLY | 176 | −6.228 | 20.088 | 37.682 | 1.00 | 34.54 |
| ATOM | 1278 | O | GLY | 176 | −5.413 | 19.662 | 36.857 | 1.00 | 35.71 |
| ATOM | 1279 | N | ARG | 177 | −7.375 | 20.668 | 37.340 | 1.00 | 35.48 |
| ATOM | 1280 | CA | ARG | 177 | −7.748 | 20.893 | 35.948 | 1.00 | 35.02 |
| ATOM | 1281 | CB | ARG | 177 | −9.128 | 21.558 | 35.871 | 1.00 | 38.47 |
| ATOM | 1282 | CG | ARG | 177 | −10.232 | 20.676 | 36.407 | 1.00 | 47.61 |
| ATOM | 1283 | CD | ARG | 177 | −11.498 | 21.438 | 36.726 | 1.00 | 51.80 |
| ATOM | 1284 | NE | ARG | 177 | −12.342 | 21.685 | 35.563 | 1.00 | 61.17 |

TABLE 2-continued

Atomic coordinates on the three-dimensional crystal structure of the FabK-FMN complex having the amino acid sequences 2-312 of SEQ ID NO: 1

| A | B | C | D | E | F | G | H | I | J |
|---|---|---|---|---|---|---|---|---|---|
| ATOM | 1285 | CZ | ARG | 177 | −13.652 | 21.446 | 35.530 | 1.00 | 67.05 |
| ATOM | 1286 | NH1 | ARG | 177 | −14.263 | 20.943 | 36.596 | 1.00 | 64.94 |
| ATOM | 1287 | NH2 | ARG | 177 | −14.358 | 21.732 | 34.440 | 1.00 | 68.69 |
| ATOM | 1288 | C | ARG | 177 | −6.704 | 21.787 | 35.296 | 1.00 | 31.57 |
| ATOM | 1289 | O | ARG | 177 | −6.303 | 21.560 | 34.153 | 1.00 | 34.60 |
| ATOM | 1290 | N | GLY | 178 | −6.264 | 22.797 | 36.042 | 1.00 | 25.08 |
| ATOM | 1291 | CA | GLY | 178 | −5.266 | 23.720 | 35.540 | 1.00 | 20.02 |
| ATOM | 1292 | C | GLY | 178 | −3.944 | 23.021 | 35.307 | 1.00 | 26.43 |
| ATOM | 1293 | O | GLY | 178 | −3.260 | 23.280 | 34.305 | 1.00 | 22.26 |
| ATOM | 1294 | N | MET | 179 | −3.588 | 22.124 | 36.226 | 1.00 | 20.83 |
| ATOM | 1295 | CA | MET | 179 | −2.338 | 21.392 | 36.109 | 1.00 | 28.25 |
| ATOM | 1296 | CB | MET | 179 | −2.105 | 20.480 | 37.324 | 1.00 | 31.90 |
| ATOM | 1297 | CG | MET | 179 | −0.629 | 20.090 | 37.520 | 1.00 | 36.26 |
| ATOM | 1298 | SD | MET | 179 | −0.304 | 18.641 | 38.578 | 1.00 | 31.53 |
| ATOM | 1299 | CE | MET | 179 | −1.106 | 19.114 | 40.022 | 1.00 | 30.45 |
| ATOM | 1300 | C | MET | 179 | −2.397 | 20.545 | 34.846 | 1.00 | 27.71 |
| ATOM | 1301 | O | MET | 179 | −1.427 | 20.467 | 34.087 | 1.00 | 23.41 |
| ATOM | 1302 | N | ALA | 180 | −3.549 | 19.919 | 34.627 | 1.00 | 22.20 |
| ATOM | 1303 | CA | ALA | 180 | −3.742 | 19.082 | 33.464 | 1.00 | 20.07 |
| ATOM | 1304 | CB | ALA | 180 | −5.102 | 18.409 | 33.536 | 1.00 | 24.25 |
| ATOM | 1305 | C | ALA | 180 | −3.613 | 19.920 | 32.192 | 1.00 | 23.41 |
| ATOM | 1306 | O | ALA | 180 | −2.796 | 19.608 | 31.314 | 1.00 | 19.57 |
| ATOM | 1307 | N | ALA | 181 | −4.409 | 20.984 | 32.098 | 1.00 | 19.20 |
| ATOM | 1308 | CA | ALA | 181 | −4.371 | 21.866 | 30.931 | 1.00 | 25.65 |
| ATOM | 1309 | CB | ALA | 181 | −5.279 | 23.110 | 31.148 | 1.00 | 13.29 |
| ATOM | 1310 | C | ALA | 181 | −2.941 | 22.319 | 30.670 | 1.00 | 25.57 |
| ATOM | 1311 | O | ALA | 181 | −2.451 | 22.235 | 29.542 | 1.00 | 24.73 |
| ATOM | 1312 | N | ALA | 182 | −2.281 | 22.792 | 31.725 | 1.00 | 14.27 |
| ATOM | 1313 | CA | ALA | 182 | −0.913 | 23.277 | 31.618 | 1.00 | 19.79 |
| ATOM | 1314 | CB | ALA | 182 | −0.417 | 23.750 | 32.979 | 1.00 | 12.26 |
| ATOM | 1315 | C | ALA | 182 | 0.005 | 22.192 | 31.069 | 1.00 | 24.78 |
| ATOM | 1316 | O | ALA | 182 | 0.870 | 22.466 | 30.224 | 1.00 | 23.58 |
| ATOM | 1317 | N | PHE | 183 | −0.181 | 20.963 | 31.543 | 1.00 | 22.14 |
| ATOM | 1318 | CA | PHE | 183 | 0.647 | 19.870 | 31.071 | 1.00 | 29.98 |
| ATOM | 1319 | CB | PHE | 183 | 0.429 | 18.606 | 31.909 | 1.00 | 36.09 |
| ATOM | 1320 | CG | PHE | 183 | 1.261 | 18.559 | 33.166 | 1.00 | 41.46 |
| ATOM | 1321 | CD1 | PHE | 183 | 1.830 | 17.366 | 33.593 | 1.00 | 49.14 |
| ATOM | 1322 | CD2 | PHE | 183 | 1.485 | 19.709 | 33.918 | 1.00 | 51.36 |
| ATOM | 1323 | CE1 | PHE | 183 | 2.610 | 17.323 | 34.748 | 1.00 | 53.49 |
| ATOM | 1324 | CE2 | PHE | 183 | 2.263 | 19.676 | 35.074 | 1.00 | 44.28 |
| ATOM | 1325 | CZ | PHE | 183 | 2.826 | 18.485 | 35.489 | 1.00 | 50.06 |
| ATOM | 1326 | C | PHE | 183 | 0.357 | 19.596 | 29.612 | 1.00 | 27.26 |
| ATOM | 1327 | O | PHE | 183 | 1.262 | 19.284 | 28.848 | 1.00 | 28.98 |
| ATOM | 1328 | N | ALA | 184 | −0.905 | 19.724 | 29.217 | 1.00 | 26.93 |
| ATOM | 1329 | CA | ALA | 184 | −1.269 | 19.501 | 27.822 | 1.00 | 25.20 |
| ATOM | 1330 | CB | ALA | 184 | −2.784 | 19.557 | 27.654 | 1.00 | 20.89 |
| ATOM | 1331 | C | ALA | 184 | −0.609 | 20.570 | 26.948 | 1.00 | 27.88 |
| ATOM | 1332 | O | ALA | 184 | −0.227 | 20.308 | 25.801 | 1.00 | 25.11 |
| ATOM | 1333 | N | LEU | 185 | −0.481 | 21.776 | 27.503 | 1.00 | 22.68 |
| ATOM | 1334 | CA | LEU | 185 | 0.115 | 22.888 | 26.787 | 1.00 | 23.54 |
| ATOM | 1335 | CB | LEU | 185 | −0.188 | 24.207 | 27.510 | 1.00 | 18.79 |
| ATOM | 1336 | CG | LEU | 185 | −1.647 | 24.672 | 27.396 | 1.00 | 25.92 |
| ATOM | 1337 | CD1 | LEU | 185 | −1.843 | 26.037 | 28.064 | 1.00 | 12.79 |
| ATOM | 1338 | CD2 | LEU | 185 | −2.033 | 24.730 | 25.934 | 1.00 | 17.22 |
| ATOM | 1339 | C | LEU | 185 | 1.621 | 22.706 | 26.624 | 1.00 | 28.37 |
| ATOM | 1340 | O | LEU | 185 | 2.264 | 23.439 | 25.854 | 1.00 | 18.22 |
| ATOM | 1341 | N | GLY | 186 | 2.173 | 21.734 | 27.356 | 1.00 | 23.42 |
| ATOM | 1342 | CA | GLY | 186 | 3.598 | 21.458 | 27.267 | 1.00 | 23.38 |
| ATOM | 1343 | C | GLY | 186 | 4.401 | 21.650 | 28.539 | 1.00 | 22.04 |
| ATOM | 1344 | O | GLY | 186 | 5.591 | 21.352 | 28.569 | 1.00 | 25.71 |
| ATOM | 1345 | N | ALA | 187 | 3.763 | 22.145 | 29.593 | 1.00 | 24.58 |
| ATOM | 1346 | CA | ALA | 187 | 4.446 | 22.367 | 30.862 | 1.00 | 24.38 |
| ATOM | 1347 | CB | ALA | 187 | 3.584 | 23.237 | 31.767 | 1.00 | 29.19 |
| ATOM | 1348 | C | ALA | 187 | 4.767 | 21.044 | 31.561 | 1.00 | 25.83 |
| ATOM | 1349 | O | ALA | 187 | 4.143 | 20.029 | 31.282 | 1.00 | 29.00 |
| ATOM | 1350 | N | GLU | 188 | 5.730 | 21.062 | 32.477 | 1.00 | 29.39 |
| ATOM | 1351 | CA | GLU | 188 | 6.102 | 19.853 | 33.202 | 1.00 | 33.40 |
| ATOM | 1352 | CB | GLU | 188 | 7.501 | 19.412 | 32.775 | 1.00 | 30.29 |
| ATOM | 1353 | CG | GLU | 188 | 7.563 | 19.174 | 31.282 | 1.00 | 42.40 |
| ATOM | 1354 | CD | GLU | 188 | 8.913 | 18.706 | 30.796 | 1.00 | 47.41 |
| ATOM | 1355 | OE1 | GLU | 188 | 9.340 | 17.615 | 31.232 | 1.00 | 55.67 |
| ATOM | 1356 | OE2 | GLU | 188 | 9.538 | 19.422 | 29.976 | 1.00 | 46.34 |
| ATOM | 1357 | C | GLU | 188 | 6.020 | 20.061 | 34.713 | 1.00 | 31.85 |
| ATOM | 1358 | O | GLU | 188 | 6.489 | 19.232 | 35.501 | 1.00 | 26.03 |

TABLE 2-continued

Atomic coordinates on the three-dimensional crystal structure of the FabK-
FMN complex having the amino acid sequences 2-312 of SEQ ID NO: 1

| A | B | C | D | E | F | G | H | I | J |
|---|---|---|---|---|---|---|---|---|---|
| ATOM | 1359 | N | ALA | 189 | 5.407 | 21.178 | 35.098 | 1.00 | 29.15 |
| ATOM | 1360 | CA | ALA | 189 | 5.212 | 21.536 | 36.497 | 1.00 | 22.72 |
| ATOM | 1361 | CB | ALA | 189 | 6.548 | 21.758 | 37.181 | 1.00 | 21.44 |
| ATOM | 1362 | C | ALA | 189 | 4.398 | 22.817 | 36.510 | 1.00 | 28.06 |
| ATOM | 1363 | O | ALA | 189 | 4.216 | 23.449 | 35.474 | 1.00 | 30.22 |
| ATOM | 1364 | N | VAL | 190 | 3.908 | 23.209 | 37.677 | 1.00 | 23.77 |
| ATOM | 1365 | CA | VAL | 190 | 3.125 | 24.424 | 37.764 | 1.00 | 24.80 |
| ATOM | 1366 | CB | VAL | 190 | 1.625 | 24.110 | 37.821 | 1.00 | 27.45 |
| ATOM | 1367 | CG1 | VAL | 190 | 1.233 | 23.301 | 36.594 | 1.00 | 30.20 |
| ATOM | 1368 | CG2 | VAL | 190 | 1.290 | 23.332 | 39.095 | 1.00 | 27.41 |
| ATOM | 1369 | C | VAL | 190 | 3.489 | 25.240 | 38.985 | 1.00 | 27.15 |
| ATOM | 1370 | O | VAL | 190 | 3.851 | 24.703 | 40.024 | 1.00 | 23.07 |
| ATOM | 1371 | N | GLN | 191 | 3.410 | 26.553 | 38.839 | 1.00 | 25.78 |
| ATOM | 1372 | CA | GLN | 191 | 3.686 | 27.446 | 39.942 | 1.00 | 26.26 |
| ATOM | 1373 | CB | GLN | 191 | 4.758 | 28.462 | 39.554 | 1.00 | 26.73 |
| ATOM | 1374 | CG | GLN | 191 | 4.849 | 29.622 | 40.533 | 1.00 | 29.58 |
| ATOM | 1375 | CD | GLN | 191 | 5.933 | 30.621 | 40.181 | 1.00 | 32.15 |
| ATOM | 1376 | OE1 | GLN | 191 | 7.119 | 30.339 | 40.333 | 1.00 | 21.63 |
| ATOM | 1377 | NE2 | GLN | 191 | 5.526 | 31.800 | 39.699 | 1.00 | 30.31 |
| ATOM | 1378 | C | GLN | 191 | 2.382 | 28.160 | 40.309 | 1.00 | 24.25 |
| ATOM | 1379 | O | GLN | 191 | 1.634 | 28.614 | 39.438 | 1.00 | 26.43 |
| ATOM | 1380 | N | MET | 192 | 2.102 | 28.235 | 41.599 | 1.00 | 29.24 |
| ATOM | 1381 | CA | MET | 192 | 0.899 | 28.898 | 42.076 | 1.00 | 29.66 |
| ATOM | 1382 | CB | MET | 192 | −0.079 | 27.885 | 42.670 | 1.00 | 30.84 |
| ATOM | 1383 | CG | MET | 192 | −0.807 | 27.036 | 41.647 | 1.00 | 42.91 |
| ATOM | 1384 | SD | MET | 192 | −1.889 | 25.826 | 42.454 | 1.00 | 27.10 |
| ATOM | 1385 | CE | MET | 192 | −0.828 | 24.404 | 42.362 | 1.00 | 44.18 |
| ATOM | 1386 | C | MET | 192 | 1.259 | 29.904 | 43.143 | 1.00 | 24.75 |
| ATOM | 1387 | O | MET | 192 | 2.136 | 29.657 | 43.971 | 1.00 | 30.37 |
| ATOM | 1388 | N | GLY | 193 | 0.572 | 31.038 | 43.120 | 1.00 | 21.63 |
| ATOM | 1389 | CA | GLY | 193 | 0.809 | 32.068 | 44.103 | 1.00 | 21.32 |
| ATOM | 1390 | C | GLY | 193 | −0.435 | 32.324 | 44.933 | 1.00 | 25.34 |
| ATOM | 1391 | O | GLY | 193 | −0.434 | 32.111 | 46.152 | 1.00 | 24.62 |
| ATOM | 1392 | N | THR | 194 | −1.495 | 32.786 | 44.273 | 1.00 | 22.20 |
| ATOM | 1393 | CA | THR | 194 | −2.751 | 33.083 | 44.941 | 1.00 | 25.69 |
| ATOM | 1394 | CB | THR | 194 | −3.768 | 33.642 | 43.939 | 1.00 | 29.82 |
| ATOM | 1395 | OG1 | THR | 194 | −3.263 | 34.875 | 43.402 | 1.00 | 35.16 |
| ATOM | 1396 | CG2 | THR | 194 | −5.117 | 33.899 | 44.609 | 1.00 | 30.46 |
| ATOM | 1397 | C | THR | 194 | −3.361 | 31.887 | 45.677 | 1.00 | 26.48 |
| ATOM | 1398 | O | THR | 194 | −3.866 | 32.032 | 46.787 | 1.00 | 22.05 |
| ATOM | 1399 | N | ARG | 195 | −3.327 | 30.713 | 45.057 | 1.00 | 27.33 |
| ATOM | 1400 | CA | ARG | 195 | −3.861 | 29.510 | 45.689 | 1.00 | 25.94 |
| ATOM | 1401 | CB | ARG | 195 | −3.664 | 28.303 | 44.760 | 1.00 | 32.85 |
| ATOM | 1402 | CG | ARG | 195 | −3.969 | 26.916 | 45.351 | 1.00 | 33.79 |
| ATOM | 1403 | CD | ARG | 195 | −5.438 | 26.703 | 45.678 | 1.00 | 28.75 |
| ATOM | 1404 | NE | ARG | 195 | −5.796 | 27.294 | 46.963 | 1.00 | 41.78 |
| ATOM | 1405 | CZ | ARG | 195 | −6.977 | 27.152 | 47.562 | 1.00 | 45.79 |
| ATOM | 1406 | NH1 | ARG | 195 | −7.940 | 26.433 | 46.993 | 1.00 | 51.15 |
| ATOM | 1407 | NH2 | ARG | 195 | −7.194 | 27.717 | 48.743 | 1.00 | 45.36 |
| ATOM | 1408 | C | ARG | 195 | −3.143 | 29.269 | 47.022 | 1.00 | 28.84 |
| ATOM | 1409 | O | ARG | 195 | −3.748 | 28.813 | 47.986 | 1.00 | 26.48 |
| ATOM | 1410 | N | PHE | 196 | −1.854 | 29.584 | 47.079 | 1.00 | 26.77 |
| ATOM | 1411 | CA | PHE | 196 | −1.100 | 29.366 | 48.302 | 1.00 | 31.40 |
| ATOM | 1412 | CB | PHE | 196 | 0.359 | 29.068 | 47.982 | 1.00 | 29.58 |
| ATOM | 1413 | CG | PHE | 196 | 0.612 | 27.642 | 47.608 | 1.00 | 30.59 |
| ATOM | 1414 | CD1 | PHE | 196 | 1.484 | 27.326 | 46.565 | 1.00 | 29.66 |
| ATOM | 1415 | CD2 | PHE | 196 | −0.019 | 26.609 | 48.301 | 1.00 | 26.51 |
| ATOM | 1416 | CE1 | PHE | 196 | 1.724 | 25.996 | 46.214 | 1.00 | 24.01 |
| ATOM | 1417 | CE2 | PHE | 196 | 0.213 | 25.276 | 47.959 | 1.00 | 29.89 |
| ATOM | 1418 | CZ | PHE | 196 | 1.086 | 24.967 | 46.912 | 1.00 | 29.31 |
| ATOM | 1419 | C | PHE | 196 | −1.181 | 30.488 | 49.310 | 1.00 | 34.11 |
| ATOM | 1420 | O | PHE | 196 | −0.614 | 30.388 | 50.387 | 1.00 | 44.94 |
| ATOM | 1421 | N | VAL | 197 | −1.861 | 31.569 | 48.965 | 1.00 | 30.91 |
| ATOM | 1422 | CA | VAL | 197 | −2.023 | 32.665 | 49.909 | 1.00 | 31.71 |
| ATOM | 1423 | CB | VAL | 197 | −2.196 | 34.025 | 49.187 | 1.00 | 35.27 |
| ATOM | 1424 | CG1 | VAL | 197 | −2.700 | 35.073 | 50.165 | 1.00 | 28.67 |
| ATOM | 1425 | CG2 | VAL | 197 | −0.864 | 34.468 | 48.579 | 1.00 | 32.10 |
| ATOM | 1426 | C | VAL | 197 | −3.307 | 32.304 | 50.658 | 1.00 | 37.11 |
| ATOM | 1427 | O | VAL | 197 | −3.453 | 32.568 | 51.858 | 1.00 | 32.45 |
| ATOM | 1428 | N | ALA | 198 | −4.224 | 31.677 | 49.921 | 1.00 | 37.44 |
| ATOM | 1429 | CA | ALA | 198 | −5.505 | 31.231 | 50.451 | 1.00 | 38.99 |
| ATOM | 1430 | CB | ALA | 198 | −6.532 | 31.150 | 49.329 | 1.00 | 34.05 |
| ATOM | 1431 | C | ALA | 198 | −5.345 | 29.864 | 51.128 | 1.00 | 40.98 |
| ATOM | 1432 | O | ALA | 198 | −6.047 | 28.901 | 50.809 | 1.00 | 37.45 |

TABLE 2-continued

Atomic coordinates on the three-dimensional crystal structure of the FabK-
FMN complex having the amino acid sequences 2-312 of SEQ ID NO: 1

| A | B | C | D | E | F | G | H | I | J |
|---|---|---|---|---|---|---|---|---|---|
| ATOM | 1433 | N | SER | 199 | −4.394 | 29.790 | 52.054 | 1.00 | 38.63 |
| ATOM | 1434 | CA | SER | 199 | −4.139 | 28.573 | 52.805 | 1.00 | 40.11 |
| ATOM | 1435 | CB | SER | 199 | −2.819 | 27.932 | 52.383 | 1.00 | 27.94 |
| ATOM | 1436 | OG | SER | 199 | −1.727 | 28.792 | 52.659 | 1.00 | 31.69 |
| ATOM | 1437 | C | SER | 199 | −4.055 | 28.982 | 54.267 | 1.00 | 45.18 |
| ATOM | 1438 | O | SER | 199 | −3.787 | 30.145 | 54.585 | 1.00 | 40.06 |
| ATOM | 1439 | N | VAL | 200 | −4.283 | 28.032 | 55.159 | 1.00 | 48.50 |
| ATOM | 1440 | CA | VAL | 200 | −4.228 | 28.350 | 56.571 | 1.00 | 53.49 |
| ATOM | 1441 | CB | VAL | 200 | −4.824 | 27.199 | 57.419 | 1.00 | 50.08 |
| ATOM | 1442 | CG1 | VAL | 200 | −6.345 | 27.194 | 57.272 | 1.00 | 42.74 |
| ATOM | 1443 | CG2 | VAL | 200 | −4.264 | 25.871 | 56.965 | 1.00 | 52.46 |
| ATOM | 1444 | C | VAL | 200 | −2.807 | 28.675 | 57.018 | 1.00 | 50.65 |
| ATOM | 1445 | O | VAL | 200 | −2.588 | 29.663 | 57.708 | 1.00 | 53.86 |
| ATOM | 1446 | N | GLU | 201 | −1.840 | 27.870 | 56.599 | 1.00 | 53.34 |
| ATOM | 1447 | CA | GLU | 201 | −0.452 | 28.096 | 56.991 | 1.00 | 57.14 |
| ATOM | 1448 | CB | GLU | 201 | 0.478 | 27.118 | 56.263 | 1.00 | 64.50 |
| ATOM | 1449 | CG | GLU | 201 | 0.248 | 25.649 | 56.619 | 1.00 | 74.84 |
| ATOM | 1450 | CD | GLU | 201 | −0.837 | 24.991 | 55.779 | 1.00 | 81.13 |
| ATOM | 1451 | OE1 | GLU | 201 | −1.808 | 25.684 | 55.404 | 1.00 | 84.41 |
| ATOM | 1452 | OE2 | GLU | 201 | −0.725 | 23.776 | 55.504 | 1.00 | 84.17 |
| ATOM | 1453 | C | GLU | 201 | 0.037 | 29.531 | 56.774 | 1.00 | 59.61 |
| ATOM | 1454 | O | GLU | 201 | 0.536 | 30.167 | 57.705 | 1.00 | 62.06 |
| ATOM | 1455 | N | SER | 202 | −0.100 | 30.049 | 55.558 | 1.00 | 59.76 |
| ATOM | 1456 | CA | SER | 202 | 0.354 | 31.411 | 55.280 | 1.00 | 59.32 |
| ATOM | 1457 | CB | SER | 202 | 0.033 | 31.816 | 53.831 | 1.00 | 61.13 |
| ATOM | 1458 | OG | SER | 202 | −1.351 | 32.075 | 53.658 | 1.00 | 51.00 |
| ATOM | 1459 | C | SER | 202 | −0.316 | 32.401 | 56.218 | 1.00 | 56.13 |
| ATOM | 1460 | O | SER | 202 | −1.501 | 32.282 | 56.508 | 1.00 | 55.90 |
| ATOM | 1461 | N | ASP | 203 | 0.442 | 33.373 | 56.703 | 1.00 | 55.32 |
| ATOM | 1462 | CA | ASP | 203 | −0.143 | 34.372 | 57.575 | 1.00 | 60.95 |
| ATOM | 1463 | CB | ASP | 203 | 0.934 | 35.092 | 58.389 | 1.00 | 69.28 |
| ATOM | 1464 | CG | ASP | 203 | 2.196 | 35.330 | 57.602 | 1.00 | 72.95 |
| ATOM | 1465 | OD1 | ASP | 203 | 2.152 | 36.111 | 56.630 | 1.00 | 78.60 |
| ATOM | 1466 | OD2 | ASP | 203 | 3.234 | 34.730 | 57.957 | 1.00 | 73.86 |
| ATOM | 1467 | C | ASP | 203 | −0.870 | 35.333 | 56.658 | 1.00 | 61.96 |
| ATOM | 1468 | O | ASP | 203 | −1.837 | 34.940 | 56.000 | 1.00 | 67.74 |
| ATOM | 1469 | N | VAL | 204 | −0.408 | 36.575 | 56.583 | 1.00 | 55.40 |
| ATOM | 1470 | CA | VAL | 204 | −1.070 | 37.545 | 55.719 | 1.00 | 55.07 |
| ATOM | 1471 | CB | VAL | 204 | −1.284 | 36.967 | 54.281 | 1.00 | 50.45 |
| ATOM | 1472 | CG1 | VAL | 204 | −2.108 | 37.917 | 53.446 | 1.00 | 51.89 |
| ATOM | 1473 | CG2 | VAL | 204 | 0.054 | 36.719 | 53.620 | 1.00 | 50.98 |
| ATOM | 1474 | C | VAL | 204 | −2.419 | 37.890 | 56.354 | 1.00 | 55.11 |
| ATOM | 1475 | O | VAL | 204 | −3.224 | 37.007 | 56.654 | 1.00 | 52.27 |
| ATOM | 1476 | N | HIS | 205 | −2.648 | 39.180 | 56.566 | 1.00 | 55.96 |
| ATOM | 1477 | CA | HIS | 205 | −3.879 | 39.649 | 57.176 | 1.00 | 61.47 |
| ATOM | 1478 | CB | HIS | 205 | −4.124 | 41.109 | 56.789 | 1.00 | 67.03 |
| ATOM | 1479 | CG | HIS | 205 | −5.085 | 41.820 | 57.690 | 1.00 | 73.55 |
| ATOM | 1480 | CD2 | HIS | 205 | −4.911 | 42.874 | 58.522 | 1.00 | 74.89 |
| ATOM | 1481 | ND1 | HIS | 205 | −6.408 | 41.455 | 57.807 | 1.00 | 78.14 |
| ATOM | 1482 | CE1 | HIS | 205 | −7.009 | 42.256 | 58.670 | 1.00 | 76.44 |
| ATOM | 1483 | NE2 | HIS | 205 | −6.122 | 43.126 | 59.118 | 1.00 | 73.73 |
| ATOM | 1484 | C | HIS | 205 | −5.069 | 38.783 | 56.761 | 1.00 | 62.89 |
| ATOM | 1485 | O | HIS | 205 | −5.206 | 38.395 | 55.603 | 1.00 | 62.19 |
| ATOM | 1486 | N | PRO | 206 | −5.942 | 38.452 | 57.714 | 1.00 | 67.72 |
| ATOM | 1487 | CD | PRO | 206 | −5.885 | 38.735 | 59.157 | 1.00 | 69.04 |
| ATOM | 1488 | CA | PRO | 206 | −7.103 | 37.626 | 57.389 | 1.00 | 67.43 |
| ATOM | 1489 | CB | PRO | 206 | −7.900 | 37.646 | 58.683 | 1.00 | 69.06 |
| ATOM | 1490 | CG | PRO | 206 | −6.817 | 37.692 | 59.718 | 1.00 | 69.76 |
| ATOM | 1491 | C | PRO | 206 | −7.893 | 38.177 | 56.214 | 1.00 | 65.30 |
| ATOM | 1492 | O | PRO | 206 | −8.263 | 37.435 | 55.309 | 1.00 | 65.88 |
| ATOM | 1493 | N | VAL | 207 | −8.140 | 39.483 | 56.232 | 1.00 | 63.07 |
| ATOM | 1494 | CA | VAL | 207 | −8.900 | 40.135 | 55.171 | 1.00 | 65.43 |
| ATOM | 1495 | CB | VAL | 207 | −8.809 | 41.673 | 55.285 | 1.00 | 66.83 |
| ATOM | 1496 | CG1 | VAL | 207 | −9.467 | 42.320 | 54.078 | 1.00 | 65.66 |
| ATOM | 1497 | CG2 | VAL | 207 | −9.493 | 42.143 | 56.570 | 1.00 | 61.55 |
| ATOM | 1498 | C | VAL | 207 | −8.455 | 39.711 | 53.771 | 1.00 | 62.97 |
| ATOM | 1499 | O | VAL | 207 | −9.290 | 39.416 | 52.913 | 1.00 | 64.42 |
| ATOM | 1500 | N | TYR | 208 | −7.145 | 39.690 | 53.544 | 1.00 | 56.10 |
| ATOM | 1501 | CA | TYR | 208 | −6.595 | 39.286 | 52.252 | 1.00 | 49.50 |
| ATOM | 1502 | CB | TYR | 208 | −5.080 | 39.117 | 52.370 | 1.00 | 44.29 |
| ATOM | 1503 | CG | TYR | 208 | −4.284 | 39.530 | 51.151 | 1.00 | 39.89 |
| ATOM | 1504 | CD1 | TYR | 208 | −4.551 | 38.988 | 49.899 | 1.00 | 35.89 |
| ATOM | 1505 | CE1 | TYR | 208 | −3.791 | 39.340 | 48.784 | 1.00 | 40.74 |
| ATOM | 1506 | CD2 | TYR | 208 | −3.234 | 40.442 | 51.263 | 1.00 | 44.08 |

TABLE 2-continued

Atomic coordinates on the three-dimensional crystal structure of the FabK-
FMN complex having the amino acid sequences 2-312 of SEQ ID NO: 1

| A | B | C | D | E | F | G | H | I | J |
|---|---|---|---|---|---|---|---|---|---|
| ATOM | 1507 | CE2 | TYR | 208 | −2.466 | 40.803 | 50.154 | 1.00 | 43.00 |
| ATOM | 1508 | CZ | TYR | 208 | −2.750 | 40.249 | 48.916 | 1.00 | 44.44 |
| ATOM | 1509 | OH | TYR | 208 | −2.002 | 40.609 | 47.816 | 1.00 | 35.01 |
| ATOM | 1510 | C | TYR | 208 | −7.237 | 37.959 | 51.822 | 1.00 | 48.58 |
| ATOM | 1511 | O | TYR | 208 | −7.861 | 37.875 | 50.762 | 1.00 | 48.28 |
| ATOM | 1512 | N | LYS | 209 | −7.095 | 36.932 | 52.658 | 1.00 | 41.49 |
| ATOM | 1513 | CA | LYS | 209 | −7.662 | 35.616 | 52.372 | 1.00 | 43.65 |
| ATOM | 1514 | CB | LYS | 209 | −7.418 | 34.666 | 53.544 | 1.00 | 35.91 |
| ATOM | 1515 | CG | LYS | 209 | −5.956 | 34.440 | 53.873 | 1.00 | 41.06 |
| ATOM | 1516 | CD | LYS | 209 | −5.792 | 33.275 | 54.831 | 1.00 | 42.39 |
| ATOM | 1517 | CE | LYS | 209 | −4.375 | 33.189 | 55.341 | 1.00 | 38.07 |
| ATOM | 1518 | NZ | LYS | 209 | −4.247 | 32.123 | 56.362 | 1.00 | 38.56 |
| ATOM | 1519 | C | LYS | 209 | −9.157 | 35.663 | 52.096 | 1.00 | 48.96 |
| ATOM | 1520 | O | LYS | 209 | −9.674 | 34.938 | 51.243 | 1.00 | 47.59 |
| ATOM | 1521 | N | GLU | 210 | −9.859 | 36.512 | 52.835 | 1.00 | 53.38 |
| ATOM | 1522 | CA | GLU | 210 | −11.297 | 36.632 | 52.673 | 1.00 | 56.27 |
| ATOM | 1523 | CB | GLU | 210 | −11.861 | 37.575 | 53.733 | 1.00 | 75.45 |
| ATOM | 1524 | CG | GLU | 210 | −11.104 | 37.519 | 55.056 | 1.00 | 99.07 |
| ATOM | 1525 | CD | GLU | 210 | −10.982 | 36.111 | 55.627 | 1.00 | 108.94 |
| ATOM | 1526 | OE1 | GLU | 210 | −10.293 | 35.946 | 56.658 | 1.00 | 112.34 |
| ATOM | 1527 | OE2 | GLU | 210 | −11.573 | 35.172 | 55.052 | 1.00 | 115.04 |
| ATOM | 1528 | C | GLU | 210 | −11.599 | 37.163 | 51.289 | 1.00 | 46.98 |
| ATOM | 1529 | O | GLU | 210 | −12.441 | 36.618 | 50.576 | 1.00 | 42.59 |
| ATOM | 1530 | N | LYS | 211 | −10.896 | 38.227 | 50.916 | 1.00 | 41.54 |
| ATOM | 1531 | CA | LYS | 211 | −11.065 | 38.854 | 49.604 | 1.00 | 40.40 |
| ATOM | 1532 | CB | LYS | 211 | −10.054 | 39.986 | 49.438 | 1.00 | 39.89 |
| ATOM | 1533 | CG | LYS | 211 | −10.316 | 41.188 | 50.324 | 1.00 | 39.74 |
| ATOM | 1534 | CD | LYS | 211 | −11.629 | 41.857 | 49.942 | 1.00 | 49.06 |
| ATOM | 1535 | CE | LYS | 211 | −11.775 | 43.217 | 50.600 | 1.00 | 49.40 |
| ATOM | 1536 | NZ | LYS | 211 | −12.997 | 43.937 | 50.134 | 1.00 | 54.64 |
| ATOM | 1537 | C | LYS | 211 | −10.890 | 37.844 | 48.474 | 1.00 | 38.35 |
| ATOM | 1538 | O | LYS | 211 | −11.681 | 37.800 | 47.535 | 1.00 | 41.32 |
| ATOM | 1539 | N | ILE | 212 | −9.850 | 37.029 | 48.582 | 1.00 | 32.14 |
| ATOM | 1540 | CA | ILE | 212 | −9.552 | 36.007 | 47.583 | 1.00 | 39.98 |
| ATOM | 1541 | CB | ILE | 212 | −8.240 | 35.273 | 47.952 | 1.00 | 39.58 |
| ATOM | 1542 | CG2 | ILE | 212 | −7.997 | 34.111 | 47.003 | 1.00 | 38.40 |
| ATOM | 1543 | CG1 | ILE | 212 | −7.085 | 36.284 | 47.932 | 1.00 | 39.09 |
| ATOM | 1544 | CD1 | ILE | 212 | −5.725 | 35.703 | 48.246 | 1.00 | 45.47 |
| ATOM | 1545 | C | ILE | 212 | −10.696 | 35.000 | 47.427 | 1.00 | 39.78 |
| ATOM | 1546 | O | ILE | 212 | −11.100 | 34.650 | 46.312 | 1.00 | 35.76 |
| ATOM | 1547 | N | VAL | 213 | −11.223 | 34.543 | 48.553 | 1.00 | 44.26 |
| ATOM | 1548 | CA | VAL | 213 | −12.329 | 33.608 | 48.536 | 1.00 | 41.01 |
| ATOM | 1549 | CB | VAL | 213 | −12.758 | 33.260 | 49.967 | 1.00 | 42.35 |
| ATOM | 1550 | CG1 | VAL | 213 | −14.063 | 32.484 | 49.942 | 1.00 | 42.26 |
| ATOM | 1551 | CG2 | VAL | 213 | −11.658 | 32.452 | 50.647 | 1.00 | 31.52 |
| ATOM | 1552 | C | VAL | 213 | −13.502 | 34.253 | 47.806 | 1.00 | 45.50 |
| ATOM | 1553 | O | VAL | 213 | −13.885 | 33.824 | 46.714 | 1.00 | 52.39 |
| ATOM | 1554 | N | LYS | 214 | −14.044 | 35.306 | 48.410 | 1.00 | 47.35 |
| ATOM | 1555 | CA | LYS | 214 | −15.183 | 36.026 | 47.863 | 1.00 | 53.01 |
| ATOM | 1556 | CB | LYS | 214 | −15.776 | 36.935 | 48.940 | 1.00 | 56.31 |
| ATOM | 1557 | CG | LYS | 214 | −14.761 | 37.876 | 49.546 | 1.00 | 65.44 |
| ATOM | 1558 | CD | LYS | 214 | −15.266 | 38.529 | 50.819 | 1.00 | 72.86 |
| ATOM | 1559 | CE | LYS | 214 | −14.161 | 39.366 | 51.459 | 1.00 | 79.55 |
| ATOM | 1560 | NZ | LYS | 214 | −14.583 | 40.029 | 52.726 | 1.00 | 82.21 |
| ATOM | 1561 | C | LYS | 214 | −14.853 | 36.846 | 46.621 | 1.00 | 53.89 |
| ATOM | 1562 | O | LYS | 214 | −15.557 | 37.802 | 46.298 | 1.00 | 58.83 |
| ATOM | 1563 | N | ALA | 215 | −13.791 | 36.476 | 45.916 | 1.00 | 52.22 |
| ATOM | 1564 | CA | ALA | 215 | −13.413 | 37.205 | 44.711 | 1.00 | 50.48 |
| ATOM | 1565 | CB | ALA | 215 | −11.924 | 37.492 | 44.716 | 1.00 | 46.66 |
| ATOM | 1566 | C | ALA | 215 | −13.782 | 36.425 | 43.463 | 1.00 | 46.44 |
| ATOM | 1567 | O | ALA | 215 | −13.584 | 35.210 | 43.395 | 1.00 | 47.45 |
| ATOM | 1568 | N | SER | 216 | −14.320 | 37.139 | 42.479 | 1.00 | 43.68 |
| ATOM | 1569 | CA | SER | 216 | −14.715 | 36.536 | 41.212 | 1.00 | 40.51 |
| ATOM | 1570 | CB | SER | 216 | −15.923 | 37.271 | 40.619 | 1.00 | 42.91 |
| ATOM | 1571 | OG | SER | 216 | −15.582 | 38.592 | 40.230 | 1.00 | 48.79 |
| ATOM | 1572 | C | SER | 216 | −13.545 | 36.606 | 40.233 | 1.00 | 36.96 |
| ATOM | 1573 | O | SER | 216 | −12.522 | 37.226 | 40.517 | 1.00 | 31.04 |
| ATOM | 1574 | N | ILE | 217 | −13.708 | 35.970 | 39.078 | 1.00 | 33.91 |
| ATOM | 1575 | CA | ILE | 217 | −12.670 | 35.954 | 38.065 | 1.00 | 29.72 |
| ATOM | 1576 | CB | ILE | 217 | −12.946 | 34.868 | 37.022 | 1.00 | 32.35 |
| ATOM | 1577 | CG2 | ILE | 217 | −12.915 | 33.502 | 37.688 | 1.00 | 38.18 |
| ATOM | 1578 | CG1 | ILE | 217 | −14.311 | 35.106 | 36.366 | 1.00 | 35.90 |
| ATOM | 1579 | CD1 | ILE | 217 | −14.708 | 34.057 | 35.352 | 1.00 | 38.98 |
| ATOM | 1580 | C | ILE | 217 | −12.593 | 37.298 | 37.362 | 1.00 | 36.70 |

TABLE 2-continued

Atomic coordinates on the three-dimensional crystal structure of the FabK-
FMN complex having the amino acid sequences 2-312 of SEQ ID NO: 1

| A | B | C | D | E | F | G | H | I | J |
|---|---|---|---|---|---|---|---|---|---|
| ATOM | 1581 | O | ILE | 217 | −11.721 | 37.517 | 36.522 | 1.00 | 35.09 |
| ATOM | 1582 | N | ARG | 218 | −13.511 | 38.193 | 37.715 | 1.00 | 39.06 |
| ATOM | 1583 | CA | ARG | 218 | −13.569 | 39.529 | 37.128 | 1.00 | 39.36 |
| ATOM | 1584 | CB | ARG | 218 | −15.009 | 39.875 | 36.753 | 1.00 | 37.44 |
| ATOM | 1585 | CG | ARG | 218 | −15.495 | 39.260 | 35.468 | 1.00 | 49.83 |
| ATOM | 1586 | CD | ARG | 218 | −17.004 | 39.230 | 35.436 | 1.00 | 54.85 |
| ATOM | 1587 | NE | ARG | 218 | −17.533 | 38.172 | 36.293 | 1.00 | 62.18 |
| ATOM | 1588 | CZ | ARG | 218 | −18.830 | 37.946 | 36.473 | 1.00 | 66.60 |
| ATOM | 1589 | NH1 | ARG | 218 | −19.720 | 38.713 | 35.856 | 1.00 | 68.42 |
| ATOM | 1590 | NH2 | ARG | 218 | −19.237 | 36.949 | 37.248 | 1.00 | 66.70 |
| ATOM | 1591 | C | ARG | 218 | −13.065 | 40.591 | 38.091 | 1.00 | 40.63 |
| ATOM | 1592 | O | ARG | 218 | −12.754 | 41.710 | 37.685 | 1.00 | 43.84 |
| ATOM | 1593 | N | ASP | 219 | −12.978 | 40.236 | 39.366 | 1.00 | 37.99 |
| ATOM | 1594 | CA | ASP | 219 | −12.563 | 41.186 | 40.384 | 1.00 | 40.09 |
| ATOM | 1595 | CB | ASP | 219 | −12.951 | 40.657 | 41.768 | 1.00 | 47.61 |
| ATOM | 1596 | CG | ASP | 219 | −14.459 | 40.474 | 41.922 | 1.00 | 59.78 |
| ATOM | 1597 | OD1 | ASP | 219 | −15.221 | 41.336 | 41.431 | 1.00 | 56.02 |
| ATOM | 1598 | OD2 | ASP | 219 | −14.881 | 39.476 | 42.545 | 1.00 | 57.13 |
| ATOM | 1599 | C | ASP | 219 | −11.106 | 41.634 | 40.393 | 1.00 | 37.33 |
| ATOM | 1600 | O | ASP | 219 | −10.586 | 42.008 | 41.445 | 1.00 | 39.22 |
| ATOM | 1601 | N | THR | 220 | −10.442 | 41.604 | 39.241 | 1.00 | 34.29 |
| ATOM | 1602 | CA | THR | 220 | −9.051 | 42.064 | 39.181 | 1.00 | 32.20 |
| ATOM | 1603 | CB | THR | 220 | −8.057 | 40.921 | 38.795 | 1.00 | 36.04 |
| ATOM | 1604 | OG1 | THR | 220 | −8.050 | 40.739 | 37.376 | 1.00 | 31.40 |
| ATOM | 1605 | CG2 | THR | 220 | −8.458 | 39.609 | 39.471 | 1.00 | 37.80 |
| ATOM | 1606 | C | THR | 220 | −8.905 | 43.207 | 38.172 | 1.00 | 25.53 |
| ATOM | 1607 | O | THR | 220 | −9.702 | 43.334 | 37.250 | 1.00 | 21.54 |
| ATOM | 1608 | N | VAL | 221 | −7.890 | 44.043 | 38.382 | 1.00 | 23.13 |
| ATOM | 1609 | CA | VAL | 221 | −7.594 | 45.177 | 37.510 | 1.00 | 25.08 |
| ATOM | 1610 | CB | VAL | 221 | −8.156 | 46.505 | 38.068 | 1.00 | 26.82 |
| ATOM | 1611 | CG1 | VAL | 221 | −9.668 | 46.483 | 38.028 | 1.00 | 37.71 |
| ATOM | 1612 | CG2 | VAL | 221 | −7.669 | 46.727 | 39.493 | 1.00 | 29.80 |
| ATOM | 1613 | C | VAL | 221 | −6.084 | 45.286 | 37.440 | 1.00 | 23.63 |
| ATOM | 1614 | O | VAL | 221 | −5.395 | 44.882 | 38.364 | 1.00 | 27.43 |
| ATOM | 1615 | N | VAL | 222 | −5.566 | 45.823 | 36.347 | 1.00 | 28.47 |
| ATOM | 1616 | CA | VAL | 222 | −4.123 | 45.958 | 36.190 | 1.00 | 31.60 |
| ATOM | 1617 | CB | VAL | 222 | −3.694 | 45.560 | 34.759 | 1.00 | 30.42 |
| ATOM | 1618 | CG1 | VAL | 222 | −2.186 | 45.711 | 34.594 | 1.00 | 28.45 |
| ATOM | 1619 | CG2 | VAL | 222 | −4.149 | 44.139 | 34.465 | 1.00 | 29.67 |
| ATOM | 1620 | C | VAL | 222 | −3.672 | 47.394 | 36.451 | 1.00 | 37.48 |
| ATOM | 1621 | O | VAL | 222 | −4.236 | 48.335 | 35.892 | 1.00 | 37.96 |
| ATOM | 1622 | N | THR | 223 | −2.658 | 47.567 | 37.293 | 1.00 | 39.88 |
| ATOM | 1623 | CA | THR | 223 | −2.160 | 48.910 | 37.583 | 1.00 | 44.12 |
| ATOM | 1624 | CB | THR | 223 | −2.354 | 49.289 | 39.078 | 1.00 | 45.23 |
| ATOM | 1625 | OG1 | THR | 223 | −1.514 | 48.471 | 39.902 | 1.00 | 45.16 |
| ATOM | 1626 | CG2 | THR | 223 | −3.806 | 49.099 | 39.489 | 1.00 | 48.57 |
| ATOM | 1627 | C | THR | 223 | −0.684 | 49.074 | 37.232 | 1.00 | 43.23 |
| ATOM | 1628 | O | THR | 223 | 0.066 | 48.099 | 37.150 | 1.00 | 41.21 |
| ATOM | 1629 | N | GLY | 224 | −0.280 | 50.322 | 37.013 | 1.00 | 47.94 |
| ATOM | 1630 | CA | GLY | 224 | 1.104 | 50.621 | 36.687 | 1.00 | 46.70 |
| ATOM | 1631 | C | GLY | 224 | 1.502 | 50.432 | 35.235 | 1.00 | 46.61 |
| ATOM | 1632 | O | GLY | 224 | 2.690 | 50.484 | 34.916 | 1.00 | 43.46 |
| ATOM | 1633 | N | ALA | 225 | 0.525 | 50.218 | 34.357 | 1.00 | 47.84 |
| ATOM | 1634 | CA | ALA | 225 | 0.813 | 50.012 | 32.939 | 1.00 | 56.26 |
| ATOM | 1635 | CB | ALA | 225 | −0.470 | 49.640 | 32.190 | 1.00 | 50.84 |
| ATOM | 1636 | C | ALA | 225 | 1.453 | 51.258 | 32.320 | 1.00 | 60.77 |
| ATOM | 1637 | O | ALA | 225 | 2.501 | 51.174 | 31.672 | 1.00 | 58.89 |
| ATOM | 1638 | N | LYS | 226 | 0.817 | 52.408 | 32.531 | 1.00 | 66.97 |
| ATOM | 1639 | CA | LYS | 226 | 1.308 | 53.685 | 32.018 | 1.00 | 70.10 |
| ATOM | 1640 | CB | LYS | 226 | 0.364 | 54.816 | 32.435 | 1.00 | 77.98 |
| ATOM | 1641 | CG | LYS | 226 | 0.704 | 56.180 | 31.849 | 1.00 | 83.40 |
| ATOM | 1642 | CD | LYS | 226 | 0.416 | 56.218 | 30.358 | 1.00 | 87.60 |
| ATOM | 1643 | CE | LYS | 226 | 0.570 | 57.619 | 29.796 | 1.00 | 89.70 |
| ATOM | 1644 | NZ | LYS | 226 | 0.219 | 57.665 | 28.350 | 1.00 | 94.81 |
| ATOM | 1645 | C | LYS | 226 | 2.697 | 53.961 | 32.583 | 1.00 | 69.36 |
| ATOM | 1646 | O | LYS | 226 | 3.590 | 54.420 | 31.872 | 1.00 | 66.65 |
| ATOM | 1647 | N | LEU | 227 | 2.863 | 53.684 | 33.872 | 1.00 | 68.65 |
| ATOM | 1648 | CA | LEU | 227 | 4.135 | 53.891 | 34.549 | 1.00 | 68.69 |
| ATOM | 1649 | CB | LEU | 227 | 3.951 | 53.769 | 36.063 | 1.00 | 71.53 |
| ATOM | 1650 | CG | LEU | 227 | 2.865 | 54.614 | 36.729 | 1.00 | 73.93 |
| ATOM | 1651 | CD1 | LEU | 227 | 2.852 | 54.317 | 38.221 | 1.00 | 76.11 |
| ATOM | 1652 | CD2 | LEU | 227 | 3.117 | 56.090 | 36.478 | 1.00 | 74.22 |
| ATOM | 1653 | C | LEU | 227 | 5.151 | 52.851 | 34.073 | 1.00 | 69.38 |
| ATOM | 1654 | O | LEU | 227 | 6.320 | 52.873 | 34.473 | 1.00 | 67.42 |

TABLE 2-continued

Atomic coordinates on the three-dimensional crystal structure of the FabK-FMN complex having the amino acid sequences 2-312 of SEQ ID NO: 1

| A | B | C | D | E | F | G | H | I | J |
|---|---|---|---|---|---|---|---|---|---|
| ATOM | 1655 | N | GLY | 228 | 4.694 | 51.932 | 33.227 | 1.00 | 67.35 |
| ATOM | 1656 | CA | GLY | 228 | 5.580 | 50.908 | 32.713 | 1.00 | 62.24 |
| ATOM | 1657 | C | GLY | 228 | 5.453 | 49.559 | 33.392 | 1.00 | 59.27 |
| ATOM | 1658 | O | GLY | 228 | 5.354 | 48.541 | 32.715 | 1.00 | 61.04 |
| ATOM | 1659 | N | HIS | 229 | 5.456 | 49.549 | 34.721 | 1.00 | 53.37 |
| ATOM | 1660 | CA | HIS | 229 | 5.356 | 48.306 | 35.490 | 1.00 | 54.86 |
| ATOM | 1661 | CB | HIS | 229 | 6.095 | 48.466 | 36.826 | 1.00 | 63.64 |
| ATOM | 1662 | CG | HIS | 229 | 5.890 | 49.800 | 37.477 | 1.00 | 75.72 |
| ATOM | 1663 | CD2 | HIS | 229 | 5.097 | 50.178 | 38.508 | 1.00 | 77.71 |
| ATOM | 1664 | ND1 | HIS | 229 | 6.544 | 50.941 | 37.061 | 1.00 | 79.40 |
| ATOM | 1665 | CE1 | HIS | 229 | 6.164 | 51.962 | 37.808 | 1.00 | 77.92 |
| ATOM | 1666 | NE2 | HIS | 229 | 5.286 | 51.526 | 38.694 | 1.00 | 76.33 |
| ATOM | 1667 | C | HIS | 229 | 3.919 | 47.831 | 35.756 | 1.00 | 50.66 |
| ATOM | 1668 | O | HIS | 229 | 3.340 | 48.134 | 36.800 | 1.00 | 51.83 |
| ATOM | 1669 | N | PRO | 230 | 3.339 | 47.049 | 34.828 | 1.00 | 43.63 |
| ATOM | 1670 | CD | PRO | 230 | 3.971 | 46.460 | 33.639 | 1.00 | 42.31 |
| ATOM | 1671 | CA | PRO | 230 | 1.970 | 46.537 | 34.969 | 1.00 | 39.12 |
| ATOM | 1672 | CB | PRO | 230 | 1.681 | 45.914 | 33.599 | 1.00 | 38.62 |
| ATOM | 1673 | CG | PRO | 230 | 2.813 | 46.373 | 32.714 | 1.00 | 38.41 |
| ATOM | 1674 | C | PRO | 230 | 1.860 | 45.489 | 36.076 | 1.00 | 38.55 |
| ATOM | 1675 | O | PRO | 230 | 2.671 | 44.568 | 36.155 | 1.00 | 35.39 |
| ATOM | 1676 | N | ALA | 231 | 0.847 | 45.625 | 36.921 | 1.00 | 37.12 |
| ATOM | 1677 | CA | ALA | 231 | 0.630 | 44.678 | 38.005 | 1.00 | 33.39 |
| ATOM | 1678 | CB | ALA | 231 | 1.147 | 45.254 | 39.314 | 1.00 | 22.87 |
| ATOM | 1679 | C | ALA | 231 | −0.858 | 44.398 | 38.113 | 1.00 | 33.68 |
| ATOM | 1680 | O | ALA | 231 | −1.670 | 45.307 | 37.925 | 1.00 | 37.73 |
| ATOM | 1681 | N | ARG | 232 | −1.217 | 43.147 | 38.399 | 1.00 | 29.06 |
| ATOM | 1682 | CA | ARG | 232 | −2.623 | 42.772 | 38.551 | 1.00 | 30.02 |
| ATOM | 1683 | CB | ARG | 232 | −2.901 | 41.397 | 37.943 | 1.00 | 21.43 |
| ATOM | 1684 | CG | ARG | 232 | −4.384 | 41.043 | 37.903 | 1.00 | 20.98 |
| ATOM | 1685 | CD | ARG | 232 | −4.635 | 39.691 | 37.235 | 1.00 | 21.15 |
| ATOM | 1686 | NE | ARG | 232 | −4.274 | 39.690 | 35.819 | 1.00 | 25.33 |
| ATOM | 1687 | CZ | ARG | 232 | −4.896 | 40.404 | 34.879 | 1.00 | 27.64 |
| ATOM | 1688 | NH1 | ARG | 232 | −5.929 | 41.187 | 35.184 | 1.00 | 22.07 |
| ATOM | 1689 | NH2 | ARG | 232 | −4.470 | 40.350 | 33.625 | 1.00 | 23.50 |
| ATOM | 1690 | C | ARG | 232 | −2.987 | 42.739 | 40.031 | 1.00 | 30.74 |
| ATOM | 1691 | O | ARG | 232 | −2.350 | 42.036 | 40.818 | 1.00 | 27.83 |
| ATOM | 1692 | N | VAL | 233 | −4.015 | 43.497 | 40.403 | 1.00 | 29.85 |
| ATOM | 1693 | CA | VAL | 233 | −4.458 | 43.558 | 41.797 | 1.00 | 31.42 |
| ATOM | 1694 | CB | VAL | 233 | −4.043 | 44.889 | 42.465 | 1.00 | 26.72 |
| ATOM | 1695 | CG1 | VAL | 233 | −2.534 | 45.063 | 42.400 | 1.00 | 24.65 |
| ATOM | 1696 | CG2 | VAL | 233 | −4.747 | 46.040 | 41.783 | 1.00 | 23.19 |
| ATOM | 1697 | C | VAL | 233 | −5.973 | 43.447 | 41.916 | 1.00 | 30.16 |
| ATOM | 1698 | O | VAL | 233 | −6.703 | 43.473 | 40.918 | 1.00 | 25.49 |
| ATOM | 1699 | N | LEU | 234 | −6.436 | 43.346 | 43.156 | 1.00 | 26.19 |
| ATOM | 1700 | CA | LEU | 234 | −7.857 | 43.240 | 43.433 | 1.00 | 27.86 |
| ATOM | 1701 | CB | LEU | 234 | −8.069 | 42.997 | 44.919 | 1.00 | 35.12 |
| ATOM | 1702 | CG | LEU | 234 | −9.326 | 42.208 | 45.255 | 1.00 | 44.86 |
| ATOM | 1703 | CD1 | LEU | 234 | −9.255 | 40.849 | 44.573 | 1.00 | 44.16 |
| ATOM | 1704 | CD2 | LEU | 234 | −9.444 | 42.045 | 46.762 | 1.00 | 44.31 |
| ATOM | 1705 | C | LEU | 234 | −8.518 | 44.545 | 43.003 | 1.00 | 28.68 |
| ATOM | 1706 | O | LEU | 234 | −7.921 | 45.619 | 43.119 | 1.00 | 28.50 |
| ATOM | 1707 | N | ARG | 235 | −9.737 | 44.449 | 42.489 | 1.00 | 32.07 |
| ATOM | 1708 | CA | ARG | 235 | −10.474 | 45.618 | 42.018 | 1.00 | 38.23 |
| ATOM | 1709 | CB | ARG | 235 | −11.655 | 45.164 | 41.158 | 1.00 | 43.34 |
| ATOM | 1710 | CG | ARG | 235 | −12.235 | 46.241 | 40.266 | 1.00 | 44.53 |
| ATOM | 1711 | CD | ARG | 235 | −13.027 | 45.598 | 39.150 | 1.00 | 53.98 |
| ATOM | 1712 | NE | ARG | 235 | −12.758 | 46.234 | 37.863 | 1.00 | 62.97 |
| ATOM | 1713 | CZ | ARG | 235 | −12.690 | 45.573 | 36.711 | 1.00 | 62.41 |
| ATOM | 1714 | NH1 | ARG | 235 | −12.871 | 44.261 | 36.695 | 1.00 | 67.00 |
| ATOM | 1715 | NH2 | ARG | 235 | −12.435 | 46.218 | 35.578 | 1.00 | 61.04 |
| ATOM | 1716 | C | ARG | 235 | −10.962 | 46.420 | 43.218 | 1.00 | 42.25 |
| ATOM | 1717 | O | ARG | 235 | −12.016 | 46.137 | 43.790 | 1.00 | 43.00 |
| ATOM | 1718 | N | THR | 236 | −10.199 | 47.433 | 43.599 | 1.00 | 46.04 |
| ATOM | 1719 | CA | THR | 236 | −10.565 | 48.213 | 44.764 | 1.00 | 51.08 |
| ATOM | 1720 | CB | THR | 236 | −9.560 | 47.943 | 45.921 | 1.00 | 53.63 |
| ATOM | 1721 | OG1 | THR | 236 | −10.249 | 47.994 | 47.174 | 1.00 | 63.64 |
| ATOM | 1722 | CG2 | THR | 236 | −8.431 | 48.971 | 45.925 | 1.00 | 45.30 |
| ATOM | 1723 | C | THR | 236 | −10.605 | 49.696 | 44.446 | 1.00 | 52.07 |
| ATOM | 1724 | O | THR | 236 | −9.886 | 50.172 | 43.566 | 1.00 | 50.41 |
| ATOM | 1725 | N | PRO | 237 | −11.451 | 50.451 | 45.163 | 1.00 | 58.58 |
| ATOM | 1726 | CD | PRO | 237 | −12.302 | 50.028 | 46.291 | 1.00 | 57.34 |
| ATOM | 1727 | CA | PRO | 237 | −11.560 | 51.895 | 44.930 | 1.00 | 56.97 |
| ATOM | 1728 | CB | PRO | 237 | −12.310 | 52.379 | 46.165 | 1.00 | 57.64 |

TABLE 2-continued

Atomic coordinates on the three-dimensional crystal structure of the FabK-FMN complex having the amino acid sequences 2-312 of SEQ ID NO: 1

| A | B | C | D | E | F | G | H | I | J |
|---|---|---|---|---|---|---|---|---|---|
| ATOM | 1729 | CG | PRO | 237 | −13.221 | 51.217 | 46.464 | 1.00 | 59.39 |
| ATOM | 1730 | C | PRO | 237 | −10.169 | 52.524 | 44.791 | 1.00 | 54.14 |
| ATOM | 1731 | O | PRO | 237 | −9.900 | 53.271 | 43.848 | 1.00 | 51.93 |
| ATOM | 1732 | N | PHE | 238 | −9.292 | 52.202 | 45.739 | 1.00 | 50.88 |
| ATOM | 1733 | CA | PHE | 238 | −7.921 | 52.703 | 45.740 | 1.00 | 47.00 |
| ATOM | 1734 | CB | PHE | 238 | −7.161 | 52.088 | 46.909 | 1.00 | 42.58 |
| ATOM | 1735 | CG | PHE | 238 | −5.694 | 52.365 | 46.900 | 1.00 | 42.37 |
| ATOM | 1736 | CD1 | PHE | 238 | −5.216 | 53.672 | 46.955 | 1.00 | 44.08 |
| ATOM | 1737 | CD2 | PHE | 238 | −4.780 | 51.314 | 46.907 | 1.00 | 43.50 |
| ATOM | 1738 | CE1 | PHE | 238 | −3.839 | 53.934 | 47.026 | 1.00 | 42.78 |
| ATOM | 1739 | CE2 | PHE | 238 | −3.403 | 51.560 | 46.977 | 1.00 | 47.96 |
| ATOM | 1740 | CZ | PHE | 238 | −2.934 | 52.874 | 47.039 | 1.00 | 47.27 |
| ATOM | 1741 | C | PHE | 238 | −7.262 | 52.308 | 44.428 | 1.00 | 47.40 |
| ATOM | 1742 | O | PHE | 238 | −6.565 | 53.106 | 43.795 | 1.00 | 42.68 |
| ATOM | 1743 | N | ALA | 239 | −7.498 | 51.063 | 44.029 | 1.00 | 45.18 |
| ATOM | 1744 | CA | ALA | 239 | −6.956 | 50.534 | 42.787 | 1.00 | 46.25 |
| ATOM | 1745 | CB | ALA | 239 | −7.427 | 49.093 | 42.588 | 1.00 | 42.79 |
| ATOM | 1746 | C | ALA | 239 | −7.395 | 51.405 | 41.612 | 1.00 | 43.65 |
| ATOM | 1747 | O | ALA | 239 | −6.582 | 51.797 | 40.781 | 1.00 | 35.95 |
| ATOM | 1748 | N | ARG | 240 | −8.687 | 51.701 | 41.541 | 1.00 | 50.05 |
| ATOM | 1749 | CA | ARG | 240 | −9.188 | 52.546 | 40.467 | 1.00 | 54.80 |
| ATOM | 1750 | CB | ARG | 240 | −10.710 | 52.697 | 40.556 | 1.00 | 55.30 |
| ATOM | 1751 | CG | ARG | 240 | −11.488 | 51.628 | 39.793 | 1.00 | 58.00 |
| ATOM | 1752 | CD | ARG | 240 | −12.980 | 51.909 | 39.820 | 1.00 | 52.98 |
| ATOM | 1753 | NE | ARG | 240 | −13.557 | 51.683 | 41.143 | 1.00 | 55.00 |
| ATOM | 1754 | CZ | ARG | 240 | −13.807 | 50.482 | 41.658 | 1.00 | 55.09 |
| ATOM | 1755 | NH1 | ARG | 240 | −13.534 | 49.383 | 40.961 | 1.00 | 50.02 |
| ATOM | 1756 | NH2 | ARG | 240 | −14.335 | 50.382 | 42.872 | 1.00 | 48.88 |
| ATOM | 1757 | C | ARG | 240 | −8.527 | 53.916 | 40.563 | 1.00 | 57.38 |
| ATOM | 1758 | O | ARG | 240 | −8.100 | 54.490 | 39.556 | 1.00 | 54.93 |
| ATOM | 1759 | N | LYS | 241 | −8.436 | 54.431 | 41.785 | 1.00 | 60.08 |
| ATOM | 1760 | CA | LYS | 241 | −7.827 | 55.732 | 42.014 | 1.00 | 63.45 |
| ATOM | 1761 | CB | LYS | 241 | −7.721 | 56.008 | 43.515 | 1.00 | 70.52 |
| ATOM | 1762 | CG | LYS | 241 | −7.003 | 57.302 | 43.863 | 1.00 | 79.22 |
| ATOM | 1763 | CD | LYS | 241 | −7.333 | 57.781 | 45.279 | 1.00 | 87.15 |
| ATOM | 1764 | CE | LYS | 241 | −7.072 | 56.719 | 46.351 | 1.00 | 89.86 |
| ATOM | 1765 | NZ | LYS | 241 | −8.114 | 55.649 | 46.394 | 1.00 | 88.17 |
| ATOM | 1766 | C | LYS | 241 | −6.452 | 55.771 | 41.369 | 1.00 | 62.38 |
| ATOM | 1767 | O | LYS | 241 | −6.174 | 56.634 | 40.530 | 1.00 | 59.72 |
| ATOM | 1768 | N | ILE | 242 | −5.596 | 54.829 | 41.752 | 1.00 | 59.88 |
| ATOM | 1769 | CA | ILE | 242 | −4.259 | 54.772 | 41.181 | 1.00 | 58.65 |
| ATOM | 1770 | CB | ILE | 242 | −3.479 | 53.556 | 41.698 | 1.00 | 58.24 |
| ATOM | 1771 | CG2 | ILE | 242 | −2.144 | 53.441 | 40.968 | 1.00 | 57.02 |
| ATOM | 1772 | CG1 | ILE | 242 | −3.244 | 53.705 | 43.200 | 1.00 | 54.76 |
| ATOM | 1773 | CD1 | ILE | 242 | −2.495 | 52.546 | 43.810 | 1.00 | 58.23 |
| ATOM | 1774 | C | ILE | 242 | −4.320 | 54.732 | 39.653 | 1.00 | 56.02 |
| ATOM | 1775 | O | ILE | 242 | −3.654 | 55.522 | 38.994 | 1.00 | 57.35 |
| ATOM | 1776 | N | GLN | 243 | −5.115 | 53.823 | 39.092 | 1.00 | 53.27 |
| ATOM | 1777 | CA | GLN | 243 | −5.253 | 53.730 | 37.634 | 1.00 | 55.20 |
| ATOM | 1778 | CB | GLN | 243 | −6.485 | 52.904 | 37.254 | 1.00 | 53.24 |
| ATOM | 1779 | CG | GLN | 243 | −6.238 | 51.416 | 37.176 | 1.00 | 50.96 |
| ATOM | 1780 | CD | GLN | 243 | −7.455 | 50.651 | 36.710 | 1.00 | 51.96 |
| ATOM | 1781 | OE1 | GLN | 243 | −7.380 | 49.453 | 36.450 | 1.00 | 55.67 |
| ATOM | 1782 | NE2 | GLN | 243 | −8.588 | 51.337 | 36.607 | 1.00 | 51.06 |
| ATOM | 1783 | C | GLN | 243 | −5.381 | 55.115 | 36.997 | 1.00 | 59.37 |
| ATOM | 1784 | O | GLN | 243 | −4.831 | 55.377 | 35.913 | 1.00 | 50.85 |
| ATOM | 1785 | N | GLU | 244 | −6.112 | 55.993 | 37.681 | 1.00 | 63.91 |
| ATOM | 1786 | CA | GLU | 244 | −6.330 | 57.355 | 37.210 | 1.00 | 67.92 |
| ATOM | 1787 | CB | GLU | 244 | −7.515 | 57.988 | 37.943 | 1.00 | 78.40 |
| ATOM | 1788 | CG | GLU | 244 | −8.846 | 57.312 | 37.673 | 1.00 | 98.50 |
| ATOM | 1789 | CD | GLU | 244 | −9.150 | 57.192 | 36.189 | 1.00 | 108.82 |
| ATOM | 1790 | OE1 | GLU | 244 | −8.499 | 56.372 | 35.506 | 1.00 | 115.40 |
| ATOM | 1791 | OE2 | GLU | 244 | −10.038 | 57.924 | 35.703 | 1.00 | 116.99 |
| ATOM | 1792 | C | GLU | 244 | −5.097 | 58.213 | 37.419 | 1.00 | 63.74 |
| ATOM | 1793 | O | GLU | 244 | −4.572 | 58.801 | 36.474 | 1.00 | 58.37 |
| ATOM | 1794 | N | MET | 245 | −4.637 | 58.275 | 38.664 | 1.00 | 63.13 |
| ATOM | 1795 | CA | MET | 245 | −3.470 | 59.074 | 39.009 | 1.00 | 67.33 |
| ATOM | 1796 | CB | MET | 245 | −3.048 | 58.784 | 40.458 | 1.00 | 67.06 |
| ATOM | 1797 | CG | MET | 245 | −2.417 | 59.973 | 41.190 | 1.00 | 73.11 |
| ATOM | 1798 | SD | MET | 245 | −3.605 | 61.303 | 41.594 | 1.00 | 71.13 |
| ATOM | 1799 | CE | MET | 245 | −3.575 | 62.260 | 40.086 | 1.00 | 71.20 |
| ATOM | 1800 | C | MET | 245 | −2.299 | 58.798 | 38.059 | 1.00 | 70.47 |
| ATOM | 1801 | O | MET | 245 | −1.417 | 59.641 | 37.885 | 1.00 | 71.05 |
| ATOM | 1802 | N | GLU | 246 | −2.310 | 57.627 | 37.430 | 1.00 | 72.99 |

TABLE 2-continued

Atomic coordinates on the three-dimensional crystal structure of the FabK-
FMN complex having the amino acid sequences 2-312 of SEQ ID NO: 1

| A | B | C | D | E | F | G | H | I | J |
|---|---|---|---|---|---|---|---|---|---|
| ATOM | 1803 | CA | GLU | 246 | −1.242 | 57.232 | 36.521 | 1.00 | 76.46 |
| ATOM | 1804 | CB | GLU | 246 | −1.481 | 55.815 | 36.003 | 1.00 | 80.33 |
| ATOM | 1805 | CG | GLU | 246 | −1.635 | 54.800 | 37.111 | 1.00 | 85.07 |
| ATOM | 1806 | CD | GLU | 246 | −1.344 | 53.388 | 36.663 | 1.00 | 86.07 |
| ATOM | 1807 | OE1 | GLU | 246 | −2.025 | 52.886 | 35.744 | 1.00 | 85.99 |
| ATOM | 1808 | OE2 | GLU | 246 | −0.425 | 52.779 | 37.241 | 1.00 | 87.48 |
| ATOM | 1809 | C | GLU | 246 | −1.016 | 58.159 | 35.344 | 1.00 | 80.72 |
| ATOM | 1810 | O | GLU | 246 | 0.127 | 58.424 | 34.987 | 1.00 | 83.59 |
| ATOM | 1811 | N | PHE | 247 | −2.079 | 58.655 | 34.724 | 1.00 | 87.14 |
| ATOM | 1812 | CA | PHE | 247 | −1.887 | 59.548 | 33.585 | 1.00 | 93.62 |
| ATOM | 1813 | CB | PHE | 247 | −2.763 | 59.111 | 32.403 | 1.00 | 102.74 |
| ATOM | 1814 | CG | PHE | 247 | −4.122 | 58.612 | 32.798 | 1.00 | 113.83 |
| ATOM | 1815 | CD1 | PHE | 247 | −5.000 | 59.422 | 33.510 | 1.00 | 119.30 |
| ATOM | 1816 | CD2 | PHE | 247 | −4.533 | 57.334 | 32.433 | 1.00 | 116.96 |
| ATOM | 1817 | CE1 | PHE | 247 | −6.274 | 58.965 | 33.853 | 1.00 | 123.42 |
| ATOM | 1818 | CE2 | PHE | 247 | −5.802 | 56.866 | 32.769 | 1.00 | 120.59 |
| ATOM | 1819 | CZ | PHE | 247 | −6.675 | 57.684 | 33.480 | 1.00 | 123.97 |
| ATOM | 1820 | C | PHE | 247 | −2.100 | 61.031 | 33.880 | 1.00 | 91.70 |
| ATOM | 1821 | O | PHE | 247 | −1.638 | 61.888 | 33.128 | 1.00 | 89.12 |
| ATOM | 1822 | N | GLU | 248 | −2.784 | 61.329 | 34.980 | 1.00 | 90.65 |
| ATOM | 1823 | CA | GLU | 248 | −3.044 | 62.710 | 35.369 | 1.00 | 90.70 |
| ATOM | 1824 | CB | GLU | 248 | −4.270 | 62.772 | 36.272 | 1.00 | 99.73 |
| ATOM | 1825 | CG | GLU | 248 | −5.444 | 61.977 | 35.756 | 1.00 | 117.28 |
| ATOM | 1826 | CD | GLU | 248 | −6.591 | 61.946 | 36.741 | 1.00 | 128.41 |
| ATOM | 1827 | OE1 | GLU | 248 | −6.353 | 61.592 | 37.918 | 1.00 | 133.65 |
| ATOM | 1828 | OE2 | GLU | 248 | −7.729 | 62.271 | 36.337 | 1.00 | 135.77 |
| ATOM | 1829 | C | GLU | 248 | −1.839 | 63.289 | 36.112 | 1.00 | 85.19 |
| ATOM | 1830 | O | GLU | 248 | −1.444 | 64.434 | 35.880 | 1.00 | 84.92 |
| ATOM | 1831 | N | ASN | 249 | −1.269 | 62.486 | 37.009 | 1.00 | 74.73 |
| ATOM | 1832 | CA | ASN | 249 | −0.111 | 62.882 | 37.805 | 1.00 | 64.94 |
| ATOM | 1833 | CB | ASN | 249 | −0.575 | 63.653 | 39.045 | 1.00 | 61.49 |
| ATOM | 1834 | CG | ASN | 249 | 0.579 | 64.121 | 39.903 | 1.00 | 63.43 |
| ATOM | 1835 | OD1 | ASN | 249 | 1.724 | 64.169 | 39.453 | 1.00 | 67.35 |
| ATOM | 1836 | ND2 | ASN | 249 | 0.283 | 64.484 | 41.142 | 1.00 | 61.72 |
| ATOM | 1837 | C | ASN | 249 | 0.680 | 61.632 | 38.212 | 1.00 | 60.29 |
| ATOM | 1838 | O | ASN | 249 | 0.719 | 61.256 | 39.387 | 1.00 | 53.69 |
| ATOM | 1839 | N | PRO | 250 | 1.324 | 60.977 | 37.231 | 1.00 | 62.07 |
| ATOM | 1840 | CD | PRO | 250 | 1.481 | 61.515 | 35.869 | 1.00 | 60.50 |
| ATOM | 1841 | CA | PRO | 250 | 2.131 | 59.760 | 37.392 | 1.00 | 62.48 |
| ATOM | 1842 | CB | PRO | 250 | 2.812 | 59.613 | 36.031 | 1.00 | 59.89 |
| ATOM | 1843 | CG | PRO | 250 | 2.853 | 61.025 | 35.510 | 1.00 | 61.31 |
| ATOM | 1844 | C | PRO | 250 | 3.137 | 59.764 | 38.536 | 1.00 | 63.84 |
| ATOM | 1845 | O | PRO | 250 | 3.189 | 58.821 | 39.325 | 1.00 | 66.05 |
| ATOM | 1846 | N | MET | 251 | 3.941 | 60.817 | 38.613 | 1.00 | 66.22 |
| ATOM | 1847 | CA | MET | 251 | 4.947 | 60.930 | 39.660 | 1.00 | 67.04 |
| ATOM | 1848 | CB | MET | 251 | 5.603 | 62.313 | 39.599 | 1.00 | 71.10 |
| ATOM | 1849 | CG | MET | 251 | 6.894 | 62.443 | 40.387 | 1.00 | 75.90 |
| ATOM | 1850 | SD | MET | 251 | 7.786 | 63.949 | 39.937 | 1.00 | 83.70 |
| ATOM | 1851 | CE | MET | 251 | 8.773 | 63.353 | 38.550 | 1.00 | 75.21 |
| ATOM | 1852 | C | MET | 251 | 4.300 | 60.703 | 41.024 | 1.00 | 66.98 |
| ATOM | 1853 | O | MET | 251 | 4.837 | 59.979 | 41.864 | 1.00 | 69.20 |
| ATOM | 1854 | N | GLN | 252 | 3.139 | 61.310 | 41.239 | 1.00 | 67.70 |
| ATOM | 1855 | CA | GLN | 252 | 2.436 | 61.156 | 42.506 | 1.00 | 72.22 |
| ATOM | 1856 | CB | GLN | 252 | 1.252 | 62.121 | 42.582 | 1.00 | 77.75 |
| ATOM | 1857 | CG | GLN | 252 | 0.465 | 62.032 | 43.880 | 1.00 | 84.71 |
| ATOM | 1858 | CD | GLN | 252 | −0.562 | 63.143 | 44.013 | 1.00 | 90.90 |
| ATOM | 1859 | OE1 | GLN | 252 | −0.214 | 64.325 | 44.024 | 1.00 | 93.24 |
| ATOM | 1860 | NE2 | GLN | 252 | −1.833 | 62.769 | 44.114 | 1.00 | 93.10 |
| ATOM | 1861 | C | GLN | 252 | 1.946 | 59.726 | 42.682 | 1.00 | 71.05 |
| ATOM | 1862 | O | GLN | 252 | 2.033 | 59.164 | 43.773 | 1.00 | 74.03 |
| ATOM | 1863 | N | ALA | 253 | 1.430 | 59.138 | 41.607 | 1.00 | 68.27 |
| ATOM | 1864 | CA | ALA | 253 | 0.935 | 57.767 | 41.658 | 1.00 | 65.95 |
| ATOM | 1865 | CB | ALA | 253 | 0.436 | 57.334 | 40.286 | 1.00 | 61.46 |
| ATOM | 1866 | C | ALA | 253 | 2.032 | 56.823 | 42.145 | 1.00 | 67.60 |
| ATOM | 1867 | O | ALA | 253 | 1.780 | 55.957 | 42.987 | 1.00 | 69.41 |
| ATOM | 1868 | N | GLU | 254 | 3.246 | 56.991 | 41.623 | 1.00 | 67.71 |
| ATOM | 1869 | CA | GLU | 254 | 4.372 | 56.148 | 42.027 | 1.00 | 69.80 |
| ATOM | 1870 | CB | GLU | 254 | 5.642 | 56.551 | 41.274 | 1.00 | 77.42 |
| ATOM | 1871 | CG | GLU | 254 | 5.640 | 56.141 | 39.808 | 1.00 | 89.83 |
| ATOM | 1872 | CD | GLU | 254 | 6.875 | 56.611 | 39.059 | 1.00 | 97.08 |
| ATOM | 1873 | OE1 | GLU | 254 | 7.069 | 56.174 | 37.904 | 1.00 | 102.30 |
| ATOM | 1874 | OE2 | GLU | 254 | 7.647 | 57.420 | 39.618 | 1.00 | 101.17 |
| ATOM | 1875 | C | GLU | 254 | 4.594 | 56.275 | 43.529 | 1.00 | 67.91 |
| ATOM | 1876 | O | GLU | 254 | 4.909 | 55.293 | 44.206 | 1.00 | 57.38 |

TABLE 2-continued

Atomic coordinates on the three-dimensional crystal structure of the FabK-FMN complex having the amino acid sequences 2-312 of SEQ ID NO: 1

| A | B | C | D | E | F | G | H | I | J |
|---|---|---|---|---|---|---|---|---|---|
| ATOM | 1877 | N | GLU | 255 | 4.422 | 57.495 | 44.035 | 1.00 | 69.14 |
| ATOM | 1878 | CA | GLU | 255 | 4.572 | 57.786 | 45.457 | 1.00 | 70.03 |
| ATOM | 1879 | CB | GLU | 255 | 4.411 | 59.290 | 45.699 | 1.00 | 82.45 |
| ATOM | 1880 | CG | GLU | 255 | 4.270 | 59.674 | 47.165 | 1.00 | 101.54 |
| ATOM | 1881 | CD | GLU | 255 | 5.553 | 59.473 | 47.951 | 1.00 | 109.82 |
| ATOM | 1882 | OE1 | GLU | 255 | 6.480 | 60.296 | 47.794 | 1.00 | 116.96 |
| ATOM | 1883 | OE2 | GLU | 255 | 5.637 | 58.489 | 48.720 | 1.00 | 113.29 |
| ATOM | 1884 | C | GLU | 255 | 3.502 | 57.025 | 46.240 | 1.00 | 65.97 |
| ATOM | 1885 | O | GLU | 255 | 3.763 | 56.471 | 47.309 | 1.00 | 60.56 |
| ATOM | 1886 | N | MET | 256 | 2.296 | 57.002 | 45.684 | 1.00 | 63.80 |
| ATOM | 1887 | CA | MET | 256 | 1.160 | 56.331 | 46.301 | 1.00 | 61.68 |
| ATOM | 1888 | CB | MET | 256 | −0.125 | 56.716 | 45.558 | 1.00 | 69.94 |
| ATOM | 1889 | CG | MET | 256 | −0.544 | 58.176 | 45.755 | 1.00 | 76.26 |
| ATOM | 1890 | SD | MET | 256 | −1.714 | 58.782 | 44.510 | 1.00 | 81.28 |
| ATOM | 1891 | CE | MET | 256 | −3.161 | 57.759 | 44.866 | 1.00 | 80.74 |
| ATOM | 1892 | C | MET | 256 | 1.309 | 54.813 | 46.342 | 1.00 | 58.24 |
| ATOM | 1893 | O | MET | 256 | 0.762 | 54.149 | 47.225 | 1.00 | 54.40 |
| ATOM | 1894 | N | LEU | 257 | 2.055 | 54.265 | 45.391 | 1.00 | 56.92 |
| ATOM | 1895 | CA | LEU | 257 | 2.261 | 52.823 | 45.324 | 1.00 | 54.32 |
| ATOM | 1896 | CB | LEU | 257 | 2.740 | 52.444 | 43.926 | 1.00 | 51.83 |
| ATOM | 1897 | CG | LEU | 257 | 1.726 | 52.782 | 42.835 | 1.00 | 50.62 |
| ATOM | 1898 | CD1 | LEU | 257 | 2.414 | 52.801 | 41.485 | 1.00 | 58.52 |
| ATOM | 1899 | CD2 | LEU | 257 | 0.584 | 51.776 | 42.862 | 1.00 | 48.92 |
| ATOM | 1900 | C | LEU | 257 | 3.260 | 52.329 | 46.366 | 1.00 | 53.70 |
| ATOM | 1901 | O | LEU | 257 | 3.133 | 51.221 | 46.889 | 1.00 | 51.36 |
| ATOM | 1902 | N | VAL | 258 | 4.245 | 53.167 | 46.666 | 1.00 | 52.61 |
| ATOM | 1903 | CA | VAL | 258 | 5.285 | 52.838 | 47.633 | 1.00 | 51.98 |
| ATOM | 1904 | CB | VAL | 258 | 6.090 | 54.109 | 48.003 | 1.00 | 52.85 |
| ATOM | 1905 | CG1 | VAL | 258 | 7.323 | 53.739 | 48.809 | 1.00 | 48.30 |
| ATOM | 1906 | CG2 | VAL | 258 | 6.483 | 54.854 | 46.739 | 1.00 | 48.87 |
| ATOM | 1907 | C | VAL | 258 | 4.750 | 52.187 | 48.919 | 1.00 | 52.13 |
| ATOM | 1908 | O | VAL | 258 | 3.965 | 52.789 | 49.656 | 1.00 | 49.47 |
| ATOM | 1909 | N | GLY | 259 | 5.181 | 50.952 | 49.174 | 1.00 | 47.70 |
| ATOM | 1910 | CA | GLY | 259 | 4.764 | 50.240 | 50.371 | 1.00 | 45.91 |
| ATOM | 1911 | C | GLY | 259 | 3.303 | 49.824 | 50.430 | 1.00 | 46.65 |
| ATOM | 1912 | O | GLY | 259 | 2.822 | 49.373 | 51.471 | 1.00 | 46.58 |
| ATOM | 1913 | N | SER | 260 | 2.594 | 49.963 | 49.316 | 1.00 | 44.76 |
| ATOM | 1914 | CA | SER | 260 | 1.181 | 49.598 | 49.272 | 1.00 | 44.73 |
| ATOM | 1915 | CB | SER | 260 | 0.542 | 50.101 | 47.970 | 1.00 | 48.61 |
| ATOM | 1916 | OG | SER | 260 | 1.249 | 49.636 | 46.837 | 1.00 | 55.53 |
| ATOM | 1917 | C | SER | 260 | 0.973 | 48.097 | 49.410 | 1.00 | 42.54 |
| ATOM | 1918 | O | SER | 260 | −0.096 | 47.647 | 49.822 | 1.00 | 39.63 |
| ATOM | 1919 | N | LEU | 261 | 2.000 | 47.322 | 49.077 | 1.00 | 42.90 |
| ATOM | 1920 | CA | LEU | 261 | 1.908 | 45.869 | 49.168 | 1.00 | 41.26 |
| ATOM | 1921 | CB | LEU | 261 | 3.085 | 45.213 | 48.447 | 1.00 | 40.47 |
| ATOM | 1922 | CG | LEU | 261 | 2.761 | 44.035 | 47.524 | 1.00 | 46.45 |
| ATOM | 1923 | CD1 | LEU | 261 | 4.050 | 43.478 | 46.962 | 1.00 | 54.12 |
| ATOM | 1924 | CD2 | LEU | 261 | 2.013 | 42.958 | 48.269 | 1.00 | 45.49 |
| ATOM | 1925 | C | LEU | 261 | 1.895 | 45.432 | 50.623 | 1.00 | 40.52 |
| ATOM | 1926 | O | LEU | 261 | 1.258 | 44.443 | 50.980 | 1.00 | 37.26 |
| ATOM | 1927 | N | ARG | 262 | 2.598 | 46.178 | 51.465 | 1.00 | 45.69 |
| ATOM | 1928 | CA | ARG | 262 | 2.658 | 45.848 | 52.878 | 1.00 | 49.34 |
| ATOM | 1929 | CB | ARG | 262 | 3.846 | 46.544 | 53.531 | 1.00 | 51.67 |
| ATOM | 1930 | CG | ARG | 262 | 4.057 | 46.125 | 54.965 | 1.00 | 65.76 |
| ATOM | 1931 | CD | ARG | 262 | 5.455 | 45.595 | 55.153 | 1.00 | 76.52 |
| ATOM | 1932 | NE | ARG | 262 | 6.447 | 46.611 | 54.830 | 1.00 | 86.10 |
| ATOM | 1933 | CZ | ARG | 262 | 6.616 | 47.732 | 55.521 | 1.00 | 92.52 |
| ATOM | 1934 | NH1 | ARG | 262 | 5.855 | 47.976 | 56.582 | 1.00 | 93.92 |
| ATOM | 1935 | NH2 | ARG | 262 | 7.539 | 48.612 | 55.146 | 1.00 | 96.84 |
| ATOM | 1936 | C | ARG | 262 | 1.372 | 46.226 | 53.612 | 1.00 | 52.75 |
| ATOM | 1937 | O | ARG | 262 | 0.908 | 45.489 | 54.484 | 1.00 | 50.33 |
| ATOM | 1938 | N | ARG | 263 | 0.795 | 47.373 | 53.266 | 1.00 | 52.70 |
| ATOM | 1939 | CA | ARG | 263 | −0.439 | 47.810 | 53.906 | 1.00 | 56.54 |
| ATOM | 1940 | CB | ARG | 263 | −0.903 | 49.136 | 53.308 | 1.00 | 61.58 |
| ATOM | 1941 | CG | ARG | 263 | 0.097 | 50.257 | 53.495 | 1.00 | 65.52 |
| ATOM | 1942 | CD | ARG | 263 | −0.191 | 51.416 | 52.560 | 1.00 | 72.22 |
| ATOM | 1943 | NE | ARG | 263 | 0.953 | 52.318 | 52.472 | 1.00 | 79.00 |
| ATOM | 1944 | CZ | ARG | 263 | 1.176 | 53.151 | 51.460 | 1.00 | 80.90 |
| ATOM | 1945 | NH1 | ARG | 263 | 0.329 | 53.204 | 50.438 | 1.00 | 83.68 |
| ATOM | 1946 | NH2 | ARG | 263 | 2.255 | 53.923 | 51.464 | 1.00 | 83.28 |
| ATOM | 1947 | C | ARG | 263 | −1.513 | 46.745 | 53.718 | 1.00 | 58.44 |
| ATOM | 1948 | O | ARG | 263 | −2.329 | 46.504 | 54.604 | 1.00 | 60.04 |
| ATOM | 1949 | N | ALA | 264 | −1.506 | 46.103 | 52.556 | 1.00 | 55.52 |
| ATOM | 1950 | CA | ALA | 264 | −2.472 | 45.057 | 52.266 | 1.00 | 51.57 |

TABLE 2-continued

Atomic coordinates on the three-dimensional crystal structure of the FabK-
FMN complex having the amino acid sequences 2-312 of SEQ ID NO: 1

| A | B | C | D | E | F | G | H | I | J |
|---|---|---|---|---|---|---|---|---|---|
| ATOM | 1951 | CB | ALA | 264 | −2.521 | 44.793 | 50.764 | 1.00 | 55.03 |
| ATOM | 1952 | C | ALA | 264 | −2.092 | 43.782 | 53.010 | 1.00 | 49.27 |
| ATOM | 1953 | O | ALA | 264 | −2.834 | 43.310 | 53.867 | 1.00 | 49.72 |
| ATOM | 1954 | N | VAL | 265 | −0.922 | 43.240 | 52.683 | 1.00 | 44.95 |
| ATOM | 1955 | CA | VAL | 265 | −0.429 | 42.007 | 53.288 | 1.00 | 43.91 |
| ATOM | 1956 | CB | VAL | 265 | 0.986 | 41.665 | 52.753 | 1.00 | 45.09 |
| ATOM | 1957 | CG1 | VAL | 265 | 1.607 | 40.539 | 53.581 | 1.00 | 32.44 |
| ATOM | 1958 | CG2 | VAL | 265 | 0.901 | 41.267 | 51.286 | 1.00 | 38.96 |
| ATOM | 1959 | C | VAL | 265 | −0.363 | 42.004 | 54.815 | 1.00 | 47.38 |
| ATOM | 1960 | O | VAL | 265 | −0.825 | 41.064 | 55.469 | 1.00 | 42.38 |
| ATOM | 1961 | N | VAL | 266 | 0.224 | 43.059 | 55.367 | 1.00 | 52.57 |
| ATOM | 1962 | CA | VAL | 266 | 0.409 | 43.187 | 56.805 | 1.00 | 58.15 |
| ATOM | 1963 | CB | VAL | 266 | 1.733 | 43.936 | 57.086 | 1.00 | 56.84 |
| ATOM | 1964 | CG1 | VAL | 266 | 1.915 | 44.168 | 58.580 | 1.00 | 57.97 |
| ATOM | 1965 | CG2 | VAL | 266 | 2.900 | 43.122 | 56.531 | 1.00 | 52.00 |
| ATOM | 1966 | C | VAL | 266 | −0.740 | 43.859 | 57.562 | 1.00 | 60.50 |
| ATOM | 1967 | O | VAL | 266 | −1.196 | 43.349 | 58.588 | 1.00 | 59.24 |
| ATOM | 1968 | N | GLU | 267 | −1.211 | 44.994 | 57.057 | 1.00 | 64.25 |
| ATOM | 1969 | CA | GLU | 267 | −2.297 | 45.714 | 57.710 | 1.00 | 68.77 |
| ATOM | 1970 | CB | GLU | 267 | −2.073 | 47.228 | 57.591 | 1.00 | 80.73 |
| ATOM | 1971 | CG | GLU | 267 | −1.203 | 47.844 | 58.685 | 1.00 | 93.51 |
| ATOM | 1972 | CD | GLU | 267 | 0.207 | 47.289 | 58.716 | 1.00 | 100.60 |
| ATOM | 1973 | OE1 | GLU | 267 | 0.920 | 47.412 | 57.699 | 1.00 | 107.32 |
| ATOM | 1974 | OE2 | GLU | 267 | 0.605 | 46.735 | 59.762 | 1.00 | 104.96 |
| ATOM | 1975 | C | GLU | 267 | −3.693 | 45.369 | 57.186 | 1.00 | 68.59 |
| ATOM | 1976 | O | GLU | 267 | −4.690 | 45.711 | 57.823 | 1.00 | 68.32 |
| ATOM | 1977 | N | GLY | 268 | −3.769 | 44.693 | 56.039 | 1.00 | 66.62 |
| ATOM | 1978 | CA | GLY | 268 | −5.065 | 44.348 | 55.470 | 1.00 | 61.66 |
| ATOM | 1979 | C | GLY | 268 | −5.907 | 45.594 | 55.254 | 1.00 | 59.95 |
| ATOM | 1980 | O | GLY | 268 | −7.120 | 45.600 | 55.486 | 1.00 | 58.23 |
| ATOM | 1981 | N | ASP | 269 | −5.242 | 46.653 | 54.798 | 1.00 | 59.53 |
| ATOM | 1982 | CA | ASP | 269 | −5.866 | 47.950 | 54.558 | 1.00 | 60.72 |
| ATOM | 1983 | CB | ASP | 269 | −4.875 | 49.062 | 54.915 | 1.00 | 63.37 |
| ATOM | 1984 | CG | ASP | 269 | −5.388 | 50.437 | 54.558 | 1.00 | 66.52 |
| ATOM | 1985 | OD1 | ASP | 269 | −6.441 | 50.835 | 55.095 | 1.00 | 68.23 |
| ATOM | 1986 | OD2 | ASP | 269 | −4.737 | 51.118 | 53.738 | 1.00 | 66.86 |
| ATOM | 1987 | C | ASP | 269 | −6.320 | 48.120 | 53.121 | 1.00 | 60.28 |
| ATOM | 1988 | O | ASP | 269 | −5.504 | 48.158 | 52.208 | 1.00 | 61.10 |
| ATOM | 1989 | N | LEU | 270 | −7.623 | 48.235 | 52.918 | 1.00 | 61.52 |
| ATOM | 1990 | CA | LEU | 270 | −8.145 | 48.398 | 51.574 | 1.00 | 68.82 |
| ATOM | 1991 | CB | LEU | 270 | −9.627 | 48.035 | 51.544 | 1.00 | 72.25 |
| ATOM | 1992 | CG | LEU | 270 | −9.958 | 46.550 | 51.704 | 1.00 | 76.27 |
| ATOM | 1993 | CD1 | LEU | 270 | −9.347 | 45.994 | 52.979 | 1.00 | 76.12 |
| ATOM | 1994 | CD2 | LEU | 270 | −11.465 | 46.386 | 51.719 | 1.00 | 82.28 |
| ATOM | 1995 | C | LEU | 270 | −7.950 | 49.826 | 51.088 | 1.00 | 71.21 |
| ATOM | 1996 | O | LEU | 270 | −7.704 | 50.064 | 49.904 | 1.00 | 76.60 |
| ATOM | 1997 | N | GLU | 271 | −8.058 | 50.770 | 52.015 | 1.00 | 71.67 |
| ATOM | 1998 | CA | GLU | 271 | −7.907 | 52.190 | 51.720 | 1.00 | 71.85 |
| ATOM | 1999 | CB | GLU | 271 | −7.852 | 52.984 | 53.028 | 1.00 | 75.96 |
| ATOM | 2000 | CG | GLU | 271 | −9.211 | 53.279 | 53.641 | 1.00 | 82.22 |
| ATOM | 2001 | CD | GLU | 271 | −10.242 | 52.196 | 53.360 | 1.00 | 86.17 |
| ATOM | 2002 | OE1 | GLU | 271 | −9.983 | 51.012 | 53.673 | 1.00 | 88.62 |
| ATOM | 2003 | OE2 | GLU | 271 | −11.320 | 52.534 | 52.827 | 1.00 | 85.53 |
| ATOM | 2004 | C | GLU | 271 | −6.679 | 52.513 | 50.878 | 1.00 | 70.49 |
| ATOM | 2005 | O | GLU | 271 | −6.773 | 53.241 | 49.887 | 1.00 | 69.55 |
| ATOM | 2006 | N | ARG | 272 | −5.528 | 51.978 | 51.277 | 1.00 | 66.49 |
| ATOM | 2007 | CA | ARG | 272 | −4.290 | 52.231 | 50.550 | 1.00 | 65.46 |
| ATOM | 2008 | CB | ARG | 272 | −3.448 | 53.294 | 51.259 | 1.00 | 75.37 |
| ATOM | 2009 | CG | ARG | 272 | −4.121 | 54.641 | 51.433 | 1.00 | 87.93 |
| ATOM | 2010 | CD | ARG | 272 | −3.161 | 55.628 | 52.083 | 1.00 | 97.36 |
| ATOM | 2011 | NE | ARG | 272 | −2.436 | 55.027 | 53.203 | 1.00 | 109.06 |
| ATOM | 2012 | CZ | ARG | 272 | −3.006 | 54.534 | 54.300 | 1.00 | 115.55 |
| ATOM | 2013 | NH1 | ARG | 272 | −4.325 | 54.565 | 54.447 | 1.00 | 118.97 |
| ATOM | 2014 | NH2 | ARG | 272 | −2.254 | 53.997 | 55.252 | 1.00 | 120.05 |
| ATOM | 2015 | C | ARG | 272 | −3.448 | 50.981 | 50.390 | 1.00 | 58.78 |
| ATOM | 2016 | O | ARG | 272 | −2.224 | 51.055 | 50.400 | 1.00 | 55.48 |
| ATOM | 2017 | N | GLY | 273 | −4.096 | 49.835 | 50.245 | 1.00 | 52.07 |
| ATOM | 2018 | CA | GLY | 273 | −3.343 | 48.608 | 50.079 | 1.00 | 51.48 |
| ATOM | 2019 | C | GLY | 273 | −3.416 | 48.046 | 48.671 | 1.00 | 47.67 |
| ATOM | 2020 | O | GLY | 273 | −4.407 | 48.239 | 47.963 | 1.00 | 48.42 |
| ATOM | 2021 | N | SER | 274 | −2.354 | 47.369 | 48.253 | 1.00 | 45.87 |
| ATOM | 2022 | CA | SER | 274 | −2.324 | 46.744 | 46.939 | 1.00 | 41.91 |
| ATOM | 2023 | CB | SER | 274 | −1.026 | 47.058 | 46.201 | 1.00 | 39.62 |
| ATOM | 2024 | OG | SER | 274 | −1.009 | 48.398 | 45.763 | 1.00 | 43.81 |

TABLE 2-continued

Atomic coordinates on the three-dimensional crystal structure of the FabK-FMN complex having the amino acid sequences 2-312 of SEQ ID NO: 1

| A | B | C | D | E | F | G | H | I | J |
|---|---|---|---|---|---|---|---|---|---|
| ATOM | 2025 | C | SER | 274 | −2.425 | 45.250 | 47.144 | 1.00 | 38.32 |
| ATOM | 2026 | O | SER | 274 | −1.458 | 44.608 | 47.539 | 1.00 | 43.04 |
| ATOM | 2027 | N | PHE | 275 | −3.602 | 44.697 | 46.899 | 1.00 | 30.68 |
| ATOM | 2028 | CA | PHE | 275 | −3.783 | 43.271 | 47.059 | 1.00 | 34.67 |
| ATOM | 2029 | CB | PHE | 275 | −5.207 | 42.967 | 47.517 | 1.00 | 34.23 |
| ATOM | 2030 | CG | PHE | 275 | −5.568 | 43.609 | 48.824 | 1.00 | 40.24 |
| ATOM | 2031 | CD1 | PHE | 275 | −5.641 | 44.991 | 48.938 | 1.00 | 41.93 |
| ATOM | 2032 | CD2 | PHE | 275 | −5.817 | 42.833 | 49.949 | 1.00 | 42.71 |
| ATOM | 2033 | CE1 | PHE | 275 | −5.955 | 45.592 | 50.155 | 1.00 | 50.17 |
| ATOM | 2034 | CE2 | PHE | 275 | −6.132 | 43.422 | 51.172 | 1.00 | 46.60 |
| ATOM | 2035 | CZ | PHE | 275 | −6.201 | 44.801 | 51.277 | 1.00 | 46.73 |
| ATOM | 2036 | C | PHE | 275 | −3.502 | 42.591 | 45.729 | 1.00 | 36.27 |
| ATOM | 2037 | O | PHE | 275 | −4.411 | 42.363 | 44.934 | 1.00 | 40.95 |
| ATOM | 2038 | N | MET | 276 | −2.236 | 42.285 | 45.470 | 1.00 | 27.92 |
| ATOM | 2039 | CA | MET | 276 | −1.895 | 41.619 | 44.230 | 1.00 | 25.92 |
| ATOM | 2040 | CB | MET | 276 | −0.391 | 41.462 | 44.092 | 1.00 | 29.74 |
| ATOM | 2041 | CG | MET | 276 | 0.348 | 42.766 | 44.044 | 1.00 | 30.73 |
| ATOM | 2042 | SD | MET | 276 | 2.075 | 42.493 | 43.693 | 1.00 | 42.99 |
| ATOM | 2043 | CE | MET | 276 | 2.189 | 43.355 | 42.144 | 1.00 | 51.12 |
| ATOM | 2044 | C | MET | 276 | −2.547 | 40.254 | 44.212 | 1.00 | 30.73 |
| ATOM | 2045 | O | MET | 276 | −2.474 | 39.503 | 45.191 | 1.00 | 28.96 |
| ATOM | 2046 | N | VAL | 277 | −3.198 | 39.942 | 43.097 | 1.00 | 30.73 |
| ATOM | 2047 | CA | VAL | 277 | −3.873 | 38.664 | 42.925 | 1.00 | 33.83 |
| ATOM | 2048 | CB | VAL | 277 | −5.266 | 38.670 | 43.577 | 1.00 | 32.36 |
| ATOM | 2049 | CG1 | VAL | 277 | −5.139 | 38.617 | 45.084 | 1.00 | 38.57 |
| ATOM | 2050 | CG2 | VAL | 277 | −6.021 | 39.923 | 43.155 | 1.00 | 40.98 |
| ATOM | 2051 | C | VAL | 277 | −4.055 | 38.336 | 41.448 | 1.00 | 33.90 |
| ATOM | 2052 | O | VAL | 277 | −4.055 | 39.225 | 40.589 | 1.00 | 26.55 |
| ATOM | 2053 | N | GLY | 278 | −4.190 | 37.046 | 41.162 | 1.00 | 29.26 |
| ATOM | 2054 | CA | GLY | 278 | −4.406 | 36.612 | 39.796 | 1.00 | 26.97 |
| ATOM | 2055 | C | GLY | 278 | −5.887 | 36.333 | 39.639 | 1.00 | 29.36 |
| ATOM | 2056 | O | GLY | 278 | −6.587 | 36.158 | 40.644 | 1.00 | 22.99 |
| ATOM | 2057 | N | GLN | 279 | −6.368 | 36.303 | 38.393 | 1.00 | 28.24 |
| ATOM | 2058 | CA | GLN | 279 | −7.776 | 36.029 | 38.113 | 1.00 | 23.16 |
| ATOM | 2059 | CB | GLN | 279 | −8.048 | 36.060 | 36.616 | 1.00 | 19.51 |
| ATOM | 2060 | CG | GLN | 279 | −7.372 | 37.183 | 35.873 | 1.00 | 22.93 |
| ATOM | 2061 | CD | GLN | 279 | −7.979 | 37.366 | 34.510 | 1.00 | 13.60 |
| ATOM | 2062 | OE1 | GLN | 279 | −8.161 | 36.400 | 33.765 | 1.00 | 19.30 |
| ATOM | 2063 | NE2 | GLN | 279 | −8.307 | 38.599 | 34.174 | 1.00 | 11.53 |
| ATOM | 2064 | C | GLN | 279 | −8.152 | 34.647 | 38.630 | 1.00 | 26.58 |
| ATOM | 2065 | O | GLN | 279 | −9.335 | 34.299 | 38.681 | 1.00 | 19.54 |
| ATOM | 2066 | N | SER | 280 | −7.135 | 33.863 | 38.985 | 1.00 | 24.60 |
| ATOM | 2067 | CA | SER | 280 | −7.342 | 32.522 | 39.502 | 1.00 | 27.86 |
| ATOM | 2068 | CB | SER | 280 | −6.001 | 31.818 | 39.687 | 1.00 | 29.47 |
| ATOM | 2069 | OG | SER | 280 | −5.175 | 32.534 | 40.592 | 1.00 | 37.69 |
| ATOM | 2070 | C | SER | 280 | −8.080 | 32.576 | 40.839 | 1.00 | 29.75 |
| ATOM | 2071 | O | SER | 280 | −8.631 | 31.571 | 41.292 | 1.00 | 27.78 |
| ATOM | 2072 | N | ALA | 281 | −8.097 | 33.751 | 41.464 | 1.00 | 28.69 |
| ATOM | 2073 | CA | ALA | 281 | −8.786 | 33.918 | 42.747 | 1.00 | 33.36 |
| ATOM | 2074 | CB | ALA | 281 | −8.634 | 35.361 | 43.242 | 1.00 | 31.82 |
| ATOM | 2075 | C | ALA | 281 | −10.270 | 33.559 | 42.619 | 1.00 | 30.60 |
| ATOM | 2076 | O | ALA | 281 | −10.916 | 33.147 | 43.593 | 1.00 | 26.47 |
| ATOM | 2077 | N | GLY | 282 | −10.803 | 33.718 | 41.411 | 1.00 | 25.12 |
| ATOM | 2078 | CA | GLY | 282 | −12.197 | 33.404 | 41.161 | 1.00 | 27.67 |
| ATOM | 2079 | C | GLY | 282 | −12.479 | 31.912 | 41.134 | 1.00 | 28.50 |
| ATOM | 2080 | O | GLY | 282 | −13.616 | 31.492 | 40.934 | 1.00 | 36.00 |
| ATOM | 2081 | N | LEU | 283 | −11.444 | 31.106 | 41.318 | 1.00 | 37.00 |
| ATOM | 2082 | CA | LEU | 283 | −11.596 | 29.660 | 41.332 | 1.00 | 38.97 |
| ATOM | 2083 | CB | LEU | 283 | −10.577 | 29.008 | 40.397 | 1.00 | 36.26 |
| ATOM | 2084 | CG | LEU | 283 | −10.462 | 29.552 | 38.969 | 1.00 | 47.50 |
| ATOM | 2085 | CD1 | LEU | 283 | −9.286 | 28.871 | 38.281 | 1.00 | 48.03 |
| ATOM | 2086 | CD2 | LEU | 283 | −11.754 | 29.324 | 38.182 | 1.00 | 42.84 |
| ATOM | 2087 | C | LEU | 283 | −11.338 | 29.204 | 42.766 | 1.00 | 42.48 |
| ATOM | 2088 | O | LEU | 283 | −11.234 | 28.011 | 43.046 | 1.00 | 40.37 |
| ATOM | 2089 | N | ILE | 284 | −11.227 | 30.172 | 43.671 | 1.00 | 41.35 |
| ATOM | 2090 | CA | ILE | 284 | −10.970 | 29.876 | 45.071 | 1.00 | 42.44 |
| ATOM | 2091 | CB | ILE | 284 | −9.707 | 30.602 | 45.550 | 1.00 | 44.67 |
| ATOM | 2092 | CG2 | ILE | 284 | −9.463 | 30.314 | 47.019 | 1.00 | 44.22 |
| ATOM | 2093 | CG1 | ILE | 284 | −8.516 | 30.124 | 44.712 | 1.00 | 47.91 |
| ATOM | 2094 | CD1 | ILE | 284 | −7.214 | 30.819 | 45.010 | 1.00 | 49.18 |
| ATOM | 2095 | C | ILE | 284 | −12.175 | 30.267 | 45.918 | 1.00 | 44.88 |
| ATOM | 2096 | O | ILE | 284 | −12.632 | 31.423 | 45.896 | 1.00 | 33.54 |
| ATOM | 2097 | N | ASP | 285 | −12.680 | 29.278 | 46.657 | 1.00 | 49.54 |
| ATOM | 2098 | CA | ASP | 285 | −13.863 | 29.444 | 47.494 | 1.00 | 59.31 |

TABLE 2-continued

Atomic coordinates on the three-dimensional crystal structure of the FabK-
FMN complex having the amino acid sequences 2-312 of SEQ ID NO: 1

| A | B | C | D | E | F | G | H | I | J |
|---|---|---|---|---|---|---|---|---|---|
| ATOM | 2099 | CB | ASP | 285 | −14.957 | 28.505 | 46.994 | 1.00 | 66.02 |
| ATOM | 2100 | CG | ASP | 285 | −15.104 | 28.544 | 45.486 | 1.00 | 74.35 |
| ATOM | 2101 | OD1 | ASP | 285 | −15.452 | 29.621 | 44.952 | 1.00 | 74.08 |
| ATOM | 2102 | OD2 | ASP | 285 | −14.862 | 27.502 | 44.836 | 1.00 | 76.23 |
| ATOM | 2103 | C | ASP | 285 | −13.648 | 29.212 | 48.987 | 1.00 | 59.34 |
| ATOM | 2104 | O | ASP | 285 | −14.442 | 29.673 | 49.804 | 1.00 | 61.05 |
| ATOM | 2105 | N | GLU | 286 | −12.590 | 28.496 | 49.348 | 1.00 | 57.65 |
| ATOM | 2106 | CA | GLU | 286 | −12.322 | 28.242 | 50.757 | 1.00 | 58.04 |
| ATOM | 2107 | CB | GLU | 286 | −12.930 | 26.896 | 51.163 | 1.00 | 71.28 |
| ATOM | 2108 | CG | GLU | 286 | −12.955 | 25.856 | 50.050 | 1.00 | 87.57 |
| ATOM | 2109 | CD | GLU | 286 | −11.584 | 25.588 | 49.467 | 1.00 | 97.19 |
| ATOM | 2110 | OE1 | GLU | 286 | −10.677 | 25.202 | 50.237 | 1.00 | 100.90 |
| ATOM | 2111 | OE2 | GLU | 286 | −11.413 | 25.764 | 48.241 | 1.00 | 99.54 |
| ATOM | 2112 | C | GLU | 286 | −10.837 | 28.274 | 51.095 | 1.00 | 52.65 |
| ATOM | 2113 | O | GLU | 286 | −9.983 | 28.215 | 50.205 | 1.00 | 44.96 |
| ATOM | 2114 | N | ILE | 287 | −10.538 | 28.386 | 52.386 | 1.00 | 50.54 |
| ATOM | 2115 | CA | ILE | 287 | −9.158 | 28.415 | 52.860 | 1.00 | 51.69 |
| ATOM | 2116 | CB | ILE | 287 | −8.973 | 29.398 | 54.038 | 1.00 | 48.38 |
| ATOM | 2117 | CG2 | ILE | 287 | −7.504 | 29.499 | 54.393 | 1.00 | 41.91 |
| ATOM | 2118 | CG1 | ILE | 287 | −9.553 | 30.771 | 53.689 | 1.00 | 51.02 |
| ATOM | 2119 | CD1 | ILE | 287 | −8.833 | 31.497 | 52.579 | 1.00 | 58.10 |
| ATOM | 2120 | C | ILE | 287 | −8.811 | 27.028 | 53.376 | 1.00 | 54.20 |
| ATOM | 2121 | O | ILE | 287 | −9.328 | 26.604 | 54.408 | 1.00 | 60.06 |
| ATOM | 2122 | N | LYS | 288 | −7.944 | 26.317 | 52.666 | 1.00 | 49.77 |
| ATOM | 2123 | CA | LYS | 288 | −7.556 | 24.979 | 53.101 | 1.00 | 49.27 |
| ATOM | 2124 | CB | LYS | 288 | −7.951 | 23.940 | 52.043 | 1.00 | 47.95 |
| ATOM | 2125 | CG | LYS | 288 | −7.649 | 24.333 | 50.613 | 1.00 | 52.09 |
| ATOM | 2126 | CD | LYS | 288 | −7.732 | 23.123 | 49.675 | 1.00 | 60.13 |
| ATOM | 2127 | CE | LYS | 288 | −9.148 | 22.559 | 49.535 | 1.00 | 59.30 |
| ATOM | 2128 | NZ | LYS | 288 | −10.009 | 23.323 | 48.583 | 1.00 | 57.36 |
| ATOM | 2129 | C | LYS | 288 | −6.064 | 24.881 | 53.417 | 1.00 | 46.95 |
| ATOM | 2130 | O | LYS | 288 | −5.285 | 25.760 | 53.052 | 1.00 | 40.56 |
| ATOM | 2131 | N | PRO | 289 | −5.653 | 23.820 | 54.134 | 1.00 | 47.87 |
| ATOM | 2132 | CD | PRO | 289 | −6.481 | 22.753 | 54.725 | 1.00 | 47.41 |
| ATOM | 2133 | CA | PRO | 289 | −4.244 | 23.632 | 54.488 | 1.00 | 43.91 |
| ATOM | 2134 | CB | PRO | 289 | −4.302 | 22.516 | 55.524 | 1.00 | 47.12 |
| ATOM | 2135 | CG | PRO | 289 | −5.455 | 21.701 | 55.057 | 1.00 | 49.39 |
| ATOM | 2136 | C | PRO | 289 | −3.410 | 23.257 | 53.266 | 1.00 | 43.15 |
| ATOM | 2137 | O | PRO | 289 | −3.857 | 22.500 | 52.404 | 1.00 | 41.84 |
| ATOM | 2138 | N | VAL | 290 | −2.197 | 23.790 | 53.199 | 1.00 | 40.31 |
| ATOM | 2139 | CA | VAL | 290 | −1.304 | 23.532 | 52.076 | 1.00 | 43.12 |
| ATOM | 2140 | CB | VAL | 290 | 0.115 | 24.010 | 52.405 | 1.00 | 37.99 |
| ATOM | 2141 | CG1 | VAL | 290 | 1.098 | 23.531 | 51.350 | 1.00 | 44.94 |
| ATOM | 2142 | CG2 | VAL | 290 | 0.120 | 25.525 | 52.472 | 1.00 | 40.96 |
| ATOM | 2143 | C | VAL | 290 | −1.273 | 22.067 | 51.670 | 1.00 | 41.36 |
| ATOM | 2144 | O | VAL | 290 | −1.428 | 21.732 | 50.494 | 1.00 | 41.41 |
| ATOM | 2145 | N | LYS | 291 | −1.076 | 21.203 | 52.656 | 1.00 | 41.97 |
| ATOM | 2146 | CA | LYS | 291 | −1.028 | 19.767 | 52.427 | 1.00 | 40.19 |
| ATOM | 2147 | CB | LYS | 291 | −1.001 | 19.028 | 53.770 | 1.00 | 50.55 |
| ATOM | 2148 | CG | LYS | 291 | −0.577 | 17.562 | 53.693 | 1.00 | 60.15 |
| ATOM | 2149 | CD | LYS | 291 | 0.940 | 17.426 | 53.688 | 1.00 | 71.13 |
| ATOM | 2150 | CE | LYS | 291 | 1.377 | 15.970 | 53.630 | 1.00 | 71.72 |
| ATOM | 2151 | NZ | LYS | 291 | 1.035 | 15.334 | 52.328 | 1.00 | 80.34 |
| ATOM | 2152 | C | LYS | 291 | −2.255 | 19.333 | 51.624 | 1.00 | 38.76 |
| ATOM | 2153 | O | LYS | 291 | −2.128 | 18.648 | 50.607 | 1.00 | 31.87 |
| ATOM | 2154 | N | GLN | 292 | −3.434 | 19.753 | 52.076 | 1.00 | 31.52 |
| ATOM | 2155 | CA | GLN | 292 | −4.677 | 19.389 | 51.413 | 1.00 | 38.55 |
| ATOM | 2156 | CB | GLN | 292 | −5.877 | 19.951 | 52.168 | 1.00 | 36.26 |
| ATOM | 2157 | CG | GLN | 292 | −7.188 | 19.339 | 51.716 | 1.00 | 49.25 |
| ATOM | 2158 | CD | GLN | 292 | −8.389 | 19.916 | 52.445 | 1.00 | 60.54 |
| ATOM | 2159 | OE1 | GLN | 292 | −8.799 | 21.051 | 52.198 | 1.00 | 60.82 |
| ATOM | 2160 | NE2 | GLN | 292 | −8.955 | 19.135 | 53.358 | 1.00 | 63.12 |
| ATOM | 2161 | C | GLN | 292 | −4.718 | 19.879 | 49.973 | 1.00 | 40.88 |
| ATOM | 2162 | O | GLN | 292 | −5.039 | 19.116 | 49.056 | 1.00 | 37.80 |
| ATOM | 2163 | N | ILE | 293 | −4.396 | 21.157 | 49.792 | 1.00 | 39.78 |
| ATOM | 2164 | CA | ILE | 293 | −4.373 | 21.793 | 48.486 | 1.00 | 32.82 |
| ATOM | 2165 | CB | ILE | 293 | −3.695 | 23.170 | 48.593 | 1.00 | 29.52 |
| ATOM | 2166 | CG2 | ILE | 293 | −3.447 | 23.751 | 47.221 | 1.00 | 34.11 |
| ATOM | 2167 | CG1 | ILE | 293 | −4.584 | 24.100 | 49.420 | 1.00 | 35.86 |
| ATOM | 2168 | CD1 | ILE | 293 | −4.123 | 25.547 | 49.472 | 1.00 | 36.02 |
| ATOM | 2169 | C | ILE | 293 | −3.636 | 20.921 | 47.469 | 1.00 | 35.47 |
| ATOM | 2170 | O | ILE | 293 | −4.157 | 20.619 | 46.399 | 1.00 | 29.69 |
| ATOM | 2171 | N | ILE | 294 | −2.427 | 20.507 | 47.825 | 1.00 | 37.34 |
| ATOM | 2172 | CA | ILE | 294 | −1.607 | 19.674 | 46.958 | 1.00 | 38.84 |

TABLE 2-continued

Atomic coordinates on the three-dimensional crystal structure of the FabK-FMN complex having the amino acid sequences 2-312 of SEQ ID NO: 1

| A | B | C | D | E | F | G | H | I | J |
|---|---|---|---|---|---|---|---|---|---|
| ATOM | 2173 | CB | ILE | 294 | −0.201 | 19.526 | 47.561 | 1.00 | 34.23 |
| ATOM | 2174 | CG2 | ILE | 294 | 0.549 | 18.385 | 46.900 | 1.00 | 35.19 |
| ATOM | 2175 | CG1 | ILE | 294 | 0.535 | 20.854 | 47.403 | 1.00 | 33.86 |
| ATOM | 2176 | CD1 | ILE | 294 | 1.942 | 20.864 | 47.902 | 1.00 | 32.69 |
| ATOM | 2177 | C | ILE | 294 | −2.221 | 18.297 | 46.705 | 1.00 | 44.75 |
| ATOM | 2178 | O | ILE | 294 | −2.100 | 17.740 | 45.608 | 1.00 | 38.48 |
| ATOM | 2179 | N | GLU | 295 | −2.873 | 17.753 | 47.728 | 1.00 | 49.81 |
| ATOM | 2180 | CA | GLU | 295 | −3.519 | 16.449 | 47.620 | 1.00 | 56.63 |
| ATOM | 2181 | CB | GLU | 295 | −4.180 | 16.066 | 48.949 | 1.00 | 68.21 |
| ATOM | 2182 | CG | GLU | 295 | −3.256 | 16.080 | 50.150 | 1.00 | 83.84 |
| ATOM | 2183 | CD | GLU | 295 | −2.179 | 15.017 | 50.076 | 1.00 | 90.91 |
| ATOM | 2184 | OE1 | GLU | 295 | −2.524 | 13.819 | 50.134 | 1.00 | 96.06 |
| ATOM | 2185 | OE2 | GLU | 295 | −0.988 | 15.378 | 49.957 | 1.00 | 97.00 |
| ATOM | 2186 | C | GLU | 295 | −4.598 | 16.588 | 46.560 | 1.00 | 54.61 |
| ATOM | 2187 | O | GLU | 295 | −4.574 | 15.922 | 45.524 | 1.00 | 49.11 |
| ATOM | 2188 | N | ASP | 296 | −5.541 | 17.479 | 46.847 | 1.00 | 54.85 |
| ATOM | 2189 | CA | ASP | 296 | −6.659 | 17.753 | 45.963 | 1.00 | 55.72 |
| ATOM | 2190 | CB | ASP | 296 | −7.415 | 19.003 | 46.434 | 1.00 | 65.58 |
| ATOM | 2191 | CG | ASP | 296 | −7.948 | 18.873 | 47.854 | 1.00 | 74.80 |
| ATOM | 2192 | OD1 | ASP | 296 | −8.671 | 17.894 | 48.137 | 1.00 | 75.85 |
| ATOM | 2193 | OD2 | ASP | 296 | −7.649 | 19.758 | 48.686 | 1.00 | 81.76 |
| ATOM | 2194 | C | ASP | 296 | −6.195 | 17.962 | 44.531 | 1.00 | 51.84 |
| ATOM | 2195 | O | ASP | 296 | −6.640 | 17.265 | 43.619 | 1.00 | 50.73 |
| ATOM | 2196 | N | ILE | 297 | −5.304 | 18.928 | 44.338 | 1.00 | 41.71 |
| ATOM | 2197 | CA | ILE | 297 | −4.808 | 19.223 | 43.005 | 1.00 | 37.91 |
| ATOM | 2198 | CB | ILE | 297 | −3.696 | 20.305 | 43.038 | 1.00 | 33.50 |
| ATOM | 2199 | CG2 | ILE | 297 | −3.130 | 20.513 | 41.651 | 1.00 | 30.48 |
| ATOM | 2200 | CG1 | ILE | 297 | −4.280 | 21.621 | 43.556 | 1.00 | 34.71 |
| ATOM | 2201 | CD1 | ILE | 297 | −3.317 | 22.775 | 43.516 | 1.00 | 37.99 |
| ATOM | 2202 | C | ILE | 297 | −4.286 | 17.971 | 42.314 | 1.00 | 32.11 |
| ATOM | 2203 | O | ILE | 297 | −4.549 | 17.750 | 41.128 | 1.00 | 30.04 |
| ATOM | 2204 | N | LEU | 298 | −3.556 | 17.144 | 43.047 | 1.00 | 30.80 |
| ATOM | 2205 | CA | LEU | 298 | −3.033 | 15.926 | 42.453 | 1.00 | 33.15 |
| ATOM | 2206 | CB | LEU | 298 | −2.005 | 15.281 | 43.377 | 1.00 | 40.08 |
| ATOM | 2207 | CG | LEU | 298 | −0.569 | 15.648 | 43.005 | 1.00 | 45.88 |
| ATOM | 2208 | CD1 | LEU | 298 | −0.471 | 17.150 | 42.837 | 1.00 | 46.47 |
| ATOM | 2209 | CD2 | LEU | 298 | 0.398 | 15.148 | 44.065 | 1.00 | 40.98 |
| ATOM | 2210 | C | LEU | 298 | −4.140 | 14.935 | 42.130 | 1.00 | 35.87 |
| ATOM | 2211 | O | LEU | 298 | −4.108 | 14.282 | 41.082 | 1.00 | 37.02 |
| ATOM | 2212 | N | LYS | 299 | −5.121 | 14.826 | 43.024 | 1.00 | 39.60 |
| ATOM | 2213 | CA | LYS | 299 | −6.244 | 13.907 | 42.829 | 1.00 | 40.27 |
| ATOM | 2214 | CB | LYS | 299 | −7.160 | 13.931 | 44.065 | 1.00 | 50.54 |
| ATOM | 2215 | CG | LYS | 299 | −8.483 | 13.168 | 43.924 | 1.00 | 57.76 |
| ATOM | 2216 | CD | LYS | 299 | −9.589 | 14.024 | 43.293 | 1.00 | 65.14 |
| ATOM | 2217 | CE | LYS | 299 | −10.111 | 15.106 | 44.249 | 1.00 | 64.94 |
| ATOM | 2218 | NZ | LYS | 299 | −9.106 | 16.143 | 44.613 | 1.00 | 49.66 |
| ATOM | 2219 | C | LYS | 299 | −7.030 | 14.278 | 41.577 | 1.00 | 41.51 |
| ATOM | 2220 | O | LYS | 299 | −7.279 | 13.431 | 40.707 | 1.00 | 34.68 |
| ATOM | 2221 | N | GLU | 300 | −7.417 | 15.550 | 41.492 | 1.00 | 38.30 |
| ATOM | 2222 | CA | GLU | 300 | −8.168 | 16.043 | 40.351 | 1.00 | 36.22 |
| ATOM | 2223 | CB | GLU | 300 | −8.660 | 17.462 | 40.604 | 1.00 | 37.83 |
| ATOM | 2224 | CG | GLU | 300 | −9.201 | 18.118 | 39.362 | 1.00 | 50.01 |
| ATOM | 2225 | CD | GLU | 300 | −9.760 | 19.487 | 39.630 | 1.00 | 61.30 |
| ATOM | 2226 | OE1 | GLU | 300 | −10.863 | 19.570 | 40.207 | 1.00 | 66.64 |
| ATOM | 2227 | OE2 | GLU | 300 | −9.093 | 20.482 | 39.271 | 1.00 | 66.38 |
| ATOM | 2228 | C | GLU | 300 | −7.303 | 16.012 | 39.097 | 1.00 | 34.66 |
| ATOM | 2229 | O | GLU | 300 | −7.773 | 15.631 | 38.018 | 1.00 | 33.50 |
| ATOM | 2230 | N | PHE | 301 | −6.043 | 16.417 | 39.217 | 1.00 | 33.69 |
| ATOM | 2231 | CA | PHE | 301 | −5.183 | 16.382 | 38.046 | 1.00 | 35.31 |
| ATOM | 2232 | CB | PHE | 301 | −3.717 | 16.543 | 38.407 | 1.00 | 39.48 |
| ATOM | 2233 | CG | PHE | 301 | −2.791 | 16.117 | 37.307 | 1.00 | 39.84 |
| ATOM | 2234 | CD1 | PHE | 301 | −2.673 | 16.876 | 36.146 | 1.00 | 48.93 |
| ATOM | 2235 | CD2 | PHE | 301 | −2.074 | 14.936 | 37.406 | 1.00 | 39.43 |
| ATOM | 2236 | CE1 | PHE | 301 | −1.847 | 16.456 | 35.096 | 1.00 | 47.46 |
| ATOM | 2237 | CE2 | PHE | 301 | −1.248 | 14.508 | 36.364 | 1.00 | 37.65 |
| ATOM | 2238 | CZ | PHE | 301 | −1.134 | 15.266 | 35.209 | 1.00 | 42.30 |
| ATOM | 2239 | C | PHE | 301 | −5.363 | 15.006 | 37.449 | 1.00 | 38.95 |
| ATOM | 2240 | O | PHE | 301 | −5.357 | 14.841 | 36.230 | 1.00 | 38.38 |
| ATOM | 2241 | N | LYS | 302 | −5.517 | 14.024 | 38.340 | 1.00 | 42.57 |
| ATOM | 2242 | CA | LYS | 302 | −5.712 | 12.622 | 37.977 | 1.00 | 43.63 |
| ATOM | 2243 | CB | LYS | 302 | −5.465 | 11.732 | 39.197 | 1.00 | 54.86 |
| ATOM | 2244 | CG | LYS | 302 | −5.667 | 10.247 | 38.944 | 1.00 | 67.93 |
| ATOM | 2245 | CD | LYS | 302 | −5.694 | 9.461 | 40.253 | 1.00 | 77.32 |
| ATOM | 2246 | CE | LYS | 302 | −5.878 | 7.965 | 40.019 | 1.00 | 79.96 |

TABLE 2-continued

Atomic coordinates on the three-dimensional crystal structure of the FabK-
FMN complex having the amino acid sequences 2-312 of SEQ ID NO: 1

| A | B | C | D | E | F | G | H | I | J |
|---|---|---|---|---|---|---|---|---|---|
| ATOM | 2247 | NZ | LYS | 302 | −4.750 | 7.367 | 39.247 | 1.00 | 83.94 |
| ATOM | 2248 | C | LYS | 302 | −7.131 | 12.392 | 37.454 | 1.00 | 42.39 |
| ATOM | 2249 | O | LYS | 302 | −7.318 | 11.736 | 36.431 | 1.00 | 31.71 |
| ATOM | 2250 | N | GLU | 303 | −8.126 | 12.922 | 38.164 | 1.00 | 46.27 |
| ATOM | 2251 | CA | GLU | 303 | −9.518 | 12.782 | 37.745 | 1.00 | 49.85 |
| ATOM | 2252 | CB | GLU | 303 | −10.417 | 13.694 | 38.570 | 1.00 | 61.19 |
| ATOM | 2253 | CG | GLU | 303 | −11.878 | 13.581 | 38.208 | 1.00 | 81.07 |
| ATOM | 2254 | CD | GLU | 303 | −12.732 | 14.561 | 38.970 | 1.00 | 89.88 |
| ATOM | 2255 | OE1 | GLU | 303 | −12.663 | 14.557 | 40.216 | 1.00 | 96.74 |
| ATOM | 2256 | OE2 | GLU | 303 | −13.472 | 15.334 | 38.325 | 1.00 | 91.77 |
| ATOM | 2257 | C | GLU | 303 | −9.569 | 13.197 | 36.283 | 1.00 | 50.36 |
| ATOM | 2258 | O | GLU | 303 | −10.046 | 12.447 | 35.419 | 1.00 | 47.93 |
| ATOM | 2259 | N | THR | 304 | −9.076 | 14.409 | 36.022 | 1.00 | 47.48 |
| ATOM | 2260 | CA | THR | 304 | −8.987 | 14.943 | 34.661 | 1.00 | 44.69 |
| ATOM | 2261 | CB | THR | 304 | −8.475 | 16.397 | 34.656 | 1.00 | 43.06 |
| ATOM | 2262 | OG1 | THR | 304 | −9.026 | 17.113 | 35.769 | 1.00 | 44.35 |
| ATOM | 2263 | CG2 | THR | 304 | −8.876 | 17.086 | 33.368 | 1.00 | 40.43 |
| ATOM | 2264 | C | THR | 304 | −7.878 | 14.067 | 34.104 | 1.00 | 42.22 |
| ATOM | 2265 | O | THR | 304 | −6.992 | 13.702 | 34.855 | 1.00 | 48.07 |
| ATOM | 2266 | N | VAL | 305 | −7.911 | 13.735 | 32.820 | 1.00 | 40.59 |
| ATOM | 2267 | CA | VAL | 305 | −6.887 | 12.860 | 32.193 | 1.00 | 40.66 |
| ATOM | 2268 | CB | VAL | 305 | −5.592 | 12.610 | 33.053 | 1.00 | 33.72 |
| ATOM | 2269 | CG1 | VAL | 305 | −4.702 | 11.573 | 32.380 | 1.00 | 28.13 |
| ATOM | 2270 | CG2 | VAL | 305 | −4.786 | 13.876 | 33.182 | 1.00 | 34.50 |
| ATOM | 2271 | C | VAL | 305 | −7.536 | 11.513 | 31.956 | 1.00 | 38.76 |
| ATOM | 2272 | O | VAL | 305 | −7.536 | 11.016 | 30.837 | 1.00 | 39.32 |
| ATOM | 2273 | N | GLU | 306 | −8.067 | 10.910 | 33.013 | 1.00 | 41.93 |
| ATOM | 2274 | CA | GLU | 306 | −8.762 | 9.645 | 32.849 | 1.00 | 48.21 |
| ATOM | 2275 | CB | GLU | 306 | −9.276 | 9.135 | 34.190 | 1.00 | 52.19 |
| ATOM | 2276 | CG | GLU | 306 | −8.218 | 8.488 | 35.052 | 1.00 | 68.83 |
| ATOM | 2277 | CD | GLU | 306 | −8.772 | 8.021 | 36.380 | 1.00 | 81.16 |
| ATOM | 2278 | OE1 | GLU | 306 | −8.090 | 7.229 | 37.064 | 1.00 | 85.14 |
| ATOM | 2279 | OE2 | GLU | 306 | −9.888 | 8.453 | 36.743 | 1.00 | 85.53 |
| ATOM | 2280 | C | GLU | 306 | −9.933 | 10.048 | 31.968 | 1.00 | 47.16 |
| ATOM | 2281 | O | GLU | 306 | −10.300 | 9.359 | 31.017 | 1.00 | 46.96 |
| ATOM | 2282 | N | LYS | 307 | −10.488 | 11.207 | 32.302 | 1.00 | 46.44 |
| ATOM | 2283 | CA | LYS | 307 | −11.606 | 11.795 | 31.585 | 1.00 | 41.18 |
| ATOM | 2284 | CB | LYS | 307 | −11.966 | 13.123 | 32.247 | 1.00 | 44.29 |
| ATOM | 2285 | CG | LYS | 307 | −13.388 | 13.572 | 32.021 | 1.00 | 55.55 |
| ATOM | 2286 | CD | LYS | 307 | −13.944 | 14.204 | 33.292 | 1.00 | 64.41 |
| ATOM | 2287 | CE | LYS | 307 | −13.868 | 13.232 | 34.478 | 1.00 | 67.79 |
| ATOM | 2288 | NZ | LYS | 307 | −14.440 | 13.792 | 35.744 | 1.00 | 67.30 |
| ATOM | 2289 | C | LYS | 307 | −11.228 | 12.017 | 30.119 | 1.00 | 34.37 |
| ATOM | 2290 | O | LYS | 307 | −12.003 | 11.718 | 29.212 | 1.00 | 34.87 |
| ATOM | 2291 | N | LEU | 308 | −10.033 | 12.544 | 29.894 | 1.00 | 29.88 |
| ATOM | 2292 | CA | LEU | 308 | −9.564 | 12.797 | 28.543 | 1.00 | 35.17 |
| ATOM | 2293 | CB | LEU | 308 | −8.241 | 13.564 | 28.570 | 1.00 | 33.53 |
| ATOM | 2294 | CG | LEU | 308 | −8.303 | 14.867 | 29.370 | 1.00 | 38.94 |
| ATOM | 2295 | CD1 | LEU | 308 | −6.978 | 15.602 | 29.276 | 1.00 | 30.75 |
| ATOM | 2296 | CD2 | LEU | 308 | −9.434 | 15.758 | 28.830 | 1.00 | 29.69 |
| ATOM | 2297 | C | LEU | 308 | −9.381 | 11.469 | 27.835 | 1.00 | 39.88 |
| ATOM | 2298 | O | LEU | 308 | −9.653 | 11.348 | 26.636 | 1.00 | 38.23 |
| ATOM | 2299 | N | ARG | 309 | −8.909 | 10.473 | 28.578 | 1.00 | 44.63 |
| ATOM | 2300 | CA | ARG | 309 | −8.722 | 9.151 | 28.013 | 1.00 | 50.63 |
| ATOM | 2301 | CB | ARG | 309 | −8.306 | 8.163 | 29.097 | 1.00 | 62.19 |
| ATOM | 2302 | CG | ARG | 309 | −8.505 | 6.712 | 28.703 | 1.00 | 75.11 |
| ATOM | 2303 | CD | ARG | 309 | −8.176 | 5.790 | 29.853 | 1.00 | 80.82 |
| ATOM | 2304 | NE | ARG | 309 | −6.762 | 5.856 | 30.195 | 1.00 | 89.30 |
| ATOM | 2305 | CZ | ARG | 309 | −6.209 | 5.181 | 31.193 | 1.00 | 95.68 |
| ATOM | 2306 | NH1 | ARG | 309 | −6.954 | 4.390 | 31.954 | 1.00 | 99.08 |
| ATOM | 2307 | NH2 | ARG | 309 | −4.907 | 5.289 | 31.423 | 1.00 | 102.35 |
| ATOM | 2308 | C | ARG | 309 | −10.069 | 8.747 | 27.444 | 1.00 | 50.37 |
| ATOM | 2309 | O | ARG | 309 | −10.162 | 8.266 | 26.312 | 1.00 | 49.52 |
| ATOM | 2310 | N | GLY | 310 | −11.108 | 8.972 | 28.244 | 1.00 | 49.29 |
| ATOM | 2311 | CA | GLY | 310 | −12.466 | 8.643 | 27.852 | 1.00 | 52.11 |
| ATOM | 2312 | C | GLY | 310 | −12.794 | 8.964 | 26.407 | 1.00 | 55.41 |
| ATOM | 2313 | O | GLY | 310 | −13.515 | 8.207 | 25.746 | 1.00 | 51.93 |
| ATOM | 2314 | N | TYR | 311 | −12.270 | 10.083 | 25.911 | 1.00 | 56.04 |
| ATOM | 2315 | CA | TYR | 311 | −12.514 | 10.484 | 24.529 | 1.00 | 55.03 |
| ATOM | 2316 | CB | TYR | 311 | −12.130 | 11.960 | 24.325 | 1.00 | 53.97 |
| ATOM | 2317 | CG | TYR | 311 | −13.023 | 12.928 | 25.085 | 1.00 | 49.67 |
| ATOM | 2318 | CD1 | TYR | 311 | −12.570 | 13.590 | 26.232 | 1.00 | 48.91 |
| ATOM | 2319 | CE1 | TYR | 311 | −13.419 | 14.436 | 26.970 | 1.00 | 43.49 |
| ATOM | 2320 | CD2 | TYR | 311 | −14.345 | 13.140 | 24.690 | 1.00 | 51.41 |

TABLE 2-continued

Atomic coordinates on the three-dimensional crystal structure of the FabK-FMN complex having the amino acid sequences 2-312 of SEQ ID NO: 1

| A | B | C | D | E | F | G | H | I | J |
|---|---|---|---|---|---|---|---|---|---|
| ATOM | 2321 | CE2 | TYR | 311 | −15.203 | 13.982 | 25.424 | 1.00 | 48.67 |
| ATOM | 2322 | CZ | TYR | 311 | −14.731 | 14.621 | 26.559 | 1.00 | 45.81 |
| ATOM | 2323 | OH | TYR | 311 | −15.584 | 15.421 | 27.280 | 1.00 | 44.15 |
| ATOM | 2324 | C | TYR | 311 | −11.763 | 9.582 | 23.539 | 1.00 | 55.53 |
| ATOM | 2325 | O | TYR | 311 | −11.592 | 9.929 | 22.373 | 1.00 | 54.47 |
| ATOM | 2326 | N | ILE | 312 | −11.328 | 8.415 | 24.010 | 1.00 | 58.10 |
| ATOM | 2327 | CA | ILE | 312 | −10.614 | 7.464 | 23.162 | 1.00 | 57.58 |
| ATOM | 2328 | CB | ILE | 312 | −9.095 | 7.722 | 23.218 | 1.00 | 58.00 |
| ATOM | 2329 | CG2 | ILE | 312 | −8.353 | 6.627 | 22.470 | 1.00 | 56.14 |
| ATOM | 2330 | CG1 | ILE | 312 | −8.788 | 9.097 | 22.616 | 1.00 | 51.74 |
| ATOM | 2331 | CD1 | ILE | 312 | −7.326 | 9.454 | 22.594 | 1.00 | 48.60 |
| ATOM | 2332 | C | ILE | 312 | −10.905 | 5.993 | 23.506 | 1.00 | 53.86 |
| ATOM | 2333 | O | ILE | 312 | −10.570 | 5.504 | 24.586 | 1.00 | 49.23 |
| ATOM | 2334 | N1 | FMN | 2208 | 6.888 | 37.416 | 41.487 | 1.00 | 38.43 |
| ATOM | 2335 | C2 | FMN | 2208 | 8.204 | 37.744 | 41.552 | 1.00 | 40.66 |
| ATOM | 2336 | O2 | FMN | 2208 | 9.013 | 37.393 | 40.712 | 1.00 | 41.65 |
| ATOM | 2337 | N3 | FMN | 2208 | 8.575 | 38.527 | 42.671 | 1.00 | 52.52 |
| ATOM | 2338 | C4 | FMN | 2208 | 7.722 | 39.001 | 43.729 | 1.00 | 48.54 |
| ATOM | 2339 | O4 | FMN | 2208 | 8.183 | 39.670 | 44.646 | 1.00 | 58.78 |
| ATOM | 2340 | C4A | FMN | 2208 | 6.385 | 38.625 | 43.607 | 1.00 | 49.27 |
| ATOM | 2341 | N5 | FMN | 2208 | 5.380 | 38.937 | 44.492 | 1.00 | 45.14 |
| ATOM | 2342 | C5A | FMN | 2208 | 4.036 | 38.615 | 44.495 | 1.00 | 40.49 |
| ATOM | 2343 | C6 | FMN | 2208 | 3.157 | 39.056 | 45.592 | 1.00 | 33.68 |
| ATOM | 2344 | C7 | FMN | 2208 | 1.740 | 38.675 | 45.564 | 1.00 | 34.16 |
| ATOM | 2345 | C7M | FMN | 2208 | 0.869 | 39.147 | 46.730 | 1.00 | 39.55 |
| ATOM | 2346 | C8 | FMN | 2208 | 1.230 | 37.865 | 44.429 | 1.00 | 37.20 |
| ATOM | 2347 | C8M | FMN | 2208 | −0.247 | 37.384 | 44.253 | 1.00 | 40.85 |
| ATOM | 2348 | C9 | FMN | 2208 | 2.154 | 37.471 | 43.386 | 1.00 | 38.44 |
| ATOM | 2349 | C9A | FMN | 2208 | 3.581 | 37.832 | 43.395 | 1.00 | 39.67 |
| ATOM | 2350 | N10 | FMN | 2208 | 4.614 | 37.479 | 42.419 | 1.00 | 38.65 |
| ATOM | 2351 | C10 | FMN | 2208 | 5.997 | 37.825 | 42.459 | 1.00 | 43.28 |
| ATOM | 2352 | C1* | FMN | 2208 | 4.264 | 36.629 | 41.182 | 1.00 | 43.64 |
| ATOM | 2353 | C2* | FMN | 2208 | 3.356 | 35.436 | 41.400 | 1.00 | 49.52 |
| ATOM | 2354 | O2* | FMN | 2208 | 3.898 | 34.527 | 42.352 | 1.00 | 48.66 |
| ATOM | 2355 | C3* | FMN | 2208 | 3.104 | 34.693 | 40.109 | 1.00 | 55.58 |
| ATOM | 2356 | O3* | FMN | 2208 | 2.594 | 35.575 | 39.108 | 1.00 | 72.95 |
| ATOM | 2357 | C4* | FMN | 2208 | 2.110 | 33.559 | 40.433 | 1.00 | 62.99 |
| ATOM | 2358 | O4* | FMN | 2208 | 2.301 | 32.440 | 39.557 | 1.00 | 75.59 |
| ATOM | 2359 | C5* | FMN | 2208 | 0.670 | 33.983 | 40.245 | 1.00 | 55.61 |
| ATOM | 2360 | O5* | FMN | 2208 | −0.159 | 32.922 | 40.558 | 1.00 | 53.28 |
| ATOM | 2361 | P | FMN | 2208 | −1.698 | 32.973 | 40.505 | 1.00 | 38.94 |
| ATOM | 2362 | O1P | FMN | 2208 | −2.134 | 34.093 | 41.367 | 1.00 | 46.35 |
| ATOM | 2363 | O2P | FMN | 2208 | −2.031 | 33.193 | 39.100 | 1.00 | 42.17 |
| ATOM | 2364 | O3P | FMN | 2208 | −2.044 | 31.604 | 40.938 | 1.00 | 49.91 |
| ATOM | 2365 | FE+3 | FE3 | 400 | −12.957 | 33.204 | 44.628 | 1.00 | 47.39 |
| ATOM | 2366 | OH2 | WAT | 2209 | −0.833 | 29.770 | 38.935 | 1.00 | 36.10 |
| ATOM | 2367 | OH2 | WAT | 2210 | −4.436 | 33.988 | 37.939 | 1.00 | 37.80 |
| ATOM | 2368 | OH2 | WAT | 2211 | 2.511 | 37.761 | 33.467 | 1.00 | 44.03 |
| ATOM | 2369 | OH2 | WAT | 2212 | −6.505 | 25.975 | 37.703 | 1.00 | 31.30 |
| ATOM | 2370 | OH2 | WAT | 2213 | 10.886 | 14.424 | 42.585 | 1.00 | 49.45 |
| ATOM | 2371 | OH2 | WAT | 2214 | 14.917 | 40.647 | 45.612 | 1.00 | 41.86 |
| ATOM | 2372 | OH2 | WAT | 2215 | 6.538 | 34.255 | 40.676 | 1.00 | 44.52 |
| ATOM | 2373 | OH2 | WAT | 2216 | −9.832 | 50.747 | 48.079 | 1.00 | 41.69 |
| ATOM | 2374 | OH2 | WAT | 2217 | −7.662 | 20.515 | 42.330 | 1.00 | 38.27 |
| ATOM | 2375 | OH2 | WAT | 2218 | 3.498 | 14.581 | 42.175 | 1.00 | 48.91 |
| ATOM | 2376 | OH2 | WAT | 2219 | −0.940 | 8.574 | 45.059 | 1.00 | 49.80 |
| ATOM | 2377 | OH2 | WAT | 2220 | 16.081 | 25.242 | 22.498 | 1.00 | 42.13 |
| ATOM | 2378 | OH2 | WAT | 2221 | 5.069 | 38.974 | 38.628 | 1.00 | 48.67 |
| ATOM | 2379 | OH2 | WAT | 2222 | −2.851 | 27.886 | 22.972 | 1.00 | 37.95 |
| ATOM | 2380 | OH2 | WAT | 2223 | 2.720 | 37.334 | 30.140 | 1.00 | 41.55 |
| ATOM | 2381 | OH2 | WAT | 2224 | 5.418 | 33.562 | 18.335 | 1.00 | 42.83 |
| ATOM | 2382 | OH2 | WAT | 2225 | −10.194 | 23.574 | 45.926 | 1.00 | 43.13 |
| ATOM | 2383 | OH2 | WAT | 2226 | 15.173 | 43.443 | 48.224 | 1.00 | 44.26 |
| ATOM | 2384 | OH2 | WAT | 2227 | −6.426 | 56.032 | 49.649 | 1.00 | 52.18 |
| ATOM | 2385 | OH2 | WAT | 2228 | 17.852 | 21.835 | 56.566 | 1.00 | 42.54 |
| ATOM | 2386 | OH2 | WAT | 2229 | 8.414 | 22.026 | 29.271 | 1.00 | 47.62 |
| ATOM | 2387 | OH2 | WAT | 2230 | 0.480 | 47.707 | 42.098 | 1.00 | 44.20 |
| ATOM | 2388 | OH2 | WAT | 2231 | 4.669 | 39.490 | 27.224 | 1.00 | 41.39 |
| ATOM | 2389 | OH2 | WAT | 2232 | 11.927 | 21.677 | 62.125 | 1.00 | 47.54 |
| END | | | | | | | | | |

(In the Table 2,

A: atom, B: atomic number, C: atomic name, D: residue name corresponding to residues 2-312 of SEQ ID NO: 1, E: residue number corresponding to residues 2-312 of SEQ ID NO: 1, F: x-axis information, G: y-axis information, H: z-axis information, I: occupancy factor, and J: temperature factor)

Figure 9:
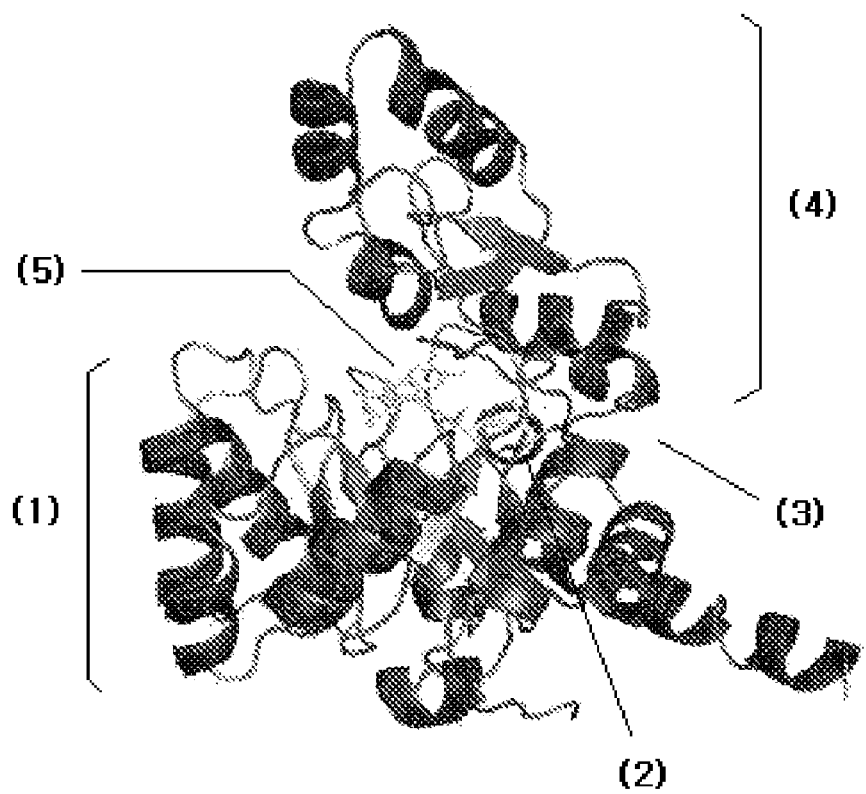
FIG. 9 shows the framework of FabK in terms of a C alpha ribbon, identifying (1) a part of TIM barrel, (2) a loop region, (3) a hinge region, (4) a cover region, and (5) a FMN molecule.
Figure 11A:
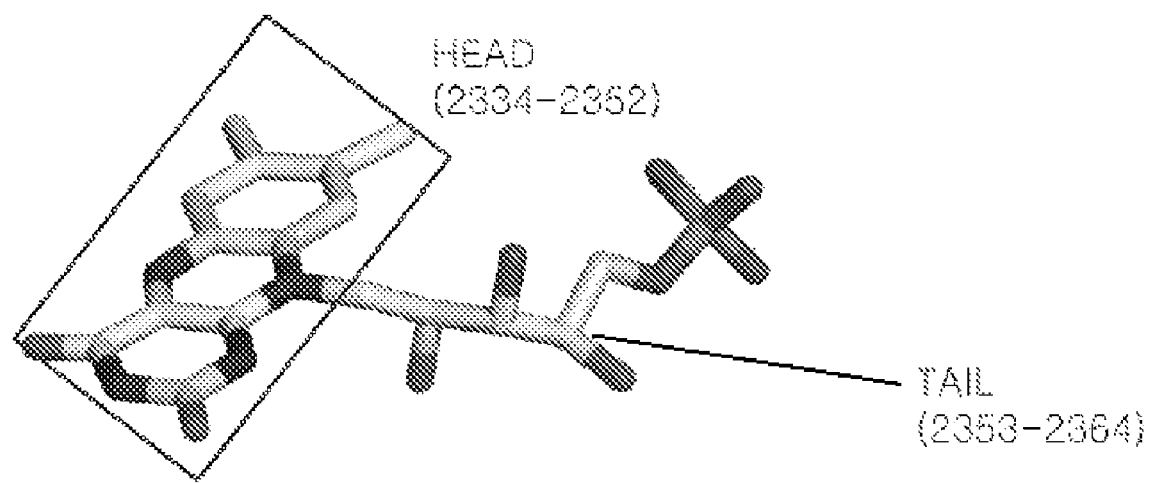
FIG. 11a shows schematically the structure of FMN.
Figure 11B:
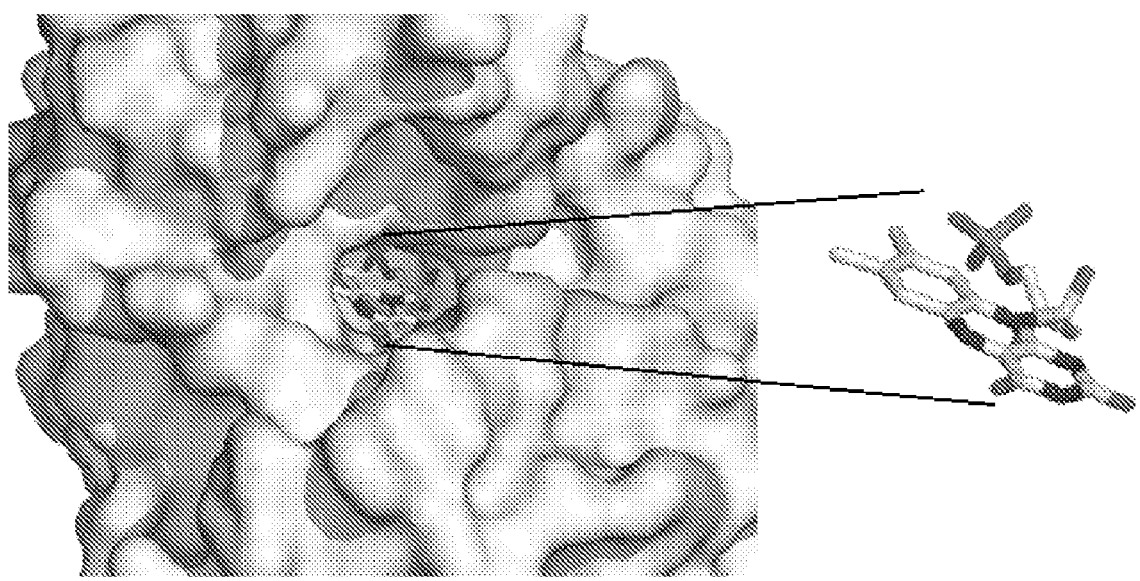
FIG. 11b shows the position of FMN at the FabK-FMN complex.

After the refinement step, in order to obtain various information from the atomic model, an analysis step can be additionally performed. For example, the distance and the space between each atom can be measured by observing the active site of the FabK model of the three-dimensional space located on a graphic, or if it is an important residue, the modeling process of screening appropriate inhibitors against the FabK protein can be performed by observing the spatial position of the important residue and the interaction between the residue and other residues. The structure of the FabK-FMN complex determined by the analysis step is shown in FIGS. 9, 11a and 11b. As shown in the figures, it was clarified that the site of the FabK protein binding to the FMN is a loop region located at the upper part of the TIM barrel (G. K. Farber and G. A. Petsko: The evolution of a/b barrel enzymes, TIBS 1990; 228-234), and therefore the site can be the active site of the FabK protein.

More specifically, FMN Molecule (5) is represented by the atoms from $2334^{th}$ to $2364^{th}$ position in Table 2, wherein the atoms from $2334^{th}$ to $2352^{nd}$ positions consist in a head region, and the atoms from $2353^{rd}$ to $2364^{th}$ positions consists in a tail region. The FMN molecule having such structure binds to a loop region (2) (loop 1: the atoms from $1015^{th}$ to $1103^{rd}$ positions, loop 2: the atoms from $141^{st}$ to $206^{th}$ positions, in Table 2), which resides on the upside region of TIM barrel (1) of FabK protein. Then, NADP, which is a coenzyme necessary for the FabK protein activity, and substrates for the FabK protein bind to the upper part of the FMN binding region. In addition, a hinge region (3) (the atom region from $1428^{th}$ to $1485^{th}$ positions in Table 2; the amino acid sequence from $198^{th}$ position to $205^{th}$ positions in SEQ ID NO: 1), which links the TIM barrel region (1) and the rest region (4) (hereinafter, 'the cap region'), allows flexibility to the complex. That is, the hinge region moves, thereby forming a space for binding of NADP and substrates, to allow the FabK protein to act. Therefore, the hinge region may be one of FabK protein activating regions.

Therefore, another FabK protein activating region is the upper region of the upside of the TIM barrel on which the FMN molecule is bound and placed, which provides a space for binding of NADP and substrates. That is, the FabK protein activating region is a hemisphere region including the cap region and the hinge region of the FabK-FMN molecule, wherein the base side of the hemisphere region is a horizontal plane of the head region of the FMN molecule bound on the TIM barrel. More specifically, the FabK protein activating region may be any part located within the hemisphere region with the horizontal plane of the head region of the FMN molecule bound on the TIM barrel as a flat base side, having the radius of 15 Å, preferably 6 to 12 Å. The hemisphere region may include the atoms from $1380^{th}$ to $2137^{th}$ positions in Table 2, which comprising the loop 1 region and hinge region.

Also, various mutants were made and tested to examine the amino acid sequence affecting the activity of the FabK protein. For performing the mutant test, after selecting one targeted amino acid of the amino acid sequence of SEQ ID NO: 1, the primer for transferring a nucleotide sequence coding the amino acid into a nucleotide sequence coding another amino acid, for example alanine, is made. 5'- and 3'-terminal primers are used, and these primers can additionally include a nucleotide sequence coding the amino acid modifying in the middle of the two primers to obtain the desired recombinant clone using the PCR method. The obtained recombinant clone is treated with the DpnI restriction enzyme, and the original vector obtained from E. coli is completely lysated. The reaction time of the restriction enzyme preferably can be from 30 min to 2 hours. And then, the recombinant clone only is transformed into E. coli, and thereby the mutant FabK protein is obtained.

Through the mutant test, when transferring tyrosine at the $208^{th}$ position (Y208) and lysine at the $209^{th}$ position (K209) of the FabK protein (SEQ ID NO: 1) according to the present invention into alanine, the activity of the transferred protein is increased. On the other hand, when transferring lysine at the $211^{th}$ position (K211), lysine at the $214^{th}$ position (K214), histidine at the $229^{th}$ position (H229), and leucine at the $261^{st}$ position (L261) of the FabK protein (SEQ ID NO: 1) into alanine, the activity of the transferred protein is decreased. Particularly, when transferring histidine at the $229^{th}$ position (H229) and methionine at $276^{th}$ position (M276) of the FabK protein (SEQ ID NO: 1) into alanine, the activity of the transferred protein is dramatically decreased. Therefore, the amino acids can be regarded as very important amino acids affecting the activity of the FabK protein. Moreover, because the deletion of a helix having 8 amino acids from the $208^{th}$ to $215^{th}$ positions and a helix having 6 amino acids from the $278^{th}$ to $283^{rd}$ positions of the FabK protein (SEQ ID NO: 1) according to the present invention dramatically decreases the activity of the FabK protein, and the two helix sites can also be regarded as very important sites affecting the activity of the FabK protein.

Therefore, a more effective inhibitor against the FabK protein can be preferably selected by detecting the interaction between a candidate compound and at least one site selected from the group consisting of a loop region located at the upper part of TIM barrel; one ore more amino acids located within the hemisphere region with the horizontal plane of the head region of the FMN molecule bound on the TIM barrel of FabK protein as a flat base side, and having the radius of 15 Å, preferably 6 to 12 Å; a hinge region including the amino acids from $198^{th}$ to $205^{th}$ positions of SEQ ID NO: 1; tyrosine at the $208^{th}$ position (Y208); lysine at the $209^{th}$ position (K209); lysine at the $211^{th}$ position (K211); lysine at the $214^{th}$ position (K214); histidine at the $229^{th}$ position (H229); leucine at the $261^{st}$ position (L261); methionine at $276^{th}$ position (M276); a helix having 8 amino acids from the $208^{th}$ to $215^{th}$ positions; and a helix having 6 amino acids from the $278^{th}$ to $283^{rd}$ positions of the FabK protein (SEQ ID NO: 1) according to the present invention.

Therefore, in developing an inhibiting agent having inhibitory activities against the FabK protein, the development of the inhibiting agent can be more conveniently and more effectively performed by screening the inhibitor of the FabK protein, by designing a structure based compound having inhibitory activities against the FabK protein, or by using a virtual screening method, through using selectively the atomic coordinates corresponding to the active site of the 2389 atomic coordinates shown in Table 2.

Also, the present invention provides a storage media able to be read with a computer, for example, a floppy diskette or a hard disk, wherein the storage media stores the information about the three-dimensional crystal structure of the FabK. The three-dimensional crystal structure stored in the storage media can include all or part of the atomic coordinates (particularly, the atomic coordinates corresponding to the active site), or can include the information about the site including the amino acid of the active site and the amino acid residue of the mutant.

Based on the three-dimensional crystal structure of the FabK protein, the specific positional characterization affecting the interaction between the FabK and FMN and the role of individual amino acids affecting the activity at the active site, the present invention provides a method of screening the FabK inhibitor having inhibitory activities against the FabK protein. The screening method according to the present invention can include the steps of: reacting the FabK protein having the amino acid sequence of SEQ ID NO: 1 with candidate compounds; and screening a compound from the candidate compounds, which interacts with the FabK protein.

The FabK protein can be crystallized by the crystallizing method. In the screening compounds interacting with the FabK protein, a compound having inhibitory activities against the FabK protein can be more easily and more exactly selected by using the three-dimensional crystal structure and/or the information of the active site. The screening method can also use the storage media according to the present invention.

The present invention is further explained in more detail with reference to the following examples. These examples, however, should not be interpreted as limiting the scope of the present invention in any manner.

EXAMPLE

Example 1

Expression and Purification of the *Thermotoga maritima* FabK Protein

The gene coding FabK protein from methionine (N-terminus) at the $1^{st}$ amino acid to glutamate (C-terminus) at the $314^{th}$ amino acid of the *Thermotoga maritima* FabK (SEQ ID NO: 1) was synthesized and amplified by a Polymerase Chain Reaction (hereinafter referred to as 'PCR').

Each primer used for the PCR reaction is an oligonucleotide shown in SEQ ID NO: 2 and 3, wherein the primer has a Nde I and a Xho I restriction enzyme recognition site, respectively.

For the PCR reaction, after preparing a PCR reaction solution adding 37.4 μl distilled water to complex mixtures containing 1 μl genomic DNA (Accession No. AE000512, Genbank) as a template, 5 μl 2.5 mM dNTP, 0.3 μl 100 pmol of each primer set corresponding to SEQ ID NO: 1 and SEQ ID NO: 2, 1 μl PfuTaq DNA polymerase (5 U/μl, Stratagene Co., USA) and 5 μl PCR reaction buffer (Stratagene Co., USA), the PCR reaction was performed at 95° C. 5 min, 95° C. 30 sec, 55° C. 30 sec, and 72° C. 1 min using the PCR reaction solution. After 30 cycles, the amplified PCR product was assessed by electrophoresis on a 0.8% agarose gel and the FabK gene having the size of about 970 bp was isolated. The isolated FabK gene was treated with Nde I and Xho I restriction enzymes, and assessed by electrophoresis, and then the fragment of the FabK gene was extracted. The extract was dissolved in 50 μl distilled water, and it was designated as FabK N/X.

A plasmid pET-28a (Novagene Inc., USA) expressing 6 histidine residues in the N-terminus was treated with Nde I and Xho I restriction enzymes, and assessed by electrophoresis, and then the DNA fragment having the size of about 5400 bp was isolated. The isolated fragment was designated as pET-28a N/X. For cloning the FabK N/X into the pET-28a N/X, after adding distilled water to a reaction tube containing 0.5 μg FabK N/X, 0.1 μg pET-28a N/X, 2 μl 10× ligation reaction buffer (50 mM Tris-HCl, pH 7.8; 100 mM $MgCl_2$; 100 mM DTT; and 10 mM ATP), and 10 U T4 DNA ligase until the total volume become to 20 μl, the reaction tube was incubated for 12 h at 16° C. After the reaction, the obtained reaction solution was transformed into *E. coli* BL21 (DE3) (Novagene Inc., USA) competent cells, and the transformed cells were plated on an LB medium (1% bacto-trypsin, 0.5% yeast extract, and 1% sodium chloride) containing 50 μg/ml kanamycin, and then an *E. coli* transformant was selected. The recombinant plasmid from the transformant was extracted, and the recombinant plasmid pET-28a-FabK was obtained by restriction enzyme and DNA sequencing analysis.

The nucleotide sequences of the FabK gene cloned in the recombinant plasmid were confirmed by an ABI 377 DNA sequencer using a Big-Dye Cycle Sequencing System (Applied Biosystem Inc., USA).

The transformed *E. coli* strain was cultured in a Luria-Bertani (LB) broth medium including 50 μg/ml kanamycin for 12 hours, and 1 ml of the cultured medium was transferred into a 100 ml LB medium including 50 μg/ml kanamycin, and then IPTG (isopropyl-β-D-thiogalactopyranoside) was added to the LB medium at the final concentration of 0.5 mM when the absorbance of the cultured medium reached about 0.6 at 600 nm, 37° C. 4 hours after adding IPTG to the LB medium, the medium was centrifuged at 10,000 g for 30 min, and each cell extracts were obtained. The cell extracts were resuspended in a solution including 20 mM Tris (pH 8.0), 0.1 M NaCl, 1 mM TCEP (Tris(2-carboxyethyl)phosphine hydrchloride), and then were lysated on ice using sonicator.

After centrifugation, the supernatant was consecutively passed into a Ni-affinity column (Farmacia Inc., Sweden) and a BLUE column (Farmacia Inc., Sweden). The passed solution was purified by using Superdex-75 Gel filtration chromatography (Farmacia, Inc., Sweden), and the FabK protein was obtained.

Example 2

Crystallization of the FabK Protein According to the Hanging-drop Vapor Diffusion Method The FabK protein obtained from Example 1 was crystallized by the following hanging-drop vapor diffusion method.

The FabK protein solution having a concentration of 11 mg/ml, including 20 mM Tris-HCl (pH 8.0), 300 mM NaCl, 1 mM DTT, and 50 mM $NH_4Cl$, was prepared. The final concentration of the protein was determined by the Bradford method (Current Protocols in Protein Science, 3.4.10). The final protein solution was prepared by adding NADH (nicotineamide adenine dinucleotide) and FMN as cofactors to the protein solution concentrated to 11 mg/ml, wherein the mole equivalent ratio of the cofactors against FabK was 1:5.

The initial screening solution (Hampton Research Inc., USA) was used for searching optimal conditions of the FabK protein crystal, and Hydra II-plus one system (Matrix Technologies Corp., USA) was used for automatized screening. After mixing 0.2 μl protein solution and 0.2 μl reservoir solution, the mixed solution was incubated at 22° C. 2 to 20 days after incubation, it was confirmed whether crystallization had occurred or not. Consequently, in the case of using the reservoir solution consisting of 0.1 M bicine buffer solution (pH 9.0), 1 M lithium chloride, and 20% (v/v) PEG 6,000 precipitant, and using a reservoir solution consisting of 0.1 M Tris-HCl buffer (pH8.0), 0.2 M magnesium chloride, and 20% (v/v) PEG 20,000 precipitant, the crystal having the best x-ray diffraction quality was obtained.

A drop of mixed 1 μl final protein solution and 1 μl reservoir solution was dropped onto the surface of a glass slide coated with silicon, and the slide was covered on a plate including 0.5 ml reservoir solution, and then it was placed in a isothermal condition of 22° C. One day after, crystals of the seed formed, and the size of the crystals grew up to 0.1×0.1× 0.2 mm after a week.

Example 3

Crystallization of the FabK Protein According to Additive Flash-frozen Nitrogen Cooling Method In order to avoid a problem caused by directly exposing the FabK protein crystal obtained from Example 2 to x-rays having high energy, before the x-ray analysis of the FabK protein crystal, a flash-frozen nitrogen cooling method was performed as follows.

After searching various cryoprotectant solutions, such as glycerol, sodium formate, ethylene glycerol, sucrose, and paratone-N, under different concentrations, the optimal condition of the flash-frozen nitrogen cooling method was obtained. Consequently, if the crystal was dipped in a cryoprotectant solution for flash-frozen cooling including 25% (v/v) ethylene glycol, 0.1 M bicine buffer solution (pH 9.0), 1 M LiCl, and 20% (v/v) PEG 6,000 precipitant for several seconds and then taken out, it was shown to mostly endure against a liquid nitrogen stream at 100K, without causing any damage on the FabK crystal.

The crystal dipped in the cryoprotectant solution was trapped with about a 0.3 mm nylon crystal collection tool (Hampton Research Corp., USA), and immediately it was put in the 100K nitrogen stream.

In an embodiment of the present invention, the ice ring phenomena (a phenomena where water is frozen when the flash-frozen nitrogen is not perfect and shows up) often occurred on experiment was not shown.

Example 4

X-ray Diffraction Data Collection and Evaluation of the FabK Protein Crystal Using Synchrotron Radiation Accelerator Using the FabK crystal obtained from Example 3, an experiment collecting the diffraction data in the AR-NW12 line of the Japanese photon factory synchrotron radiation accelerator was performed. The limit of the crystal data is 2.3 Å, the data was processed with DENZO and SCALEPACK [Otwinowski, Z. and Minor, W. Methods Enzymol., 276, 461-472 (1997)]. The crystal data collection and refinement results are shown in Table 3.

TABLE 3

| | x-ray diffraction data collection | | | |
|---|---|---|---|---|
| Wavelength | 0.97891 | 0.97921 | 0.9814 | 0.978 |
| Space group | C2 | C2 | C2 | C2 |
| Unit cell | a = 65.611 | a = 65.724 | a = 65.797 | a = 65.611 |
| | b = 77.107 | b = 77.180 | b = 77.213 | b = 77.107 |
| | c = 59.085 | c = 59.172 | c = 59.230 | c = 59.085 |
| | $\alpha, \gamma = 90$ | $\alpha, \gamma = 90$ | $\alpha, \gamma = 90$ | $\alpha, \gamma = 90$ |
| | $\beta = 99.93$ | $\beta = 99.970$ | $\beta = 99.994$ | $\beta = 99.93$ |
| Resolution | 50.0-2.3 | 50.0-2.3 | 20.0-2.3 | 50.0-2.3 |
| Observations | 224880 | 228464 | 232136 | 224880 |
| Unique reflections | 13051 | 12928 | 12995 | 13051 |
| Completeness (%) | 94.5 (77.0) | 91.5 (68.6) | 87.3 (53.4) | 94.5 (77.0) |
| Average I/(I) | 34.5 (6.7) | 30.1 (5.1) | 27.8 (4.8) | 34.5 (6.7) |
| $Rsym_1$ (%) | 6.8 | 7.0 | 4.7 | 6.8 |
| | structure refinement | | | |
| Resolution | | 29.1 | 2.3 | |
| $Rcryst_2$ (%) | | | 0.243 | |
| $Rfree_3$ (%) | | | 0.242 | |
| Combination: combination deviation | | | 0.01 | |
| Angle (°): angle deviation | | | 1.4 | |
| Average thermal parameter of FabK | | | 47.1 | |
| Average thermal parameter of water molecules | | | 43.3 | |

The numerical values of ( ) of x-ray diffraction date collection indicate the values of outer resolution shell.
$Rsym_1 = \Sigma h \Sigma i |I h, i - <I h, i>|/\Sigma h \Sigma i \Sigma h$, i(about strength I of measured value i on reflectance h)
$Rcryst_2 = \Sigma |F_{measured\ values} F_{calculated\ values}|/\Sigma |F_{measured\ values}|$
$Rfree_3$ is to the R factor calculated by using 5% reflectance data which is randomly selected and is omitted in the early refinement stage.

Example 5

X-ray Diffraction Data Interpretation and Structural Calculation of the FabK Protein Crystal The structure of the FabK protein was determined by using the multiwavelength anomalous dispersion method. For obtaining initial phase information, the multiwavelength anomalous dispersion method used the SOLVE [Terwilliger T. C. and Berendzen J., Acta Crystallogr. D. Biol. Crystallogr. 55, 849-861 (1999)] program, and for obtaining collecting the electron density, the method used the RESOLVE [Terwilliger T. C., Acta Crystallogr. D. Biol. Crystallogr. 56, 965-972 (2000)]. Used diffraction data was refined at the resolution of 2.3 Å.

In the refinement step, the CNS program [Brunger, A T. et al., Acta Cryst. D., 54, 905-921 (1998)] was used. The refinement step was performed by using the simulation annealing method of the CNS program. The initial temperature of the simulation was 1500° C., and was frozen by 100° C. in each step, until 25° C. The final R factor and R free factor were 24.3% and 24.2%, respectively. And then, the optimal structure was built by using the O program. For drawing the optimal structure, the refinement step was performed by improving the electron density coming from the x-ray data using the O program to a computer monitor and repeating the task with modifying the structure to obtain the most fitting structure.

After performing the refinement step, it was clarified that the three-dimensional crystal structure of the FabK protein according to the present invention shows the structure of TIM barrel form and the activation site consisting of a loop located at the upper part of TIM barrel obviously differing from previous FabI structure, and FMN was combined with the three-dimensional crystal structure.

Example 6

The Effects of an Important Residue and the Activity Through Mutant Test of Individual Amino Acid Residues Located at the Center of FabK Activation Site After obtaining the three-dimensional crystal structure of the FabK protein from Example 5, in order to examine the role of individual amino acids in the FabK activation site, a mutation was made and the effect according to the activity of the mutation was observed.

The mutant of the individual residues was prepared by substituting tyrosine residue at the $208^{th}$ position with alanine (Y208A, SEQ ID NO: 4 and 5), lysine residue at the $209^{th}$ position with alanine (K209A, SEQ ID NO: 6 and 7), lysine residue at the $211^{th}$ position with alanine (K211A, SEQ ID NO: 8 and 9), lysine residue at the $214^{th}$ position with alanine (K214A, SEQ ID NO: 10 and 11), histidine residue at the $229^{th}$ position with alanine (H229A, SEQ ID NO: 12 and 13), leucine residue at the $261^{st}$ position with alanine (L261A, SEQ ID NO: 14 and 15), and methionine residue at $276^{th}$ position with alanine (M276A, SEQ ID NO: 16 and 17), respectively.

For examining an effect according to the deletion of the helix affecting the FabK activation site, the mutation proteins with deleted amino acid from the $208^{th}$ residue to the $215^{th}$ residue (8 amino acids: SEQ ID NO: 18 and SEQ ID NO: 19, hereinafter referred to as 'D208'), and deleted amino acid from the $278^{th}$ residue to the $283^{rd}$ residue (6 amino acids: SEQ ID NO: 20 and SEQ IN NO: 21, hereinafter referred to as 'D278') were prepared using the PCR method, respectively.

For preparing mutant having the modifying individual amino acids, the D208 and D278 mutant protein, an oligomer corresponding to a nucleotide sequence from SEQ ID NO: 4 to SEQ ID NO: 21 was synthesized, and then was amplified using the PCR method. After adding distilled water to complex mixtures containing 10 ng cloned pET-28a-FabK plasmid, 5 μl 2.5 mM dNTP, 0.2 μl of each primer, and 5 μl 10× PCR reaction buffer (100 mM KCl, 100 mM $(NH_4)_2SO_4$, 200 mM Tris-HCl(pH 8.8), 20 mM $MgSO_4$) until 50 μl, the PCR reaction was performed at 95° C. 1 min, 95° C. 50 sec, 60° C. 50 sec, and 68° C. 6 min. After 18 cycles, 0.5 μl dpn I (Stratagene Corp., USA) restriction enzyme was added to the amplified PCR product, and then the PCR product was incubated for 1 hour in a 37° C. incubator. The pET-28a-FabK plasmid derived from E. coli was lysated due to the Dpn I restriction enzyme, and thereby only the mutant pET-28a-FabK plasmid produced by the PCR reaction remained. The reaction product was transformed into E. coli DH5 α competent cells, and the transformed cells were plated on a LB medium including 50 μg/ml kanamycin, and then an E. coli transformant was selected. The plasmid was extracted, and the mutant pET-28a-FabK plasmid was confirmed by DNA sequencing analysis.

The obtained mutant pET-28a-FabK plasmid was transformed into E. coli BL21 (DE3) host cells, and the plasmid was purified by using the purification method according to Example 1.

Figure 7:
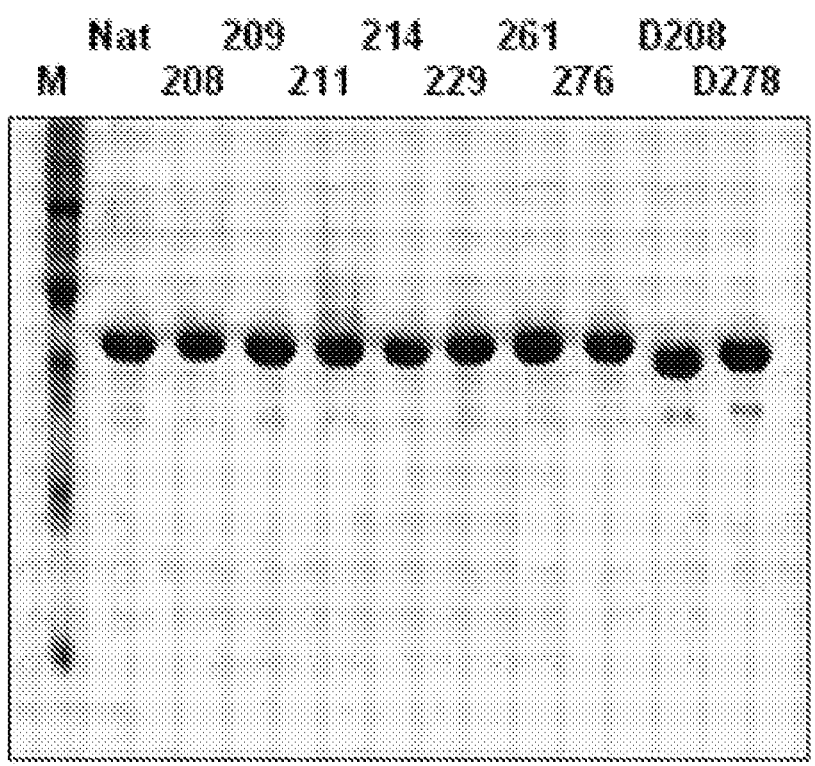
FIG. 7 shows results of the purification of an amino acid mutant in the active site of FabK.
Figure 8:
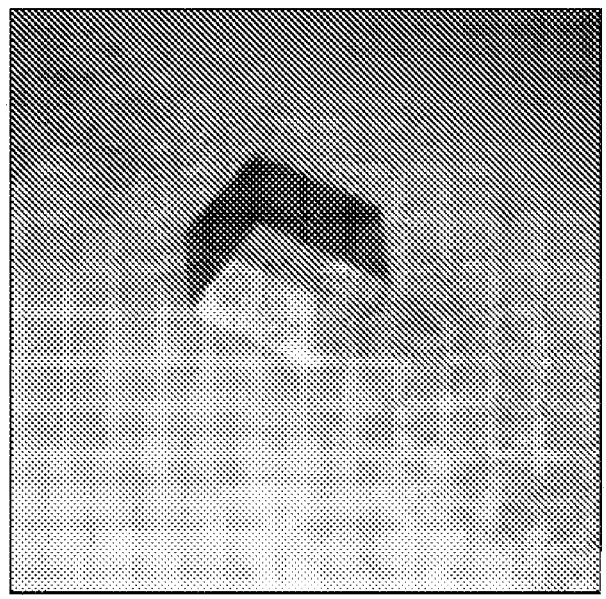
FIG. 8 shows the crystal structure of FabK.
Figure 10:
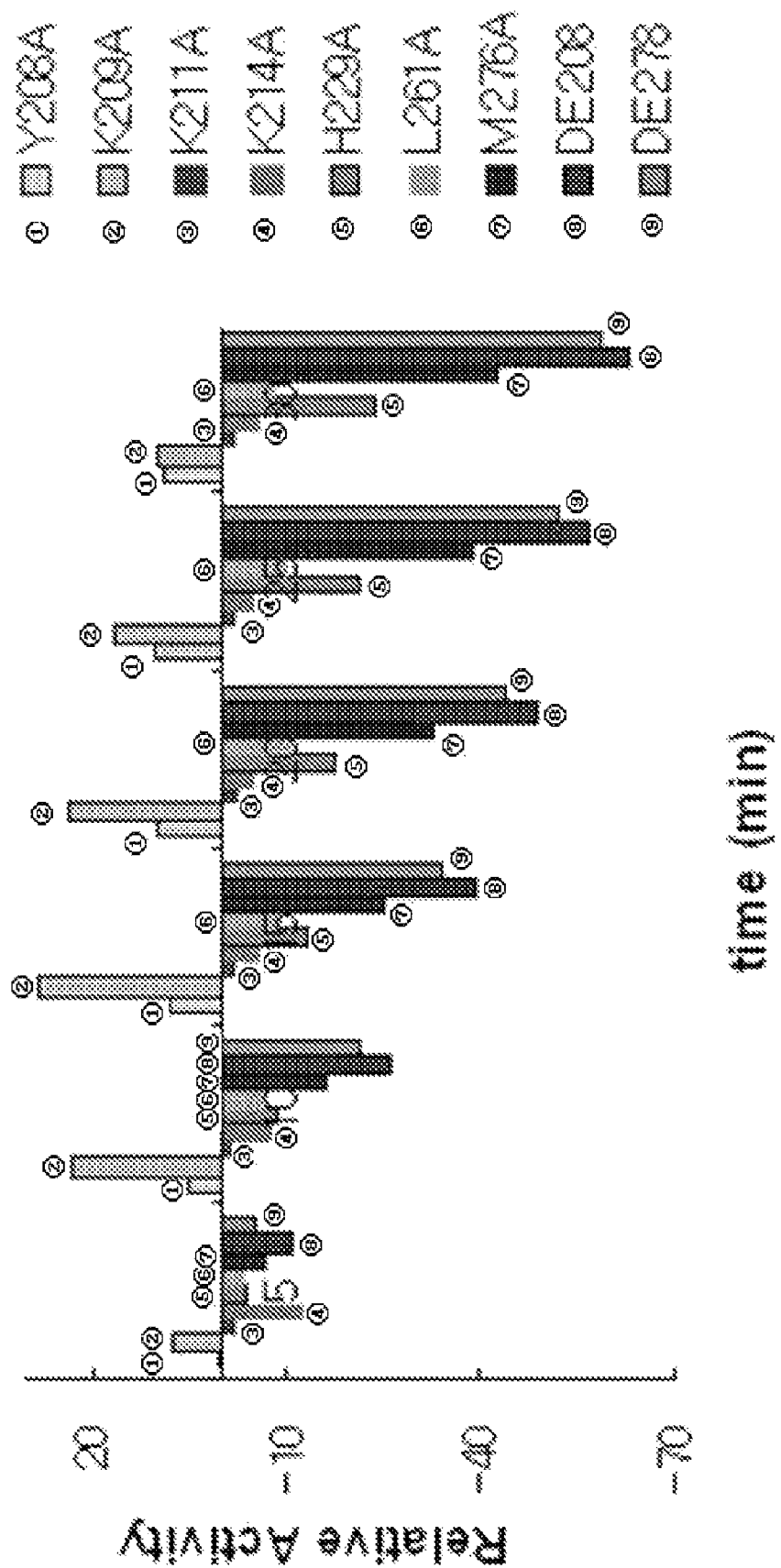
FIG. 10 shows the activity of a FabK mutant.

As shown in FIG. 7, the prepared mutant FabK protein was analyzed by electrophoresis on SDS-acrylamide gel. As shown in FIG. 10, the increase and decrease of the activity of the mutant FabK protein were observed. In the case of Y208A and K209A, the activities of the Y208A and K209A were both increased, and these residues inhibit the FabK activity. On the other hand, in the case of K211A, K214A, H229A, L261A, M276A, D208, and D278, the activities of these mutations were all decreased. Particularly, the activities of H229A and M276A were dramatically decreased, and the mutant with the helix of D208 and D278 removed was more severely decreased in that activity. These results indicate that histidine at the $229^{th}$ residue and methionine at the $276^{th}$ residue, and a helix supporting the FabK structure from the $208^{th}$ to the $215^{th}$, and from the $278^{th}$ to the $283^{rd}$, have an important function for maintaining the FabK activity.

As described in above, the present invention relates to the active site and the three-dimensional crystal structure of the FabK protein known as a protein targeting antibiotics. Because the FabK protein crystal derived from a *Thermotoga maritima* strain is excellent in the level of crystallization, as well as is facilitative in x-ray analysis and has a structural feature differing from an analog protein, FabI, the three-dimensional structure of the crystal can be usefully used for developing a novel compound with excellent antibiotic activities differing from the previous FabI inhibitor.

What is claimed is:

1. A method of identifying an inhibiting agent against FabK (enoyl-acyl carrier protein reductase), the method comprising:
   (a) generating on a computer a three-dimensional structure of a FabK-FMN (flavin mononucleotide) complex having the atomic coordinates of Table 2;
   (b) identifying amino acids of FabK forming an FMN binding site of FabK from the three-dimensional structure generated in step (a), wherein the amino acids of FabK forming the FMN binding site are amino acids 198-205, 208-215, 229, 261, 276, and 278-283 of SEQ ID NO:1;
   (c) generating a three-dimensional model of the FMN binding site of FabK, wherein the amino acids of the three-dimensional model have the atomic coordinates according to Table 2;

(d) employing said three-dimensional model from step (c) to identify a potential inhibiting agent of FabK;
(e) obtaining said potential inhibiting agent; and
(f) contacting said potential inhibiting agent with FabK to determine the ability of said potential inhibiting agent to inhibit FabK activity, whereby inhibition of FabK activity identifies said inhibiting agent.

2. The method according to claim 1, wherein the method is performed by using storage media which store information of the three-dimensional structure.

3. The method according to claim 1, wherein said potential inhibiting agent is identified in step (d) by using a virtual screening method.

4. The method according to claim 3, wherein the virtual screening method is performed using storage media which store information of the three-dimensional structure of the FabK-FMN complex.

* * * * *

SEQUENCE LISTING

```
<160> NUMBER OF SEQ ID NOS: 21

<210> SEQ ID NO 1
<211> LENGTH: 314
<212> TYPE: PRT
<213> ORGANISM: Artificial Sequence
<220> FEATURE:
<223> OTHER INFORMATION: amino acid sequence of FabK protein purified
      from Thermotoga maritima

<400> SEQUENCE: 1
```

```
Met Thr Val Arg Thr Arg Val Thr Asp Leu Leu Glu Ile Glu His Pro
 1               5                  10                  15

Ile Leu Met Gly Gly Met Ala Trp Ala Gly Thr Pro Thr Leu Ala Ala
             20                  25                  30

Ala Val Ser Glu Ala Gly Gly Leu Gly Ile Ile Gly Ser Gly Ala Met
         35                  40                  45

Lys Pro Asp Asp Leu Arg Lys Ala Ile Ser Glu Leu Arg Gln Lys Thr
     50                  55                  60

Asp Lys Pro Phe Gly Val Asn Ile Ile Leu Val Ser Pro Trp Ala Asp
 65                  70                  75                  80

Asp Leu Val Lys Val Cys Ile Glu Glu Lys Val Pro Val Val Thr Phe
                 85                  90                  95

Gly Ala Gly Asn Pro Thr Lys Tyr Ile Arg Glu Leu Lys Glu Asn Gly
                100                 105                 110

Thr Lys Val Ile Pro Val Ala Ser Asp Ser Leu Ala Arg Met Val
            115                 120                 125

Glu Arg Ala Gly Ala Asp Ala Val Ile Ala Glu Gly Met Glu Ser Gly
    130                 135                 140

Gly His Ile Gly Glu Val Thr Thr Phe Val Leu Val Asn Lys Val Ser
145                 150                 155                 160

Arg Ser Val Asn Ile Pro Val Ile Ala Ala Gly Gly Ile Ala Asp Gly
                165                 170                 175

Arg Gly Met Ala Ala Ala Phe Ala Leu Gly Ala Glu Ala Val Gln Met
                180                 185                 190

Gly Thr Arg Phe Val Ala Ser Val Glu Ser Asp Val His Pro Val Tyr
            195                 200                 205

Lys Glu Lys Ile Val Lys Ala Ser Ile Arg Asp Thr Val Val Thr Gly
    210                 215                 220

Ala Lys Leu Gly His Pro Ala Arg Val Leu Arg Thr Pro Phe Ala Arg
225                 230                 235                 240

Lys Ile Gln Glu Met Glu Phe Glu Asn Pro Met Gln Ala Glu Glu Met
                245                 250                 255

Leu Val Gly Ser Leu Arg Arg Ala Val Val Glu Gly Asp Leu Glu Arg
                260                 265                 270

Gly Ser Phe Met Val Gly Gln Ser Ala Gly Leu Ile Asp Glu Ile Lys
            275                 280                 285

Pro Val Lys Gln Ile Ile Glu Asp Ile Leu Lys Glu Phe Lys Glu Thr
    290                 295                 300

Val Glu Lys Leu Arg Gly Tyr Ile Glu Glu
305                 310
```

<210> SEQ ID NO 2
<211> LENGTH: 34
<212> TYPE: DNA
<213> ORGANISM: Artificial Sequence
<220> FEATURE:
<223> OTHER INFORMATION: 5' primer comprising NdeI restriction enzyme
      recognition site

<400> SEQUENCE: 2
gggaattcca tatgaccgtg agaacaagag tgac                              34

<210> SEQ ID NO 3
<211> LENGTH: 28
<212> TYPE: DNA
<213> ORGANISM: Artificial Sequence

```
<220> FEATURE:
<223> OTHER INFORMATION: 3' primer comprising XhoI restriction enzyme
      recognition site

<400> SEQUENCE: 3
ggcctcgagt cactcttcga tgtacccc                                           28

<210> SEQ ID NO 4
<211> LENGTH: 39
<212> TYPE: DNA
<213> ORGANISM: Artificial Sequence
<220> FEATURE:
<223> OTHER INFORMATION: 5' primer for producing a variant Y208A

<400> SEQUENCE: 4
cgacgtgcac ccggttgcaa agaaaagat cgtcaaggc                                39

<210> SEQ ID NO 5
<211> LENGTH: 39
<212> TYPE: DNA
<213> ORGANISM: Artificial Sequence
<220> FEATURE:
<223> OTHER INFORMATION: 3' primer for producing a variant Y208A

<400> SEQUENCE: 5
gccttgacga tcttttcttt tgcaaccggg tgcacgtcg                               39

<210> SEQ ID NO 6
<211> LENGTH: 35
<212> TYPE: DNA
<213> ORGANISM: Artificial Sequence
<220> FEATURE:
<223> OTHER INFORMATION: 5' primer for producing a variant K209A

<400> SEQUENCE: 6
gtgcacccgg tttacgcaga aaagatcgtc aaggc                                   35

<210> SEQ ID NO 7
<211> LENGTH: 35
<212> TYPE: DNA
<213> ORGANISM: Artificial Sequence
<220> FEATURE:
<223> OTHER INFORMATION: 3' primer for producing a variant K209A

<400> SEQUENCE: 7
gccttgacga tcttttctgc gtaaaccggg tgcac                                   35

<210> SEQ ID NO 8
<211> LENGTH: 45
<212> TYPE: DNA
<213> ORGANISM: Artificial Sequence
<220> FEATURE:
<223> OTHER INFORMATION: 5' primer for producing a variant K211A

<400> SEQUENCE: 8
gtgcacccgg tttacaaaga agcaatcgtc aaggcttcca taaga                        45

<210> SEQ ID NO 9
<211> LENGTH: 45
<212> TYPE: DNA
<213> ORGANISM: Artificial Sequence
<220> FEATURE:
<223> OTHER INFORMATION: 3' primer for producing a variant K211A

<400> SEQUENCE: 9
tcttatggaa gccttgacga ttgcttcttt gtaaaccggg tgcac                        45
```

<210> SEQ ID NO 10
<211> LENGTH: 45
<212> TYPE: DNA
<213> ORGANISM: Artificial Sequence
<220> FEATURE:
<223> OTHER INFORMATION: 5' primer for producing a variant K214A

<400> SEQUENCE: 10
ggtttacaaa gaaaagatcg tcgcagcttc cataagagac accgt                45

<210> SEQ ID NO 11
<211> LENGTH: 45
<212> TYPE: DNA
<213> ORGANISM: Artificial Sequence
<220> FEATURE:
<223> OTHER INFORMATION: 3' primer for producing a variant K214A

<400> SEQUENCE: 11
acggtgtctc ttatggaagc tgcgacgatc ttttctttgt aaacc                45

<210> SEQ ID NO 12
<211> LENGTH: 41
<212> TYPE: DNA
<213> ORGANISM: Artificial Sequence
<220> FEATURE:
<223> OTHER INFORMATION: 5' primer for producing a variant H229A

<400> SEQUENCE: 12
agaaatgctg gtgggaagtg caagaagagc ggtcgttgaa g                    41

<210> SEQ ID NO 13
<211> LENGTH: 41
<212> TYPE: DNA
<213> ORGANISM: Artificial Sequence
<220> FEATURE:
<223> OTHER INFORMATION: 3' primer for producing a variant H229A

<400> SEQUENCE: 13
cttcaacgac cgctcttctt gcacttccca ccagcatttc t                    41

<210> SEQ ID NO 14
<211> LENGTH: 33
<212> TYPE: DNA
<213> ORGANISM: Artificial Sequence
<220> FEATURE:
<223> OTHER INFORMATION: 5' primer for producing a variant L261A

<400> SEQUENCE: 14
ggagagagga tccttcgcag tgggacagag cgc                             33

<210> SEQ ID NO 15
<211> LENGTH: 33
<212> TYPE: DNA
<213> ORGANISM: Artificial Sequence
<220> FEATURE:
<223> OTHER INFORMATION: 3' primer for producing a variant L261A

<400> SEQUENCE: 15
gcgctctgtc ccactgcgaa ggatcctctc tcc                             33

<210> SEQ ID NO 16
<211> LENGTH: 33
<212> TYPE: DNA
<213> ORGANISM: Artificial Sequence
<220> FEATURE:

-continued

```
<223> OTHER INFORMATION: 5' primer for producing a variant M276A

<400> SEQUENCE: 16
gggagccaaa cttggagcac ccgcgcgcgt tct                           33

<210> SEQ ID NO 17
<211> LENGTH: 33
<212> TYPE: DNA
<213> ORGANISM: Artificial Sequence
<220> FEATURE:
<223> OTHER INFORMATION: 3' primer for producing a variant M276A

<400> SEQUENCE: 17
agaacgcgcg cgggtgctcc aagtttggct ccc                           33

<210> SEQ ID NO 18
<211> LENGTH: 30
<212> TYPE: DNA
<213> ORGANISM: Artificial Sequence
<220> FEATURE:
<223> OTHER INFORMATION: 5' primer for producing a variant D208

<400> SEQUENCE: 18
acgtgcaccc ggtttccata agagacaccg                               30

<210> SEQ ID NO 19
<211> LENGTH: 30
<212> TYPE: DNA
<213> ORGANISM: Artificial Sequence
<220> FEATURE:
<223> OTHER INFORMATION: 3' primer for producing a variant D208

<400> SEQUENCE: 19
cggtgtctct tatggaaacc gggtgcacgt                               30

<210> SEQ ID NO 20
<211> LENGTH: 36
<212> TYPE: DNA
<213> ORGANISM: Artificial Sequence
<220> FEATURE:
<223> OTHER INFORMATION: 5' primer for producing a variant D278

<400> SEQUENCE: 20
gaggatcctt catggtgatc gatgagataa aaccgg                        36

<210> SEQ ID NO 21
<211> LENGTH: 36
<212> TYPE: DNA
<213> ORGANISM: Artificial Sequence
<220> FEATURE:
<223> OTHER INFORMATION: 3' primer for producing a variant D278

<400> SEQUENCE: 21
ccggttttat ctcatcgatc accatgaagg atcctc                        36
```